US008868172B2

(12) United States Patent
Leyde et al.

(10) Patent No.: US 8,868,172 B2
(45) Date of Patent: Oct. 21, 2014

(54) METHODS AND SYSTEMS FOR RECOMMENDING AN APPROPRIATE ACTION TO A PATIENT FOR MANAGING EPILEPSY AND OTHER NEUROLOGICAL DISORDERS

(75) Inventors: Kent W. Leyde, Sammamish, WA (US); Daniel J. Dilorenzo, Seattle, WA (US)

(73) Assignee: Cyberonics, Inc., Houston, TX (US)

( * ) Notice: Subject to any disclaimer, the term of this patent is extended or adjusted under 35 U.S.C. 154(b) by 856 days.

(21) Appl. No.: 11/321,897

(22) Filed: Dec. 28, 2005

(65) Prior Publication Data

US 2007/0150024 A1    Jun. 28, 2007

(51) Int. Cl.
| | | |
|---|---|---|
| *A61B 5/04* | (2006.01) | |
| *A61N 1/372* | (2006.01) | |
| *A61B 5/0476* | (2006.01) | |
| *A61N 1/36* | (2006.01) | |
| *A61B 5/00* | (2006.01) | |
| *A61B 5/048* | (2006.01) | |

(52) U.S. Cl.
CPC .......... *A61B 5/4094* (2013.01); *A61N 1/37258* (2013.01); *A61B 5/0476* (2013.01); *A61N 1/37247* (2013.01); *A61N 1/36082* (2013.01); *A61B 5/7275* (2013.01); *A61B 5/7264* (2013.01); *A61B 5/048* (2013.01)
USPC ...................................................... 600/544

(58) Field of Classification Search
USPC .............. 607/45–46, 115–116; 600/300, 378, 600/544–545
See application file for complete search history.

(56) References Cited

U.S. PATENT DOCUMENTS

| | | |
|---|---|---|
| 3,218,638 A | 11/1965 | Honig |
| 3,498,287 A | 3/1970 | Ertl |
| 3,522,811 A | 8/1970 | Schwartz |
| 3,575,162 A | 4/1971 | Gaarder |
| 3,837,331 A | 9/1974 | Ross |
| 3,850,161 A | 11/1974 | Liss |
| 3,863,625 A | 2/1975 | Viglione et al. |
| 3,882,850 A | 5/1975 | Bailin et al. |
| 3,918,461 A | 11/1975 | Cooper |
| 3,967,616 A | 7/1976 | Ross |
| 3,993,046 A | 11/1976 | Fernandez |

(Continued)

FOREIGN PATENT DOCUMENTS

| | | |
|---|---|---|
| CA | 2251852 | 4/1999 |
| CA | 2423840 | 2/2002 |

(Continued)

OTHER PUBLICATIONS

Leyde, Kent; U.S. Appl. No. 11/599,179, entitled "Systems and methods of reducing artifact in neurological stimulation systems," filed Nov. 14, 2006.

(Continued)

*Primary Examiner* — Rex R Holmes
(74) *Attorney, Agent, or Firm* — Cyberonics, Inc.

(57) ABSTRACT

The present invention provides methods and system for managing neurological disorders such as epilepsy. In one embodiment, the method comprises measuring one or more signals from a patient and processing the one or more signals to characterize a patient's propensity for a future seizure. The characterized propensity for the seizure is thereafter used to determine an appropriate action for managing or treating the predicted seizure; and a recommendation is communicated to the patient that is indicative of the appropriate action.

25 Claims, 19 Drawing Sheets

(56) References Cited

U.S. PATENT DOCUMENTS

| | | |
|---|---|---|
| 4,201,224 A | 5/1980 | John |
| 4,214,591 A | 7/1980 | Sato et al. |
| 4,279,258 A | 7/1981 | John |
| 4,305,402 A | 12/1981 | Katims |
| 4,334,545 A | 6/1982 | Shiga |
| 4,407,299 A | 10/1983 | Culver |
| 4,408,616 A | 10/1983 | Duffy et al. |
| 4,421,122 A | 12/1983 | Duffy |
| 4,471,786 A | 9/1984 | Inagaki |
| 4,494,950 A | 1/1985 | Fischell |
| 4,505,275 A | 3/1985 | Chen |
| 4,545,388 A | 10/1985 | John |
| 4,556,061 A | 12/1985 | Barreras et al. |
| 4,566,464 A | 1/1986 | Piccone et al. |
| 4,573,481 A | 3/1986 | Bullara |
| 4,579,125 A | 4/1986 | Strobl et al. |
| 4,590,946 A | 5/1986 | Loeb |
| 4,612,934 A | 9/1986 | Borkan |
| 4,679,144 A | 7/1987 | Cox et al. |
| 4,686,999 A | 8/1987 | Snyder et al. |
| 4,702,254 A | 10/1987 | Zabara |
| 4,735,208 A | 4/1988 | Wyler et al. |
| 4,768,176 A | 8/1988 | Kehr et al. |
| 4,768,177 A | 8/1988 | Kehr et al. |
| 4,785,827 A | 11/1988 | Fischer |
| 4,793,353 A | 12/1988 | Borkan |
| 4,817,628 A | 4/1989 | Zealear |
| 4,838,272 A | 6/1989 | Lieber |
| 4,844,075 A | 7/1989 | Liss et al. |
| 4,852,573 A | 8/1989 | Kennedy |
| 4,867,164 A | 9/1989 | Zabara |
| 4,873,981 A | 10/1989 | Abrams et al. |
| 4,878,498 A | 11/1989 | Abrams et al. |
| 4,903,702 A | 2/1990 | Putz |
| 4,920,979 A | 5/1990 | Bullara |
| 4,926,865 A | 5/1990 | Oman |
| 4,955,380 A | 9/1990 | Edell |
| 4,978,680 A | 12/1990 | Sofia |
| 4,979,511 A | 12/1990 | Terry, Jr. |
| 4,991,582 A | 2/1991 | Byers et al. |
| 5,010,891 A | 4/1991 | Chamoun |
| 5,016,635 A | 5/1991 | Graupe |
| 5,025,807 A | 6/1991 | Zabara |
| 5,031,618 A | 7/1991 | Mullett |
| 5,070,873 A | 12/1991 | Graupe et al. |
| 5,082,861 A | 1/1992 | Sofia |
| 5,097,835 A | 3/1992 | Putz |
| RE34,015 E | 8/1992 | Duffy |
| 5,154,172 A | 10/1992 | Terry |
| 5,167,229 A | 12/1992 | Peckham et al. |
| 5,179,950 A | 1/1993 | Stanislaw |
| 5,181,520 A | 1/1993 | Wertheim et al. |
| 5,186,170 A | 2/1993 | Varichio |
| 5,188,104 A | 2/1993 | Wernicke |
| 5,190,029 A | 3/1993 | Byron et al. |
| 5,193,539 A | 3/1993 | Schulman et al. |
| 5,193,540 A | 3/1993 | Schulman et al. |
| 5,205,285 A | 4/1993 | Baker, Jr. |
| 5,215,086 A | 6/1993 | Terry, Jr. et al. |
| 5,215,088 A | 6/1993 | Normann |
| 5,215,089 A | 6/1993 | Baker, Jr. |
| 5,222,494 A | 6/1993 | Baker, Jr. |
| 5,222,503 A | 6/1993 | Ives |
| 5,231,988 A | 8/1993 | Wernicke et al. |
| 5,235,980 A | 8/1993 | Varichio et al. |
| 5,237,991 A | 8/1993 | Baker, Jr. |
| 5,251,634 A | 10/1993 | Weinberg |
| 5,263,480 A | 11/1993 | Wernicke et al. |
| 5,265,619 A | 11/1993 | Comby et al. |
| 5,269,302 A | 12/1993 | Swartz et al. |
| 5,269,303 A | 12/1993 | Wernicke et al. |
| 5,269,315 A | 12/1993 | Leuchter et al. |
| 5,292,772 A | 3/1994 | Sofia |
| 5,293,879 A | 3/1994 | Vonk |
| 5,299,118 A | 3/1994 | Martens et al. |
| 5,299,569 A | 4/1994 | Wernicke et al. |
| 5,300,094 A | 4/1994 | Kallok et al. |
| 5,304,206 A | 4/1994 | Baker, Jr. et al. |
| 5,311,876 A | 5/1994 | Olsen et al. |
| 5,312,439 A | 5/1994 | Loeb |
| 5,314,458 A | 5/1994 | Najafi et al. |
| 5,324,316 A | 6/1994 | Schulman et al. |
| 5,330,515 A | 7/1994 | Rutecki et al. |
| 5,335,657 A | 8/1994 | Terry et al. |
| 5,342,408 A | 8/1994 | deCoriolis et al. |
| 5,342,409 A | 8/1994 | Mullett |
| 5,343,064 A | 8/1994 | Spangler et al. |
| 5,349,962 A | 9/1994 | Lockard et al. |
| 5,351,394 A | 10/1994 | Weinberg |
| 5,361,760 A | 11/1994 | Normann |
| 5,365,939 A | 11/1994 | Ochs |
| 5,376,359 A | 12/1994 | Johnson |
| 5,392,788 A | 2/1995 | Hudspeth |
| 5,405,365 A | 4/1995 | Hoegnelid et al. |
| 5,405,367 A | 4/1995 | Schulman et al. |
| 5,411,540 A | 5/1995 | Edell et al. |
| 5,458,117 A | 10/1995 | Chamoun |
| 5,474,547 A | 12/1995 | Aebischer et al. |
| 5,476,494 A | 12/1995 | Edell et al. |
| 5,486,999 A | 1/1996 | Mebane |
| 5,513,649 A | 5/1996 | Gevins |
| 5,531,778 A | 7/1996 | Maschino et al. |
| 5,540,730 A | 7/1996 | Terry |
| 5,540,734 A | 7/1996 | Zabara |
| 5,549,656 A | 8/1996 | Reiss |
| 5,555,191 A | 9/1996 | Hripcsak |
| 5,571,148 A | 11/1996 | Loeb et al. |
| 5,571,150 A | 11/1996 | Wernicke |
| 5,575,813 A | 11/1996 | Edell et al. |
| 5,578,036 A | 11/1996 | Stone et al. |
| 5,611,350 A | 3/1997 | John |
| 5,626,145 A | 5/1997 | Clapp et al. |
| 5,626,627 A | 5/1997 | Krystal et al. |
| 5,638,826 A | 6/1997 | Wolpaw |
| 5,649,068 A | 7/1997 | Boser et al. |
| 5,672,154 A | 9/1997 | Sillen et al. |
| 5,683,422 A | 11/1997 | Rise |
| 5,683,432 A | 11/1997 | Goedeke et al. |
| 5,690,681 A | 11/1997 | Geddes et al. |
| 5,690,691 A | 11/1997 | Chen et al. |
| 5,697,369 A | 12/1997 | Long |
| 5,700,282 A | 12/1997 | Zabara |
| 5,704,352 A | 1/1998 | Tremblay et al. |
| 5,707,400 A | 1/1998 | Terry et al. |
| 5,711,316 A | 1/1998 | Elsberry et al. |
| 5,713,923 A | 2/1998 | Ward et al. |
| 5,715,821 A | 2/1998 | Faupel |
| 5,716,377 A | 2/1998 | Rise et al. |
| 5,720,294 A | 2/1998 | Skinner |
| 5,735,814 A | 4/1998 | Elsberry et al. |
| 5,743,860 A | 4/1998 | Hively et al. |
| 5,752,979 A | 5/1998 | Benabid |
| 5,769,778 A | 6/1998 | Abrams et al. |
| 5,776,434 A | 7/1998 | Purewal et al. |
| 5,782,798 A | 7/1998 | Rise |
| 5,782,874 A | 7/1998 | Loos |
| 5,782,891 A | 7/1998 | Hassler et al. |
| 5,792,186 A | 8/1998 | Rise |
| 5,800,474 A | 9/1998 | Bernabid et al. |
| 5,813,993 A | 9/1998 | Kaplan |
| 5,814,014 A | 9/1998 | Elsberry et al. |
| 5,815,413 A | 9/1998 | Hively et al. |
| 5,816,247 A | 10/1998 | Maynard |
| 5,824,021 A | 10/1998 | Rise |
| 5,832,932 A | 11/1998 | Elsberry et al. |
| 5,833,709 A | 11/1998 | Rise et al. |
| 5,857,978 A | 1/1999 | Hively et al. |
| 5,862,803 A | 1/1999 | Besson et al. |
| 5,876,424 A | 3/1999 | O'Phelan et al. |
| 5,899,922 A | 5/1999 | Loos |
| 5,913,881 A | 6/1999 | Benz et al. |
| 5,916,239 A | 6/1999 | Geddes et al. |
| 5,917,429 A | 6/1999 | Otis, Jr. et al. |
| 5,928,272 A | 7/1999 | Adkins |

(56) References Cited

U.S. PATENT DOCUMENTS

| | | | |
|---|---|---|---|
| 5,931,791 | A | 8/1999 | Saltzstein et al. |
| 5,938,689 | A | 8/1999 | Fischell et al. |
| 5,941,106 | A | 8/1999 | Barreras et al. |
| 5,941,906 | A | 8/1999 | Barreras et al. |
| 5,950,632 | A | 9/1999 | Reber et al. |
| 5,957,861 | A | 9/1999 | Combs et al. |
| 5,971,594 | A | 10/1999 | Sahai et al. |
| 5,975,085 | A | 11/1999 | Rise |
| 5,978,702 | A * | 11/1999 | Ward et al. ............... 607/3 |
| 5,978,710 | A | 11/1999 | Prutchi et al. |
| 5,995,868 | A | 11/1999 | Dorfmeister et al. |
| 6,006,124 | A | 12/1999 | Fischell et al. |
| 6,016,449 | A | 1/2000 | Fischell et al. |
| 6,018,682 | A | 1/2000 | Rise |
| 6,042,548 | A | 3/2000 | Giuffre |
| 6,042,579 | A | 3/2000 | Elsberry et al. |
| 6,051,017 | A | 4/2000 | Loeb et al. |
| 6,052,619 | A | 4/2000 | John |
| 6,061,593 | A | 5/2000 | Fischell et al. |
| 6,066,163 | A | 5/2000 | John |
| 6,081,744 | A | 6/2000 | Loos |
| 6,094,598 | A | 7/2000 | Elsberry et al. |
| 6,104,956 | A | 8/2000 | Naritoku |
| 6,109,269 | A | 8/2000 | Rise et al. |
| 6,117,066 | A | 9/2000 | Abrams et al. |
| 6,128,537 | A | 10/2000 | Rise et al. |
| 6,128,538 | A | 10/2000 | Fischell et al. |
| 6,134,474 | A | 10/2000 | Fischell et al. |
| 6,161,045 | A | 12/2000 | Fischell et al. |
| 6,167,304 | A | 12/2000 | Loos |
| 6,171,239 | B1 | 1/2001 | Humphrey |
| 6,176,242 | B1 | 1/2001 | Rise |
| 6,205,359 | B1 | 3/2001 | Boveja |
| 6,208,893 | B1 | 3/2001 | Hofmann |
| 6,221,011 | B1 | 4/2001 | Bardy |
| 6,227,203 | B1 | 5/2001 | Rise et al. |
| 6,230,049 | B1 | 5/2001 | Fischell et al. |
| 6,248,126 | B1 | 6/2001 | Lesser et al. |
| 6,249,703 | B1 | 6/2001 | Stanton |
| 6,263,237 | B1 | 7/2001 | Rise |
| 6,280,198 | B1 | 8/2001 | Calhoun et al. |
| 6,304,775 | B1 * | 10/2001 | Iasemidis et al. ............ 600/544 |
| 6,309,406 | B1 | 10/2001 | Jones et al. |
| 6,328,699 | B1 | 12/2001 | Eigler |
| 6,337,997 | B1 | 1/2002 | Rise |
| 6,339,725 | B1 | 1/2002 | Naritoku |
| 6,341,236 | B1 | 1/2002 | Osorio et al. |
| 6,343,226 | B1 | 1/2002 | Sunde et al. |
| 6,353,754 | B1 | 3/2002 | Fischell et al. |
| 6,354,299 | B1 | 3/2002 | Fischell et al. |
| 6,356,784 | B1 | 3/2002 | Lozano et al. |
| 6,356,788 | B2 | 3/2002 | Boveja |
| 6,358,203 | B2 | 3/2002 | Bardy |
| 6,358,281 | B1 | 3/2002 | Berrang et al. |
| 6,360,122 | B1 | 3/2002 | Fischell |
| 6,366,813 | B1 | 4/2002 | DiLorenzo |
| 6,366,814 | B1 | 4/2002 | Boveja |
| 6,374,140 | B1 | 4/2002 | Rise |
| 6,386,882 | B1 | 5/2002 | Linberg |
| 6,402,678 | B1 | 6/2002 | Fischell et al. |
| 6,411,854 | B1 | 6/2002 | Tziviskos et al. |
| 6,427,086 | B1 | 7/2002 | Fischell et al. |
| 6,434,419 | B1 | 8/2002 | Gevins et al. |
| 6,442,421 | B1 | 8/2002 | Quyen et al. |
| 6,443,891 | B1 | 9/2002 | Grevious |
| 6,453,198 | B1 | 9/2002 | Torgerson |
| 6,459,936 | B2 | 10/2002 | Fischell |
| 6,463,328 | B1 | 10/2002 | John |
| 6,466,822 | B1 | 10/2002 | Pless |
| 6,471,645 | B1 | 10/2002 | Warkentin et al. |
| 6,473,639 | B1 | 10/2002 | Fischell et al. |
| 6,473,644 | B1 | 10/2002 | Terry et al. |
| 6,480,743 | B1 | 11/2002 | Kirkpatrick |
| 6,484,132 | B1 | 11/2002 | Hively et al. |
| 6,488,617 | B1 | 12/2002 | Katz |
| 6,496,724 | B1 | 12/2002 | Levendowski et al. |
| 6,505,077 | B1 | 1/2003 | Kast et al. |
| 6,507,754 | B2 | 1/2003 | Quyen et al. |
| 6,510,340 | B1 | 1/2003 | Jordan |
| 6,511,424 | B1 | 1/2003 | Moore-Ede |
| 6,529,774 | B1 | 3/2003 | Greene |
| 6,534,693 | B2 | 3/2003 | Fischell et al. |
| 6,547,746 | B1 | 4/2003 | Marino |
| 6,549,804 | B1 | 4/2003 | Osorio et al. |
| 6,553,262 | B1 | 4/2003 | Lang et al. |
| 6,560,486 | B1 | 5/2003 | Osorio et al. |
| 6,571,123 | B2 | 5/2003 | Ives et al. |
| 6,571,125 | B2 | 5/2003 | Thompson |
| 6,572,528 | B2 | 6/2003 | Rohan et al. |
| 6,587,719 | B1 | 7/2003 | Barrett et al. |
| 6,587,727 | B2 | 7/2003 | Osorio et al. |
| 6,591,132 | B2 | 7/2003 | Gotman et al. |
| 6,591,137 | B1 | 7/2003 | Fischell et al. |
| 6,591,138 | B1 | 7/2003 | Fischell et al. |
| 6,594,524 | B2 | 7/2003 | Esteller et al. |
| 6,597,953 | B2 | 7/2003 | Boling |
| 6,597,954 | B1 | 7/2003 | Pless et al. |
| 6,600,956 | B2 | 7/2003 | Maschino |
| 6,606,521 | B2 | 8/2003 | Paspa et al. |
| 6,609,025 | B2 | 8/2003 | Barrett et al. |
| 6,618,623 | B1 | 9/2003 | Pless et al. |
| 6,620,415 | B2 | 9/2003 | Donovan |
| 6,622,036 | B1 | 9/2003 | Suffin |
| 6,622,038 | B2 | 9/2003 | Barrett et al. |
| 6,622,041 | B2 | 9/2003 | Terry et al. |
| 6,622,047 | B2 | 9/2003 | Barrett et al. |
| 6,647,296 | B2 | 11/2003 | Fischell et al. |
| 6,650,779 | B2 | 11/2003 | Vachtesvanos et al. |
| 6,658,287 | B1 | 12/2003 | Litt et al. |
| 6,662,035 | B2 | 12/2003 | Sochor |
| 6,665,562 | B2 | 12/2003 | Gluckman et al. |
| 6,668,191 | B1 | 12/2003 | Boveja |
| 6,671,555 | B2 | 12/2003 | Gielen |
| 6,671,556 | B2 | 12/2003 | Osorio |
| 6,678,548 | B1 | 1/2004 | Echauz et al. |
| 6,684,105 | B2 | 1/2004 | Cohen et al. |
| 6,687,538 | B1 | 2/2004 | Hrdlicka et al. |
| 6,690,974 | B2 | 2/2004 | Archer et al. |
| 6,721,603 | B2 | 4/2004 | Zabara |
| 6,735,467 | B2 | 5/2004 | Wilson |
| 6,760,626 | B1 | 7/2004 | Boveja |
| 6,768,969 | B1 | 7/2004 | Nikitin et al. |
| 6,778,854 | B2 | 8/2004 | Puskas |
| 6,782,292 | B2 | 8/2004 | Whitehurst |
| 6,788,975 | B1 | 9/2004 | Whitehurst |
| 6,793,670 | B2 | 9/2004 | Osorio |
| 6,810,285 | B2 | 10/2004 | Pless et al. |
| 6,819,956 | B2 | 11/2004 | DiLorenzo |
| 6,824,512 | B2 | 11/2004 | Warkentin et al. |
| 6,873,872 | B2 | 3/2005 | Gluckman et al. |
| 6,879,859 | B1 | 4/2005 | Boveja |
| 6,893,395 | B1 | 5/2005 | Kraus et al. |
| 6,901,292 | B2 | 5/2005 | Hrdlicka et al. |
| 6,901,294 | B1 | 5/2005 | Whitehurst et al. |
| 6,901,296 | B1 | 5/2005 | Whitehurst et al. |
| 6,904,390 | B2 | 6/2005 | Nikitin et al. |
| 6,912,419 | B2 | 6/2005 | Hill |
| 6,920,357 | B2 | 7/2005 | Osorio |
| 6,921,538 | B2 | 7/2005 | Donovan |
| 6,921,541 | B2 | 7/2005 | Chasin et al. |
| 6,923,784 | B2 | 8/2005 | Stein |
| 6,931,274 | B2 | 8/2005 | Williams |
| 6,934,580 | B1 | 8/2005 | Osorio |
| 6,937,891 | B2 | 8/2005 | Leinders et al. |
| 6,944,501 | B1 | 9/2005 | Pless |
| 6,950,706 | B2 | 9/2005 | Rodriguez |
| 6,961,618 | B2 | 11/2005 | Osorio |
| 6,973,342 | B1 | 12/2005 | Swanson |
| 6,990,372 | B2 | 1/2006 | Perron et al. |
| 7,010,351 | B2 | 3/2006 | Firlik et al. |
| 7,089,059 | B1 * | 8/2006 | Pless ............... 607/45 |
| 7,117,108 | B2 | 10/2006 | Rapp et al. |
| 7,174,212 | B1 | 2/2007 | Klehn et al. |
| 7,177,701 | B1 | 2/2007 | Pianca |

(56) References Cited

U.S. PATENT DOCUMENTS

| | | |
|---|---|---|
| 7,212,851 B2 | 5/2007 | Donoghue et al. |
| 7,373,198 B2 | 5/2008 | Bibian et al. |
| 7,463,917 B2 | 12/2008 | Martinez |
| 7,631,015 B2 | 12/2009 | Gupta et al. |
| 7,805,196 B2 | 9/2010 | Miesel et al. |
| 7,881,798 B2 | 2/2011 | Miesel et al. |
| 8,055,348 B2 | 11/2011 | Heruth et al. |
| 2001/0051819 A1 | 12/2001 | Fischell et al. |
| 2001/0056290 A1 | 12/2001 | Fischell et al. |
| 2002/0002390 A1 | 1/2002 | Fischell et al. |
| 2002/0035338 A1 | 3/2002 | Dear et al. |
| 2002/0054694 A1 | 5/2002 | Vachtsevanos et al. |
| 2002/0072770 A1 | 6/2002 | Pless |
| 2002/0072776 A1 | 6/2002 | Osorio et al. |
| 2002/0072782 A1 | 6/2002 | Osorio et al. |
| 2002/0077670 A1 | 6/2002 | Archer et al. |
| 2002/0095099 A1 | 7/2002 | Quyen et al. |
| 2002/0099412 A1 | 7/2002 | Fischell et al. |
| 2002/0103512 A1* | 8/2002 | Echauz et al. .......... 607/9 |
| 2002/0109621 A1 | 8/2002 | Khair et al. |
| 2002/0111542 A1 | 8/2002 | Warkentin et al. |
| 2002/0116042 A1 | 8/2002 | Boling |
| 2002/0126036 A1 | 9/2002 | Flaherty et al. |
| 2002/0147388 A1 | 10/2002 | Mass et al. |
| 2002/0169485 A1 | 11/2002 | Pless et al. |
| 2002/0177882 A1 | 11/2002 | DiLorenzo |
| 2002/0188330 A1 | 12/2002 | Gielen et al. |
| 2003/0004428 A1 | 1/2003 | Pless |
| 2003/0009207 A1 | 1/2003 | Paspa et al. |
| 2003/0013981 A1 | 1/2003 | Gevins et al. |
| 2003/0018367 A1 | 1/2003 | DiLorenzo |
| 2003/0028072 A1 | 2/2003 | Fischell et al. |
| 2003/0050549 A1 | 3/2003 | Sochor |
| 2003/0050730 A1 | 3/2003 | Greeven et al. |
| 2003/0073917 A1 | 4/2003 | Echauz et al. |
| 2003/0074033 A1 | 4/2003 | Pless et al. |
| 2003/0083716 A1 | 5/2003 | Nicolelis et al. |
| 2003/0114886 A1 | 6/2003 | Gluckman et al. |
| 2003/0144709 A1 | 7/2003 | Zabara et al. |
| 2003/0144711 A1 | 7/2003 | Pless et al. |
| 2003/0144829 A1 | 7/2003 | Geatz et al. |
| 2003/0149457 A1 | 8/2003 | Tcheng et al. |
| 2003/0158587 A1 | 8/2003 | Esteller et al. |
| 2003/0167078 A1 | 9/2003 | Weisner et al. |
| 2003/0174554 A1 | 9/2003 | Dunstone et al. |
| 2003/0176806 A1 | 9/2003 | Pineda et al. |
| 2003/0181955 A1 | 9/2003 | Gielen |
| 2003/0187621 A1 | 10/2003 | Nikitin et al. |
| 2003/0195574 A1 | 10/2003 | Osorio et al. |
| 2003/0195588 A1 | 10/2003 | Fischell et al. |
| 2003/0195602 A1 | 10/2003 | Boling |
| 2004/0034368 A1 | 2/2004 | Pless et al. |
| 2004/0039427 A1 | 2/2004 | Barrett et al. |
| 2004/0039981 A1 | 2/2004 | Riedl et al. |
| 2004/0054297 A1 | 3/2004 | Wingeier et al. |
| 2004/0059761 A1 | 3/2004 | Hively |
| 2004/0068199 A1 | 4/2004 | Echauz et al. |
| 2004/0073273 A1 | 4/2004 | Gluckman et al. |
| 2004/0077995 A1 | 4/2004 | Ferek-Petric |
| 2004/0078160 A1 | 4/2004 | Frei et al. |
| 2004/0082984 A1 | 4/2004 | Osorio et al. |
| 2004/0087835 A1 | 5/2004 | Hively |
| 2004/0097802 A1 | 5/2004 | Cohen |
| 2004/0122281 A1 | 6/2004 | Fischell et al. |
| 2004/0122335 A1 | 6/2004 | Sackellares et al. |
| 2004/0127810 A1 | 7/2004 | Sackellares et al. |
| 2004/0133119 A1 | 7/2004 | Osorio et al. |
| 2004/0133248 A1 | 7/2004 | Frei et al. |
| 2004/0133390 A1 | 7/2004 | Osorio et al. |
| 2004/0138516 A1 | 7/2004 | Osorio et al. |
| 2004/0138517 A1 | 7/2004 | Osorio et al. |
| 2004/0138536 A1 | 7/2004 | Frei et al. |
| 2004/0138578 A1 | 7/2004 | Pineda et al. |
| 2004/0138579 A1 | 7/2004 | Deadwyler et al. |
| 2004/0138580 A1 | 7/2004 | Frei et al. |
| 2004/0138581 A1 | 7/2004 | Frei et al. |
| 2004/0138647 A1 | 7/2004 | Osorio et al. |
| 2004/0138711 A1 | 7/2004 | Osorio et al. |
| 2004/0138721 A1 | 7/2004 | Osorio et al. |
| 2004/0147969 A1 | 7/2004 | Mann et al. |
| 2004/0152958 A1 | 8/2004 | Frei et al. |
| 2004/0153129 A1 | 8/2004 | Pless et al. |
| 2004/0158119 A1 | 8/2004 | Osorio et al. |
| 2004/0172089 A1 | 9/2004 | Whitehurst et al. |
| 2004/0176359 A1 | 9/2004 | Wermeling |
| 2004/0181263 A1 | 9/2004 | Balzer et al. |
| 2004/0199212 A1 | 10/2004 | Fischell |
| 2004/0210269 A1 | 10/2004 | Shalev et al. |
| 2004/0243146 A1 | 12/2004 | Chesbrough et al. |
| 2004/0267152 A1 | 12/2004 | Pineda et al. |
| 2005/0004621 A1 | 1/2005 | Boveja et al. |
| 2005/0010261 A1 | 1/2005 | Luders et al. |
| 2005/0015128 A1 | 1/2005 | Rezai et al. |
| 2005/0015129 A1 | 1/2005 | Mische |
| 2005/0021103 A1 | 1/2005 | DiLorenzo |
| 2005/0021104 A1 | 1/2005 | DiLorenzo |
| 2005/0021105 A1 | 1/2005 | Firlik et al. |
| 2005/0021313 A1 | 1/2005 | Nikitin et al. |
| 2005/0027328 A1 | 2/2005 | Greenstein |
| 2005/0033369 A1 | 2/2005 | Badelt |
| 2005/0043772 A1 | 2/2005 | Stahmann et al. |
| 2005/0043774 A1 | 2/2005 | Devlin et al. |
| 2005/0049649 A1 | 3/2005 | Luders et al. |
| 2005/0059867 A1 | 3/2005 | Cheng |
| 2005/0070970 A1 | 3/2005 | Knudson et al. |
| 2005/0075067 A1 | 4/2005 | Lawson et al. |
| 2005/0096710 A1 | 5/2005 | Kieval |
| 2005/0113885 A1 | 5/2005 | Haubrich et al. |
| 2005/0119703 A1 | 6/2005 | DiLorenzo |
| 2005/0124863 A1 | 6/2005 | Cook |
| 2005/0131493 A1 | 6/2005 | Boveja et al. |
| 2005/0137640 A1 | 6/2005 | Freeberg et al. |
| 2005/0143786 A1 | 6/2005 | Boveja |
| 2005/0143787 A1 | 6/2005 | Boveja et al. |
| 2005/0149123 A1 | 7/2005 | Lesser et al. |
| 2005/0182308 A1 | 8/2005 | Bardy |
| 2005/0182464 A1 | 8/2005 | Schulte et al. |
| 2005/0187789 A1 | 8/2005 | Hatlestad |
| 2005/0197590 A1 | 9/2005 | Osorio et al. |
| 2005/0203584 A1 | 9/2005 | Twetan et al. |
| 2005/0209218 A1 | 9/2005 | Meyerson et al. |
| 2005/0222503 A1 | 10/2005 | Dunlop et al. |
| 2005/0222626 A1 | 10/2005 | DiLorenzo |
| 2005/0222641 A1 | 10/2005 | Pless |
| 2005/0228249 A1 | 10/2005 | Boling |
| 2005/0228461 A1 | 10/2005 | Osorio et al. |
| 2005/0231374 A1 | 10/2005 | Diem et al. |
| 2005/0234355 A1 | 10/2005 | Rowlandson |
| 2005/0240242 A1 | 10/2005 | DiLorenzo |
| 2005/0240245 A1 | 10/2005 | Bange et al. |
| 2005/0245970 A1 | 11/2005 | Erickson et al. |
| 2005/0245984 A1 | 11/2005 | Singhal et al. |
| 2005/0266301 A1 | 12/2005 | Smith et al. |
| 2005/0277844 A1 | 12/2005 | Strother |
| 2006/0015034 A1 | 1/2006 | Martinerie et al. |
| 2006/0015153 A1 | 1/2006 | Gliner et al. |
| 2006/0094970 A1 | 5/2006 | Drew |
| 2006/0111644 A1 | 5/2006 | Guttag et al. |
| 2006/0122469 A1 | 6/2006 | Martel |
| 2006/0129056 A1 | 6/2006 | Leuthardt et al. |
| 2006/0142822 A1 | 6/2006 | Tulgar |
| 2006/0173259 A1 | 8/2006 | Flaherty et al. |
| 2006/0173510 A1 | 8/2006 | Besio et al. |
| 2006/0200038 A1 | 9/2006 | Savit et al. |
| 2006/0212092 A1 | 9/2006 | Pless et al. |
| 2006/0212093 A1 | 9/2006 | Pless et al. |
| 2006/0253096 A1 | 11/2006 | Blakley et al. |
| 2006/0293578 A1 | 12/2006 | Rennaker, II |
| 2007/0027367 A1 | 2/2007 | Oliver et al. |
| 2007/0027514 A1 | 2/2007 | Gerber |
| 2007/0043459 A1 | 2/2007 | Abbott, III et al. |
| 2007/0055320 A1 | 3/2007 | Weinand |
| 2007/0060973 A1 | 3/2007 | Ludvig et al. |
| 2007/0073355 A1 | 3/2007 | DiLorenzo |

(56) References Cited

U.S. PATENT DOCUMENTS

| | | | |
|---|---|---|---|
| 2007/0100398 A1 | 5/2007 | Sloan | |
| 2007/0161919 A1 | 7/2007 | DiLorenzo | |
| 2007/0162086 A1 | 7/2007 | DiLorenzo | |
| 2007/0167991 A1 | 7/2007 | DiLorenzo | |
| 2007/0238939 A1 | 10/2007 | Giftakis et al. | |
| 2007/0250077 A1 | 10/2007 | Skakoon et al. | |
| 2008/0161712 A1 | 7/2008 | Leyde | |
| 2008/0161713 A1 | 7/2008 | Leyde et al. | |
| 2008/0319281 A1 | 12/2008 | Aarts | |
| 2009/0264952 A1 | 10/2009 | Jassemidis et al. | |
| 2010/0023089 A1 | 1/2010 | DiLorenzo | |
| 2010/0217348 A1 | 8/2010 | DiLorenzo | |
| 2011/0319785 A1 | 12/2011 | Snyder et al. | |

FOREIGN PATENT DOCUMENTS

| | | |
|---|---|---|
| CA | 2428116 | 5/2002 |
| CA | 2428383 | 5/2002 |
| CA | 2425122 | 6/2002 |
| CA | 2425004 | 8/2002 |
| CA | 2456443 | 1/2003 |
| CA | 2491987 | 1/2004 |
| DE | 69832022D | 12/2005 |
| EP | 0124663 A1 | 11/1984 |
| EP | 0898460 | 3/1999 |
| EP | 1017313 | 7/2000 |
| EP | 1107693 | 6/2001 |
| EP | 1145735 A2 | 10/2001 |
| EP | 1145736 A2 | 10/2001 |
| EP | 1292900 | 3/2003 |
| EP | 1307260 | 5/2003 |
| EP | 1331967 | 8/2003 |
| EP | 1335668 | 8/2003 |
| EP | 1341580 | 9/2003 |
| EP | 1404216 | 4/2004 |
| EP | 1333753 | 9/2004 |
| EP | 1525551 | 4/2005 |
| EP | 1558121 | 8/2005 |
| EP | 1558128 | 8/2005 |
| EP | 1558130 | 8/2005 |
| EP | 1558131 | 8/2005 |
| EP | 1558132 | 8/2005 |
| EP | 1558330 | 8/2005 |
| EP | 1558334 | 8/2005 |
| EP | 1562674 | 8/2005 |
| EP | 0911061 B1 | 10/2005 |
| EP | 1609414 A2 | 12/2005 |
| JP | 24033673 A2 | 2/2004 |
| SU | 1074484 | 2/1984 |
| WO | WO 85/01213 A1 | 3/1985 |
| WO | WO 92/00119 A1 | 1/1992 |
| WO | WO 97/26823 A1 | 7/1997 |
| WO | WO 97/34522 A1 | 9/1997 |
| WO | WO 97/34524 A1 | 9/1997 |
| WO | WO 97/34525 A1 | 9/1997 |
| WO | WO 97/39797 A1 | 10/1997 |
| WO | WO 97/42990 A1 | 11/1997 |
| WO | WO 97/45160 A1 | 12/1997 |
| WO | WO 98/49935 A1 | 11/1998 |
| WO | WO 99/20342 A1 | 4/1999 |
| WO | WO 99/56821 A1 | 11/1999 |
| WO | WO 99/56822 A1 | 11/1999 |
| WO | WO 00/07494 A2 | 2/2000 |
| WO | WO 00/10455 | 3/2000 |
| WO | WO 01/41867 A1 | 6/2001 |
| WO | WO 01/48676 A1 | 7/2001 |
| WO | WO 01/49364 A2 | 7/2001 |
| WO | WO 01/67288 A2 | 9/2001 |
| WO | WO 01/75660 A1 | 10/2001 |
| WO | WO 02/09610 A1 | 2/2002 |
| WO | WO 02/09811 A1 | 2/2002 |
| WO | WO 02/36003 A1 | 5/2002 |
| WO | WO 02/38031 A2 | 5/2002 |
| WO | WO 02/38217 A2 | 5/2002 |
| WO | WO 02/49500 A2 | 6/2002 |
| WO | WO 02/058536 A2 | 8/2002 |
| WO | WO 02/067122 A1 | 8/2002 |
| WO | WO 03/001996 A2 | 1/2003 |
| WO | WO 03/009207 A1 | 1/2003 |
| WO | WO 03/030734 A2 | 4/2003 |
| WO | WO 03/035165 A1 | 5/2003 |
| WO | WO 03/084605 A1 | 10/2003 |
| WO | WO 2004/008373 A2 | 1/2004 |
| WO | WO 2004/032720 A2 | 4/2004 |
| WO | WO 2004/034231 A2 | 4/2004 |
| WO | WO 2004/034879 A2 | 4/2004 |
| WO | WO 2004/034880 A2 | 4/2004 |
| WO | WO 2004/034881 A2 | 4/2004 |
| WO | WO 2004/034882 A2 | 4/2004 |
| WO | WO 2004/034883 A2 | 4/2004 |
| WO | WO 2004/034885 A2 | 4/2004 |
| WO | WO 2004/034982 A2 | 4/2004 |
| WO | WO 2004/034997 A2 | 4/2004 |
| WO | WO 2004/034998 A2 | 4/2004 |
| WO | WO 2004/035130 A2 | 4/2004 |
| WO | WO 2004/036370 A2 | 4/2004 |
| WO | WO 2004/036372 A2 | 4/2004 |
| WO | WO 2004/036376 A2 | 4/2004 |
| WO | WO 2004/036377 A2 | 4/2004 |
| WO | WO 2004/037342 A2 | 5/2004 |
| WO | WO 2004/043536 A1 | 5/2004 |
| WO | WO 2004/091718 A1 | 10/2004 |
| WO | WO 2005/007236 A2 | 1/2005 |
| WO | WO 2005/028026 A1 | 3/2005 |
| WO | WO 2005/028028 A1 | 3/2005 |
| WO | WO 2005/031630 A2 | 4/2005 |
| WO | WO 2005/051167 A1 | 6/2005 |
| WO | WO 2005/051306 A2 | 6/2005 |
| WO | WO 2005/117693 A1 | 12/2005 |
| WO | WO 2006/014971 A2 | 2/2006 |
| WO | WO 2006/014972 A2 | 2/2006 |
| WO | WO2006/035392 A1 | 4/2006 |

OTHER PUBLICATIONS

Leyde et al.; U.S. Appl. No. 12/020,507 entitled "Methods and systems for measuring a subject's susceptibility to a seizure," filed Jan. 25, 2008.

Snyder et al.; U.S. Appl. No.12/020,450 entitled "Systems and methods for identifying a contra-ictal condition in a subject," filed Jan. 25, 2008.

Snyder et al.; U.S. Appl. No. 12/035,335 entitled "Methods and systems for characterizing and generating a patient-specific seizure prediction system," filed Feb. 21, 2008.

Leyde et al.; U.S. Appl. No. 12/343,376 entitled "Systems and method for recording clinical manifestations of a seizure," filed Dec. 23, 2008.

Brown et al.; U.S. Appl. No. 12/343,386 entitled "Housing for an implantable medical device," filed Dec. 23, 2008.

Gardner, A. B. A Novelty Detection Approach to Seizure Analysis from Intracranial EEG. Georgia Insititute of Technology. Apr. 2004. A disertation available at http://etd.gatech.edu/theses/available/etd-04122004-132404/unrestricted/gardner_andrew_b_200405_phd.pdf. Accessed Feb. 28, 2006.

Geva, et al. Forecasting generalized epileptic seizures from the EEG signal by wavelet analysis and dynamic unsupervised fuzzy clustering. IEEE Trans. Biomed. Eng. 1998; 45(10): 1205-16.

Gigola, et al. Prediction of epileptic seizures using accumulated energy in a multiresolution framework. J. Neurosci. Methods. 2004; 138(1-2): 107-111.

Guyon, I. An introduction to variable and feature selection. Journal of Machine Learning Research. 2003; 3:1157-1182.

Guyon, I. Multivariate Non-Linear Feature Selection with Kernel Multiplicative Updates and Gram-Schmidt Relief. BISC FLINT-CIBI 2003 Workshop. Berkeley. 2003; p. 1-11.

Harrison, et al. Accumulated energy revised. Clin. Neurophysiol. 2005; 116(3):527-31.

Harrison, et al. Correlation dimension and integral do not predict epileptic seizures. Chaos. 2005; 15(3): 33106-1-15.

(56) References Cited

OTHER PUBLICATIONS

Hearst M. Trends & Controversies: Support Vector Machines. IEEE Intelligent Systems. 1998; 13: 18-28.

Hively, et al. Channel-consistent forewarning of epileptic events from scalp EEG. IEEE Trans. Biomed. Eng. 2003; 50(5): 584-93.

Hively, et al. Detecting dynamical changes in nonlinear time series. Physics Letters A. 1999; 258: 103-114.

Hively, et al. Epileptic Seizure Forewarning by Nonlinear Techniques. *ORNL/TM-2000/333 Oak Ridge National Laboratory*. Nov. 2000. Available at http://computing.oml.gov/cse_home/staff/hively/NBICradaAnnualRptFY00.pdf. Accessed Feb. 28, 2006.

Hjorth, B. Source derivation simplifies topographical EEG interpretation. Am. J. EEG Technol. 1980; 20: 121-132.

Hsu, et al. A practical guide to support vector classification. Technical report, Department of Computer Science and Information Technology, National Taiwan University, 2003. Available at http://www.csie.ntu.edu.tw/~cjlin/papers/guide/guide.pdf. Accessed Feb. 28, 2006.

Huynh, J. A. Evaluation of Gene Selection Using Support Vector Machine Recursive Feature Elimination. Arizona State University. May 26, 2004. (28 pages).

Huynh, J. A. Evaluation of Gene Selection Using Support Vector Machine Recursive Feature Elimination. Presentation slides. (41 pages) (May 26, 2004).

Iasemidis, et al. Adaptive epileptic seizure prediction system. IEEE Trans. Biomed. Eng. 2003; 50(5):616-27.

Iasemidis, et al. Automated Seizure Prediction Paradigm. Epilepsia. 1998; vol. 39, pp. 56.

Iasemidis, et al. Chaos Theory and Epilepsy. *The Neuroscientist*. 1996; 2:118-126.

Iasemidis, et al. Comment on "Inability of lyapunov exponents to predict epileptic seaizures." Physical Review Letters. 2005; 94(1):019801-1.

Iasemidis, et al. Detection of the Preictal Transition State in Scalp-Sphenoidal EEG Recordings. American Clinical Neurophysiology Society Annual Meeting, Sep. 1996. pp. C206.

Iasemidis, et al. Dynamical Interaction of the Epileptogenic Focus with Extrafocal Sites in Temporal Lobe Epilepsy (TLE). Ann. Neurol.1997; 42, pp. 429. pp. M146.

Iasemidis, et al. Epileptogenic Focus Localization by Dynamical Analysis of Interictal Periods of EEG in Patients with Temporal Lobe Epilepsy. Epilepsia. 1997; 38, suppl. 8, pp. 213.

Iasemidis, et al. Localizing Preictal Temporal Lobe Spike Foci Using Phase Space Analysis. Electroencephalography and Clinical Neurophysiology. 1990; 75, pp. S63-S64.

Iasemidis, et al. Long-term prospective on-line real-time seizure prediction. Clin. Neurophysiol. 2005; 116(3):532-44.

Iasemidis, et al. Long-Time-Scale Temporo-spatial Patterns of Entrainment of Preictal Electrocorticographic Data in Human Temporal Lobe Epilepsy. Epilepsia. 1990; 31(5):621.

Iasemidis, et al. Measurement and Quantification of Spatio-Temporal Dynamics of Human Epileptic Seizures. In: Nonlinear Signal Processing in Medicine, Ed. M. Akay, IEEE Press. 1999; pp. 1-27.

Iasemidis, et al. Modelling of ECoG in temporal lobe epilepsy. Biomed. Sci. Instrum. 1988; 24: 187-93.

• Iasemidis, et al. Nonlinear Dynamics of EcoG Data in Temporal Lobe Epilepsy. Electroencephalography and Clinical Neurophysiology. 1998; 5, pp. 339.

Iasemidis, et al. Phase space topography and the Lyapunov exponent of electrocorticograms in partial seizures. Brain Topogr. 1990; 2(3): 187-201.

Iasemidis, et al. Preictal Entrainment of a Critical Cortical Mass is a Necessary Condition for Seizure Occurrence. Epilepsia. 1996; 37, suppl. 5. pp. 90.

Iasemidis, et al. Preictal-Postictal Versus Postictal Analysis for Epileptogenic Focus Localization. J. Clin. Neurophysiol. 1997; 14, pp. 144.

Iasemidis, et al. Quadratic binary programming and dynamic system approach to determine the predictability of epileptic seizures. *Journal of Combinatorial Optimization*. 2001; 5: 9-26.

Iasemidis, et al. Quantification of Hidden Time Dependencies in the EEG within the Framework of Non-Linear Dynamics. World Scientific. 1993; pp. 30-47.

Iasemidis, et al. Spatiotemporal dynamics of human epileptic seizures. World Scientific. 1996; pp. 26-30.

Iasemidis, et al. Spatiotemporal Evolution of Dynamical Measures Precedes Onset of Mesial Temporal Lobe Seizures. Epilepsia. 1994; 358, pp. 133.

Iasemidis, et al. Spatiotemporal Transition to Epileptic Seizures: A Nonlinear Dynamical Analysis of Scalp and Intracranial EEG Recordings. (In Silva, F.L. Spatiotemporal Models in Biological and Artifical Systems. Ohmsha IOS Press. 1997; 37, pp. 81-88.).

Iasemidis, et al. The evolution with time of the spatial distribution of the largest lyapunov exponent on the human epileptic cortex. World Scientific. 1991; pp. 49-82.

Iasemidis, et al. The Use of Dynamical Analysis of EEG Frequency Content in Seizure Prediction. American Electroencephalographic Society Annual Meeting, Oct. 1993.

Iasemidis, et al. Time Dependencies in Partial Epilepsy. 1993; 34, pp. 130-131.

Iasemidis, et al. Time dependencies in the occurrences of epileptic seizures. Epilepsy Res. 1994; 17(1): 81-94.

Iasemidis, L. D. Epileptic seizure prediction and control. IEEE Trans. Biomed. Eng. 2003; 50(5):549-58.

Jerger, et al. Early seizure detection. Journal of Clin. Neurophysiol. 2001; 18(3):259-68.

Jerger, et al. Multivariate linear discrimination of seizures. Clin. Neurophysiol. 2005; 116(3):545-51.

Jouny, et al. Characterization of epileptic seizure dynamics using Gabor atom density. Clin. Neurophysiol. 2003; 114(3):426-37.

Latka, et al. Wavelet analysis of epileptic spikes. Phys. Rev. E. 2003; 67(5 Pt 1):052902 (6 pages).

Le Van Quyen, et al. Anticipating epileptic seizures in real time by a non-linear analysis of similarity between EEG recordings. Neuroreport. 1999; 10(10):2149-55.

Le Van Quyen, et al. Author's second reply. The Lancet. 2003; 361:971.

Le Van Quyen, et al. Comparison of Hilbert transform and wavelet methods for the analysis of neuronal synchrony. J. Neurosci. Methods. 2001; 111(2):83-98.

Le Van Quyen, et al. Nonlinear analyses of interictal EEG map the brain interdependences in human focal epilepsy. Physica D. 1999; 127:250-266.

Le Van Quyen, et al. Preictal state identification by synchronization changes in long-term intracranial EEG recordings. Clin. Neurophysiol. 2005; 116(3):559-68.

Le Van Quyen, M. Anticipating epileptic seizures: from mathematics to clinical applications. C. R. Biol. 2005; 328(2):187-98.

Lehnertz, et al. Nonlinear EEG analysis in epilepsy: its possible use for interictal focus localization, seizure anticipation, and prevention. J. Clin. Neurophysiol. 2001; 18(3):209-22.

Lehnertz, et al. Seizure prediction by nonlinear EEG analysis. IEEE Eng. Med. Biol. Mag. 2003; 22(1):57-63.

Lehnertz, et al. The First International Collaborative Workshop on Seizure Prediction: summary and data description. Clin. Neurophysiol. 2005; 116(3):493-505.

Lehnertz, K. Non-linear time series analysis of intracranial EEG recordings in patients with epilepsy—an overview. Int. J. Psychophysiol. 1999; 34(1):45-52.

Nigam, et al. A neural-network-based detection of epilepsy. Neurological Research. 2004; 26(1):55-60.

Osorio, et al. Automated seizure abatement in humans using electrical stimulation. Ann. Neurol. 2005; 57(2):258-68.

Osorio, et al. Performance reassessment of a real-time seizure-detection algorithm on long ECoG series. Epilepsia. 2002; 43(12):1522-35.

Osorio, et al. Real-time automated detection and quantitative analysis of seizures and short-term prediction of clinical onset. Epilepsia. 1998; 39(6):615-27.

Ossadtchi, et al. Hidden Markov modelling of spike propagation from interictal MEG data. Phys. Med. Biol. 2005; 50(14):3447-69.

(56) References Cited

OTHER PUBLICATIONS

Pflieger, et al. A noninvasive method for analysis of epileptogenic brain connectivity. Presented at the American Epilepsy Society 2004 Annual Meeting, New Orleans. Dec. 6, 2004. Epilepsia. 2004; 45(Suppl. 7):70-71.

Pittman, V. Flexible Drug Dosing Produces Less Side-effects in People With Epilepsy. Dec. 29, 2005. Available at http://www.medicalnewstoday.com/medicalnews.php?newsid=35478. Accessed on Apr. 17, 2006.

Platt, et al. Large Margin DAGs for Multiclass Classification. S.A. Solla. T.K. Leen adn K. R. Muller (eds.). 2000; pp. 547-553.

Platt, J. C. Using Analytic QP and Sparseness to Speed Training of Support Vector Machines. Advances in Neural Information Processing Systems. 1999; 11:557-563.

Protopopescu, et al. Epileptic event forewarning from scalp EEG. J. Clin. Neurophysiol. 2001; 18(3):223-45.

Rahimi, et al. On the Effectiveness of Aluminium Foil Helmets: An Empirical Study. Available at http://people.csail.mit.edu/rahimi/helmet/. Accessed Mar. 2, 2006.

Tetzlaff, et al. Cellular neural networks (CNN) with linear weight functions for a prediction of epileptic seizures. Int'l. J. of Neural Systems. 2003; 13(6):489-498.

Theiler, et al. Testing for non-linearity in time series: the method of surrogate data. Physica D. 1992; 58:77-94.

Tsakalis, K. S. Prediction and control of epileptic seizures: Coupled oscillator models. Arizona State University. (Slide: 53 pages) (No date).

Van Drongelen, et al. Seizure anticipation in pediatric epilepsy: use of Kolmogorov entropy. Pediatr. Neurol. 2003; 29(3): 207-13.

Van Putten, M. Nearest neighbor phase synchronization as a measure to detect seizure activity from scalp EEG recordings. J. Clin. Neurophysiol. 2003; 20(5):320-5.

Venugopal, et al. A new approach towards predictability of epileptic seizures: KLT dimension. Biomed Sci. Instrum. 2003; 39:123-8.

Vonck, et al. Long-term amygdalohippocampal stimulation for refractory temporal lobe epilepsy. Ann. Neurol. 2002; 52(5):556-65.

Vonck, et al. Long-term deep brain stimulation for refractory temporal lobe epilepsy. Epilepsia. 2005; 46(Suppl 5):98-9.

Vonck, et al. Neurostimulation for refractory epilepsy. Acta. Neurol. Belg. 2003; 103(4):213-7.

Weiss, P. Seizure prelude found by chaos calculation. Science News. 1998; 153(20):326.

Wells, R. B. Spatio-Temporal Binding and Dynamic Cortical Organization: Research Issues. Mar. 2005. Available at http://www.mrc.uidaho.edu/~rwells/techdocs/Functional%20Column%20Research%20Issues.pdf. Accessed Mar. 2, 2006.

Widman, et al. Reduced signal complexity of intracellular recordings: a precursor for epileptiform activity? Brain Res. 1999; 836(1-2):156-63.

Winterhalder, et al. Sensitivity and specificity of coherence and phase synchronization analysis. (In Press) Phys. Lett. A. 2006.

Winterhalder, et al. The seizure prediction characteristic: a general framework to assess and compare seizure prediction methods. Epilepsy Behav. 2003; 4(3):318-25.

Yang, et al. A supervised feature subset selection technique for multivariate time series. Available at http://infolab.usc.edu/DocsDemos/fsdm05.pdf. Accessed Mar. 2, 2006.

Yang, et al. CLe Ver: A feature subset selection technique for multivariate time series. T. B. Ho, D. Cheung, and H. Liu (Eds.): Pakdd. 2005; LNAI 3518: 516-522.

Yang, et al. Relation between Responsiveness to Neurotransmitters and Complexity of Epileptiform Activity in Rat Hippocampal CA1 Neurons. Epilepsia. 2002; 43(11):1330-1336.

Yatsenko, et al. Geometric Models, Fiber Bundles, and Biomedical Applications. Proceedings of Institute of Mathematics of NAS of Ukraine. 2004; 50 (Part 3):1518-1525.

Zaveri et al. Time-Frequency Analyses of Nonstationary Brain Signals. Electroencephalography and Clinical Neurophysiology. 1991; 79, pp. 28P-29P.

Zhang, et al. High-resolution EEG: cortical potential imaging of interictal spikes. Clin. Neurophysiol. 2003; 114(10):1963-73.

Adjouadi, et al. A new mathematical approach based on orthogonal operators for the detection of interictal spikes in epileptogenic data. *Biomed. Sci. Instrum*. 2004; 40: 175-80.

Adjouadi, et al. Detection of interictal spikes and artifactual data through orthogonal transformations. J. Clin. Neurophysiol. 2005; 22(1):53-64.

Adjouadi, et al. Interictal spike detection using the Walsh transform. IEEE Trans. Biomed. Eng. 2004; 51(5): 868-72.

Aksenova, et al. Nonparametric on-line detection of changes in singnal spectral characteristics for early prediction of epilepsy seizure onset. J. Automation and Information Sciences. 2004; 36(8): 35-45.

Aksenova, et al. On-line disharmony detection for early prediction of epilepsy seizure onset. 5th International Workshop Neural Coding 2003. Aulla (Italy) Sep. 20-25, 2003. (Abstract).

Andrzejak, et al. Bivariate surrogate techniques: necessity, strengths, and caveats. Physical Review E. 2003; 68: 066202-1-066202-15.

Andrzejak, et al. Testing the null hypothesis of the nonexistence of a preseizure state. Physical Review E. 2003; 67: 010901-1-010901-4.

Aschenbrenner-Scheibe, et al. How well can epileptic seizures be predicted? An evaluation of a nonlinear method. Brain. 2003; 126: 2616-26.

Bangham et al. Diffusion of univalent ions across the lamellae of swollen phospholipids. 1965. *J Moi. Biol*. 13: 238-252.

Baruchi, et al. Functional holography of complex networks activity—From cultures to the human brain. Complexity. 2005; 10(3): 38-51.

Baruchi, et al. Functional holography of recorded neuronal networks activity. Neuroinformatics. 2004; 2(3): 333-51.

Ben-Hur, et al. Detecting stable clusters using principal component analysis. Methods Mol. Biol. 2003; 224: 159-82.

Bergey, et al. Epileptic seizures are characterized by changing signal complexity. Clin. Neurophysiol. 2001; 112(2): 241-9.

Betterton, et al. Determining State of Consciousness from the Intracranial Electroencephalogram (IEEG) for Seizure Prediction. From Proceeding (377) Modelling, Identification, and Control. 2003; 377-201: 313-317.

Bhattacharya, et al. Enhanced phase synchrony in the electroencephalograph gamma band for musicians while listening to music. Phys. Rev. E. 2001; 64:012902-1-4.

Boley, et al. Training Support Vector Machine using Adaptive Clustering. 2004 SIAM International Conference on Data Mining, Apr. 22-24, 2004. Lake Buena Vista, FL, USA. 12 pages.

Burges, C. A Tutorial on Support Vector Machines for Pattern Recognition. Data Mining and Knowledge Discovery. 1998; 2: 121-167.

Cao, et al. Detecting dynamical changes in time series using the permutation entropy. Physical Review E. 2004; 70:046217-1-046217-7.

Carretero-Gonzalez, et al. Scaling and interleaving of subsystem Lyapunov exponents for spatio-temporal systems. Chaos. 1999; 9(2): 466-482.

Casdagli, et al. Characterizing nonlinearity in invasive EEG recordings from temporal lobe epilepsy. Physica D. 1996; 99 (2/3): 381-399.

Casdagli, et al. Nonlinear Analysis of Mesial Temporal Lobe Seizures Using a Surrogate Data Technique. Epilepsia. 1995; 36, suppl. 4, pp. 142.

Casdagli, et al. Non-linearity in invasive EEG recordings from patients with temporal lobe epilepsy. Electroencephalogr. Clin. Neurophysiol. 1997; 102(2): 98-105.

Cerf, et al. Criticality and synchrony of fluctuations in rhythmical brain activity: pretransitional effects in epileptic patients. Biol. Cybern. 2004; 90(4): 239-55.

Chaovalitwongse, et al. EEG Classification in Epilepsy. Annals. 2004; 2(37): 1-31.

Chaovalitwongse, et al. Performance of a seizure warning algorithm based on the dynamics of intracranial EEG. Epilepsy Res. 2005; 64(3): 93-113.

Chavez, et al. Spatio-temporal dynamics prior to neocortical seizures: amplitude versus phase couplings. IEEE Trans. Biomed. Eng. 2003; 50(5):571-83.

(56) References Cited

OTHER PUBLICATIONS

Crichton, Michael, "Terminal Man", 1972, Ballantine Books, NY, NY, pp. 21-24, 32-33, 70-71, and 74-81.
D'Alessandro, et al. Epileptic seizure prediction using hybrid feature selection over multiple intracranial EEG electrode contacts:a report of four patients. IEEE Trans. Biomed. Eng. 2003; 50(5): 603-15.
D'Alessandro, et al. A multi-feature and multi-channel univariate selection process for seizure prediction. Clin. Neurophysiol. 2005; 116(3): 506-16.
Drury, et al. Seizure prediction using scalp electroencephalogram. Exp. Neurol. 2003; 184 Suppl 1: S9-18.
Ebersole, J. S. Functional neuroimaging with EEG source models to localize epileptogenic foci noninvasively. Neurology. Available at http://www.uchospitals.edu/pdf/uch_001471.pdf. Accessed Feb. 28, 2006.
Ebersole, J. S. In search of seizure prediction: a critique. Clin. Neurophysiol. 2005; 116(3): 489-92.
Elbert et al. Chaos and Physiology: Deterministic Chaos in Excitable Cell Assemblies. Physiological Reviews. 1994; 74(1):1-47.
Elger, et al. Nonlinear EEG analysis and its potential role in epileptology. Epilepsia. 2000; 41 Suppl 3: S34-8.
Elger, et al. Seizure prediction by non-linear time series analysis of brain electrical activity. Eur. J. Neurosci. 1998; 10(2): 786-789.
Esteller, et al. A Comparison of Waveform Fractal Dimension Algorithms. IEEE Transactions on Circuits and Systems. 2001; vol. 48(2): 177-183.
Esteller, et al. Continuous energy variation during the seizure cycle: towards an on-line accumulated energy. Clin. Neurophysiol. 2005; 116(3): 517-26.
Esteller, et al. Feature Parameter Optimization for Seizure Detection/prediction. *Proceedings of the 23rd Annual International Conference of the IEEE Engineering in Medicine and Biology Society*, Istanbul, Turkey. Oct. 2001.
Faul, et al. An evaluation of automated neonatal seizure detection methods. Clin. Neurophysiol. 2005; 116(7): 1533-41.
Fein, et al. Common reference coherence data are confounded by power and phase effects. Electroencephalogr. Clin. Neurophysiol. 1988; 69:581-584.
Fell, et al. Linear inverse filtering improves spatial separation of nonlinear brain dynamics: a simulation study. J. Neurosci. Methods. 2000; 98(1): 49-56.
Firpi, et al. Epileptic seizure detection by means of genetically programmed artificial features. GECCO 2005: Proceedings of the 2005 conference on Genetic and evolutionary computation, vol. 1, pp. 461-466, Washington DC, USA, 2005. ACM Press.
Fisher et al. 1999. Reassessment: Vagus nerve stimulation for epilepsy, A report of the therapeutics and technology assessment subcommittee of the American Academy of Neurology. *Neurology*.53: 666-669.
Jouny, et al. Signal complexity and synchrony of epileptic seizures: is there an identifiable preictal period? Clin. Neurophysiol. 2005; 116(3):552-8.
Kapiris, et al. Similarities in precursory features in seismic shocks and epileptic seizures. Europhys. Lett. 2005; 69(4):657-663.
Katz, et al. Does interictal spiking change prior to seizures? Electroencephalogr. Clin. Neurophysiol. 1991; 79(2):153-6.
Kerem, et al. Forecasting epilepsy from the heart rate signal. Med. Biol. Eng. Comput. 2005; 43(2):230-9.
Khalilov, et al. Epileptogenic actions of GABA and fast oscillations in the developing hippocampus. Neuron. 2005; 48(5):787-96.
Korn, et al. Is there chaos in the brain? II. Experimental evidence and related models. C. R. Biol. 2003; 326(9):787-840.
Kraskov, A. Synchronization and Interdependence Measures and Their Application to the Electroencephalogram of Epilepsy Patients and Clustering of Data. Available at http://www.kfa-juelich.de/nic-series/volume24/nic-series-band24.pdf. Accessed Apr. 17, 2006. (106 pages).
Kreuz, et al. Measure profile surrogates: a method to validate the performance of epileptic seizure prediction algorithms. Phys. Rev. E. 2004; 69(6 Pt 1):061915-1-9.

Lachaux, et al. Measuring phase synchrony in brain signals. Hum. Brain Mapp. 1999; 8(4):194-208.
Lai, et al. Controlled test for predictive power of Lyapunov exponents: their inability to predict epileptic seizures. Chaos. 2004; 14(3):630-42.
Lai, et al. Inability of Lyapunov exponents to predict epileptic seizures. Phys. Rev. Lett. 2003; 91(6):068102-1-4.
Lemos, et al. The weighted average reference montage. Electroencephalogr. Clin. Neurophysiol. 1991; 79(5):361-70.
Li, et al. Fractal spectral analysis of pre-epileptic seizures in terms of criticality. J. Neural Eng. 200; 2(2):11-6.
Li, et al. Linear and nonlinear measures and seizure anticipation in temporal lobe epilepsy. J. Comput. Neurosci. 2003; 15(3):335-45.
Li, et al. Non-linear, non-invasive method for seizure anticipation in focal epilepsy. Math. Biosci. 2003; 186(1):63-77.
Litt, et al. Prediction of epileptic seizures. Lancet Neurol. 2002; 1(1):22-30.
Litt, et al. Seizure prediction and the preseizure period. Curr. Opin. Neurol. 2002; 15(2):173-7.
Maiwald, et al. Comparison of three nonlinear seizure prediction methods by means of the seizure prediction characteristic. Physica D. 2004; 194:357-368.
Mangasarian, et al. Lagrangian Support Vector Machines. Journal of Machine Learning Research. 2001; 1:161-177.
Martinerie, et al. Epileptic seizures can be anticipated by non-linear analysis. Nat. Med. 1998; 4(10):1173-6.
McSharry, et al. Comparison of predictability of epileptic seizures by a linear and a nonlinear method. IEEE Trans. Biomed. Eng. 2003; 50(5):628-33.
McSharry, et al. Linear and non-linear methods for automatic seizure detection in scalp electro-encephalogram recordings. Med. Biol. Eng. Comput. 2002; 40(4):447-61.
McSharry, P. E. Detection of dynamical transitions in biomedical signals using nonlinear methods. Lecture Notes in Computer Science 2004; 3215:483-490.
Meng, et al. Gaussian mixture models of ECoG signal features for improved detection of epileptic seizures. Med. Eng. Phys. 2004; 26(5):379-93.
Mizuno-Matsumoto, et al. Wavelet-crosscorrelation analysis can help predict whether bursts of pulse stimulation will terminate afterdischarges. Clin. Neurophysiol. 2002; 113(1):33-42.
Mormann, et al. Automated detection of a preseizure state based on a decrease in synchronization in intracranial electroencephalogram recordings from epilepsy patients. Phys. Rev. E. 2003; 67(2 Pt 1):021912-1-10.
Mormann, et al. Epileptic seizures are preceded by a decrease in synchronization. Epilepsy Res. 2003; 53(3):173-85.
Mormann, et al. Mean phase coherence as a measure for phase synchronization and its application to the EEG of epilepsy patients. Physica D. 2000; 144:358-369.
Mormann, et al. On the predictability of epileptic seizures. Clin. Neurophysiol. 2005; 116(3):569-87.
Mormann, et al. Seizure anticipation: from algorithms to clinical practice. Curr. Opin. Neurol. 2006; 19(2):187-93.
Navarro, et al. Seizure anticipation in human neocortical partial epilepsy. Brain. 2002; 125:640-55.
Navarro, et al. Seizure anticipation: do mathematical measures correlate with video-EEG evaluation? Epilepsia. 2005; 46(3):385-96.
Niederhauser, et al. Detection of seizure precursors from depth-EEG using a sign periodogram transform. IEEE Trans. Biomed. Eng. 2003; 50(4):449-58.
Daniel John Dilorenzo, U.S. Appl. No. 10/858,899, entitled "Closed-loop feedback-driven neuromodulation," filed Jun. 1, 2004.
Daniel John Dilorenzo, et al., U.S. Appl. No. 11/159,842, entitled "Closed-loop feedback-driven neuromodulation," filed Jun. 22, 2005.
Daniel J. Dilorenzo, U.S. Appl. No. 11/234,873, entitled "Systems and methods for monitoring a patient's neurological disease state," filed Sep. 23, 2005.
Daniel J. Dilorenzo, U.S. Appl. No. 11/239,653, entitled "Systems and methods for monitoring a patien's neurological disease state," filed Sep. 28, 2005.

(56) References Cited

OTHER PUBLICATIONS

Daniel John Dilorenzo, U.S. Appl. No. 11/282,317 entitled "Closed-loop vagus nerve stimulation," filed Nov. 17, 2005.
Daniel J. Dilorenzo, et al., U.S. Appl. No. 11/321,898, entitled "Methods and systems for recommending an appropriate pharmacological treatment to a patient for managing epilepsy and other neurological disorders," filed Dec. 28, 2005.
Mike Bland, et al., U.S. Appl. No. 11/322,150, entitled "Systems and methods for characterizing a patient's propensity for a neurological event and for communicating with a pharmacological agent dispenser," filed Dec. 28, 2005.
Snyder et al.; U.S. Appl. No. 12/053,312 entitled "Implantable systems and methods for identifying a contra-ictal condition in a subject," filed Mar. 21, 2008.
DiLorenzo, Daniel, U.S. Appl. No. 11/706,630, entitled "Methods and systems for administering an appropriate pharmacological treatment to a patient for managing epilepsy and other neurological disorders," filed Feb. 14, 2007.
DiLorenzo, Daniel, U.S. Appl. No. 11/743,607, entitled "Controlling a Subject's Susceptibility to a Seizure," filed May 2, 2007.
DiLorenzo, Daniel, U.S. Appl. No. 11/743,611, entitled "Providing Output Indicative of Subject's Disease State," filed May 2, 2007.
Harris et al; U.S. Appl. No. 11/766,742, entitled "Minimally Invasive Monitoring Systems," filed Jun. 21, 2007.
Harris et al; U.S. Appl. No. 11/766,751, entitled "Minimally Invasive Monitoring Methods," filed Jun. 21, 2007.
Harris et al; U.S. Appl. No. 11/766,756, entitled "Methods and Systems for Facilitating Clinical Trials," filed Jun. 21, 2007.
Harris et al; U.S. Appl. No. 11/766,760, entitled "Minimally Invasive System for Selecting Patient-Specific Therapy Parameters," filed Jun. 21, 2007.
Harris et al; U.S. Appl. No. 11/766,761, entitled "Minimally Invasive Monitoring Systems for Monitoring a Patient's Propensity for a Neurological Event," filed Jun. 21, 2007.
Harris, John, U.S. Appl. No. 11/734,190, entitled "Methods and Template Assembly for Implanting an Electrode Array in a Patient," filed Apr. 11, 2007.
DiLorenzo, Daniel; U.S. Appl. No. 12/177,060 entitled "Closed-loop feedback-driven neuromodulation," filed Jul. 21, 2008.
Bland et al.; U.S. Appl. No. 12/180,996 entitled "Patient advisory device," filed Jul. 28, 2008.
Franaszczuk et al.; an autoregressive method for the measurement of synchronization of interictal and ictal EEG signals; Biological Cybernetics, vol. 81; No. 1; pp. 3-9; 1999.
Yang et al.; Testing whether a prediction scheme is better than guess; Ch. 14 in Quantitative Neuroscience: Models, Algorithms, Diagnostics, and Therapeutic Applications; pp. 252-262; 2004.
Rimes, David M.; U.S. Appl. No. 12/630,300 entitled "Universal Electrode Array for Monitoring Brain Activity," filed Dec. 3, 2009.
Rimes et al.; U.S. Appl. No. 12/646,783 entitled "Brain State Analysis Based on Select Seizure Onset Characteristics And Clinical Manifestations," filed Dec. 23, 2009.
Echauz et al.; U.S. Appl. No. 12/649,098 entitled "Processing for Multi-Channel Signals," filed Dec. 29, 2009.
Floyd et al.; U.S. Appl. No. 12/685,543 entitled "Medical Lead Termination Sleeve for Implantable Medical Devices," filed Jan. 11, 2010.
Harris et al.; U.S. Appl. No. 12/691,650 entitled "Minimally invasive system for selecting patient-specific therapy parameters," filed Jan. 21, 2010.
Himes et al.; U.S. Appl. No. 12/716,132 entitled "Displaying and Manipulating Brain Function Data Including Enhanced Data Scrolling Functionality," filed Mar. 2, 2010.
Himes et al.; U.S. Appl. No. 12/716,147 entitled "Displaying and Manipulating Brain Function Data Including Filtering of Annotations," filed Mar. 2, 2010.
Rothman et al.; Local Cooling: a therapy for intractable neocortical epilepsy; Epilepsy Currents; vol. 3; No. 5; pp. 153-156; Sep./Oct. 2003.
Echauz et al.; U.S. Appl. No. 12/792,582 entitled "Processing for Multi-Channel Signals," filed Jun. 2, 2010.
Higgins et al.; U.S. Appl. No. 13/026,961 entitled "Neurological monitoring and alerts," filed Feb. 14, 2011.
Harris et al.; U.S. Appl. No. 13/050,839 entitled "System and methods for analyzing seizure activity," filed Mar. 17, 2011.
Leyde et al.; U.S. Appl. No. 13/070,333 entitled "Communication Error Alerting in an Epilepsy Monitoring System," filed Mar. 23, 2011.
Leyde et al.; U.S. Appl. No. 13/070,357 entitled "Patient Entry Recording in an Epilepsy Monitoring System," filed Mar. 23, 2011.
Spector et al.; High and Low Perceived Self-Control of Epileptic Seizures; Epilepsia, vol. 42(4), Apr. 2001; pp. 556-564.
Chen et al.; Clinical utility of video—EEG monitoring; Perdiatric Neurology; vol. 12; No. 3; pp. 220-224; 1995.
European Patent Application No. 06848279.3 Decision to refuse a European Patent application dated Feb. 4, 2014.

* cited by examiner

Configurable Communication State Machine

METHODS AND SYSTEMS FOR RECOMMENDING AN APPROPRIATE ACTION TO A PATIENT FOR MANAGING EPILEPSY AND OTHER NEUROLOGICAL DISORDERS

RELATED APPLICATIONS

The present invention is related to U.S. patent application Ser. No. 11/321,898, entitled "Methods and Systems for Recommending an Appropriate Pharmacological Treatment to a Patient for Managing Epilepsy and Other Neurological Disorders," filed Dec. 28, 2005, to Leyde et al., and U.S. patent application Ser. No. 11/322,150, entitled "Systems and Methods for Characterizing a Patient's Propensity for a Neurological Event and for Communicating with a Pharmacological Agent Dispenser," filed Dec. 28, 2005, to Bland et al., the complete disclosures of which are incorporated herein by reference.

BACKGROUND OF THE INVENTION

The present invention relates generally to characterizing a patient's propensity for a future neurological event and communicating with the patient. More specifically, the present invention relates to characterizing a propensity for a future seizure and when it is determined that the patient has a high or elevated propensity for a seizure, providing a communication to the patient that is indicative of an appropriate action for responding to the patient's elevated propensity for the seizure. Optionally, such information may be incorporated into an interactive communication protocol in order to convey appropriate communications, such as instructions or recommendations to the patient and receive historical and real-time patient status information and acknowledgements associated with the management of the patient's care.

Epilepsy is a disorder of the brain characterized by chronic, recurring seizures. Seizures are a result of uncontrolled discharges of electrical activity in the brain. A seizure typically manifests as sudden, involuntary, disruptive, and often destructive sensory, motor, and cognitive phenomena. Seizures are frequently associated with physical harm to the body (e.g., tongue biting, limb breakage, and burns), a complete loss of consciousness, and incontinence. A typical seizure, for example, might begin as spontaneous shaking of an arm or leg and progress over seconds or minutes to rhythmic movement of the entire body, loss of consciousness, and voiding of urine or stool.

A single seizure most often does not cause significant morbidity or mortality, but severe or recurring seizures (epilepsy) results in major medical, social, and economic consequences. Epilepsy is most often diagnosed in children and young adults, making the long-term medical and societal burden severe for this population of patients. People with uncontrolled epilepsy are often significantly limited in their ability to work in many industries and cannot legally drive an automobile. An uncommon, but potentially lethal form of seizure is called status epilepticus; in which a seizure continues for more than 30 minutes. This continuous seizure activity may lead to permanent brain damage, and can be lethal if untreated.

While the exact cause of epilepsy is uncertain, epilepsy can result from head trauma (such as from a car accident or a fall), infection (such as meningitis), or from neoplastic, vascular or developmental abnormalities of the brain. Most epilepsy, especially most forms that are resistant to treatment (i.e., refractory), are idiopathic or of unknown causes, and is generally presumed to be an inherited genetic disorder. Demographic studies have estimated the prevalence of epilepsy at approximately 1% of the population, or roughly 2.5 million individuals in the United States alone. Approximately 60% of these patients have epilepsy where specific focus can be identified in the brain and are therefore candidates for some form of a focal treatment approach.

In order to assess possible causes and to guide treatment, epileptologists (both neurologists and neurosurgeons) typically evaluate people with seizures with brain wave electrical analysis (e.g., electroencephalography or "EEG" and electrocorticograrri "ECoG", which are hereinafter referred to collectively as "EEG") and imaging studies, such as magnetic resonance imaging (MRI). While there is no known cure for epilepsy, chronic usage of anticonvulsant and antiepileptic medications can control seizures in most people. The anticonvulsant and antiepileptic medications do not actually correct the underlying conditions that cause seizures. Instead, the anticonvulsant and antiepileptic medications manage the patient's epilepsy by reducing the frequency of seizures. There are a variety of classes of antiepileptic drugs (AEDs), each acting by a distinct mechanism or set of mechanisms.

For most cases of epilepsy, the disease is chronic and requires chronic medications for treatment. AEDs generally suppress neural activity by a variety of mechanisms, including altering the activity of cell membrane ion channels and the propensity of action potentials or bursts of action potentials to be generated. These desired therapeutic effects are often accompanied by the undesired side effect of sedation. Some of the fast acting AEDs, such as benzodiazepine, are also primarily used as sedatives. Other medications have significant non-neurological side effects, such as gingival hyperplasia, a cosmetically undesirable overgrowth of the gums, and/or a thickening of the skull, as occurs with phenyloin. While chronic usage of AEDs has proven to be effective for a majority of patients suffering from epilepsy, the persistent side effects can cause a significant impairment to a patient's quality of life. Furthermore, about 30% of epileptic patients are refractory (e.g., non-responsive) to the conventional chronic AED regimens. This creates a scenario in which over 500,000 patients in the United States alone have uncontrolled epilepsy.

If a patient is refractory to treatment with chronic usage of medications, surgical treatment options may be considered. If an identifiable seizure focus is found in an accessible region of the brain, which does not involve "eloquent cortex" or other critical regions of the brain, then resection is considered. If no focus is identifiable, or there are multiple foci, or the foci are in surgically inaccessible regions or involve eloquent cortex, then surgery is less likely to be successful or may not be indicated. Surgery is effective in more than half of the cases in which it is indicated, but it is not without risk, and it is irreversible. Because of the inherent surgical risks and the potentially significant neurological sequelae from resective procedures, many patients or their parents decline this therapeutic modality.

Some non-resective functional procedures, such as corpus callosotomy and subpial transection, sever white matter pathways without removing tissue. The objective of these surgical procedures is to interrupt pathways that mediate spread of seizure activity. These functional disconnection procedures can also be quite invasive and may be less effective than resection.

An alternative treatment for epilepsy that has demonstrated some utility is Vagus Nerve Stimulation (VNS). This is a reversible procedure which introduces an electronic device which employs a pulse generator and an electrode to alter neural activity. The vagus nerve is a major nerve pathway that emanates from the brainstem and passes through the neck to control visceral function in the thorax and abdomen. VNS uses intermittent stimulation of the vagus nerve in the neck in an attempt to reduce the frequency and intensity of seizures. See Fisher et al., "Reassessment: Vagus nerve stimulation for epilepsy, A report of the Therapeutics and Technology Assessment Subcommittee of the American Academy of Neurology," Neurology 1999; 53:666-669. While not highly effective, it has been estimated that VNS reduces seizures by an average of approximately 50% in about 50% of patients who are implanted with the device.

Another recent alternative electrical stimulation therapy for the treatment of epilepsy is deep brain stimulation (DBS). Open-loop deep brain stimulation has been attempted at several anatomical target sites, including the anterior nucleus of the thalamus, the centromedian nucleus of the thalamus, and the hippocampus. The results have shown some potential to reduce seizure frequency, but the efficacy leaves much room for improvement.

There have also been a number of attempts described in the patent literature regarding the use of predictive algorithms that purportedly can predict the onset of a seizure. When the predictive algorithm predicts the onset of a seizure, some type of warning is provided to the patient regarding the oncoming seizure. For example, see U.S. Pat. No. 3,863,625 to Viglione and U.S. Pat. No. 6,658,287 to Litt et al.

While conventional treatments for epilepsy have had some success, improvements are still needed.

SUMMARY OF THE INVENTION

The present invention provides improved systems and methods for monitoring, managing, and treating neurological disorders and communicating with a patient regarding an appropriate action. The systems and methods of the present invention are configured to characterize a patient's propensity for a future neurological event, such as an epileptic seizure.

In preferred embodiments, the present invention is for managing epilepsy—including the prevention or reduction of the occurrence of epileptic seizures and/or mitigating their effects. The method of preventing an epileptic seizure comprises characterizing a patient's propensity for a future seizure, and upon the determination that the patient has an elevated propensity for the seizure, communicating to the patient and/or a health care provider a therapy recommendation.

In one embodiment, a patient's propensity for a seizure can be estimated or derived from a neural state which can be characterized as a point along a single or multi-variable state space continuum. The term "neural state" is used herein to generally refer to calculation results or indices that are reflective of the state of the patient's neural system, but does not necessarily constitute a complete or comprehensive accounting of the patient's total neurological condition. The estimation and characterization of "neural state" may be based on one or more patient dependent parameters from the brain, such as electrical signals from the brain, including but not limited to electroencephalogram signals "EEG" and electrocorticogram signals "ECoG" (referred to herein collectively as "EEG"), brain temperature, blood flow in the brain, concentration of AEDs in the brain, etc.).

In addition to using the neural state, other patient dependent parameters, such as patient history, and/or other physiological signals from the patient may be used to characterize the propensity for seizure. Some of the physiological signals that may be monitored include, temperature signals from other portions of the body, blood flow measurements in other parts of the body, heart rate signals and/or change in heart rate signals, respiratory rate signals and/or change in respiratory rate signals, chemical concentrations of other medications, pH in the blood or other portions of the body, blood pressure, other vital signs, other physiological or biochemical parameters of the patient's body, or the like).

The methods and systems of the present invention may also have the capability to use feedback from the patient as an additional metric for characterizing the patient's propensity for a seizure. For example, in some embodiments, the system may allow the patient to affirm that the AED was taken, indicate that they didn't take the AED, indicate that they are feeling an aura or are experiencing a prodrome or other symptoms that precede a seizure, indicate that they had a seizure, indicate that they are going to sleep or waking up, engaging in an activity that is known to the patient to interfere with their state, or the like.

The present invention has broad therapeutic and diagnostic applications, including the control of neural state to reduce the patient's propensity for future neurological symptoms, as well as to the prediction of future neurological symptoms. The present invention may use the propensity for seizure characterization to determine if an action is needed, and if an action is needed, determine the appropriate action, and communicate the appropriate action to the patient and/or caregiver in an interactive manner so that the management of the patient's care may be improved.

In preferred embodiments, the present invention provides methods and systems for managing epilepsy—including the prevention or reduction of the occurrence of epileptic seizures and/or mitigating their effects. The method of managing or treating an epileptic seizure typically comprises measuring one or patient parameters and processing the parameters to characterize the patient's propensity for a future epileptic seizure. The characterized propensity for the future seizure may be used to determine an appropriate action for managing or treating the predicted seizure. A recommendation or instruction is communicated to the patient and/or a health care provider that is indicative of the appropriate action.

The systems of the present invention may comprise one or more patient interface assemblies that are configured to measure one or more signals that are predictive or indicative of a patient's propensity for the future epileptic seizure and a device assembly that is configured to process the one or more signals. When the processed signals are indicative of an increased propensity for the epileptic seizure, the assembly facilitates selection of a clinician defined recommendation and communication of the suitable clinician defined recommendation to the patient that is indicative of an appropriate action. The communication to the patient may be provided with a patient communication assembly that is in wired or wireless communication with the device assembly.

In some embodiments, the device assembly is at least partially implanted within the patient's body and the patient communication assembly is disposed external to the patient's body. Communication between the device assembly and the patient communication assembly is done transcutaneously using conventional wireless protocols.

The patient interface assemblies of the present invention may include intracranial electrodes, extracranial electrodes, implanted or external drug delivery devices, or other physiological sensors. Typically the electrodes are in communication with a nervous system component. Signals measured by the patient interface assemblies may be transmitted over a wireless or wired link to the device assembly, where the signals are processed to characterize the patient's propensity for a future seizure.

While a variety of other methods may be used to characterize the patient's propensity for a future seizure, the systems and methods of the present invention typically characterize the patient's propensity for a future seizure by using a predictive algorithm to measure the patient's neural state and other patient dependent parameters (e.g., non-neural physiological signals, patient history, patient inputs, etc.). The patient's neural state may be measured by extracting features from the one or more signals from the brain that are indicative or predictive (either themselves or in combination) of the patient's propensity for a seizure.

The feature extractors and classifier modules of the predictive algorithm may be embodied in a device that is implanted in a patient, external to the patient, or in a combination thereof. For example, in one configuration, both the feature extractors and classifier are embodied within a device assembly that is implanted in the patient. In another configuration, both the feature extractors and classifier may be embodied in a device that is external to the patient's body, such as in a patient communication assembly. In yet other configurations, one of the feature extractor and classifier may be embodied in a device assembly that is implanted in the patient's body, while the other of the classifier and feature extractor may be embodied in a device that is external to the patient's body (e.g., patient communication assembly).

In any of such embodiments, the characterized patient's propensity for the seizure (or other output from the predictive algorithm) may then be input into a treatment algorithm, such as a fixed or configurable state machine that implements an interactive communication protocol to generate and convey appropriate communications (e.g., recommendations or instructions) to the patient. The state machine may be embodied in a device that is implanted in the body or external to the body. The state machine may optionally be configured to receive patient historical information and acknowledgements associated with the management of the patient's condition, and the algorithms may use the inputs from the patient to determine the recommendation that is provided to the patient.

In some embodiments, the communication provided to the patient may provide a recommendation or instruction to take an acute dosage of a specified pharmacological agent (e.g., neuro-suppressant, sedative, AED or anticonvulsant), adjust the timing or dosage of a chronically prescribed pharmacological agent, perform a specific action such as assuming a safe posture or position, activate an implanted drug dispenser, manually activate a neuromodulation treatment such as vagus nerve stimulation (VNS), deep brain stimulation (DBS), cortical stimulation, make one or more behavioral modifications (e.g., of lying down, turning off lights, interrupting working, touching the face, hyperventilating, hypoventilating, holding breath, performing a valsalva maneuver, applying external stimulator, applying transcutaneous electrical neural stimulation, and other action or cessation of activity), or the like. The systems of the present invention may optionally utilize communications supplied by a patient or caregiver such as confirmation that a medication has been taken, that the patient is going to bed, that the patient has awoken, that the patient is experiencing an aura, or the like. This information may be in turn used in subsequent calculations of the patient's propensity for a seizure. In other embodiments, however, the therapy may be automatically administered to the patient and the patient may be notified about the therapy via a communication.

In preferred embodiments, the instructions or recommendations provided by the systems and methods of the present invention will be a reflective of, or a function of, the patient's propensity for the future seizure, which is typically at least partially derived from the neural state. Consequently, depending on what the clinician determines to be appropriate actions for the particular patient, a customized recommendation may be provided to the. For example, if the propensity for a future seizure (which may be a function of the neural state) is indicative of a long time horizon or a low likelihood of a seizure, the recommendation or instruction for treatment communicated to the patient will be reflective of the low risk/long time horizon. On the other hand, if the prediction of the seizure is indicative of a short time horizon or a high likelihood of a seizure, the recommendation or instruction for treatment to the patient will be reflective of such a prediction. Thus, in the case of a long prediction time horizon or a low probability of a seizure, a smaller than "normal" oral dose of a relatively slower onset antiepileptic drug or an antiepileptic drug with a lower side effect profile may be the appropriate therapies recommended by the clinician. In contrast, for a short prediction horizon or a high probability of a seizure, a higher than "normal" dosage of a faster acting drug, such as a sublingual, buccal, intranasal, intramuscular, or intravenous dose, may be the appropriate action recommended by the clinician.

In one specific embodiment, the present invention provides a system that comprises a predictive algorithm that is configured to be used in conjunction with acute dosages of a pharmacological agent, including an AED, such as the rapid onset benzodiazepines. Other antiepileptic drugs or sedatives may be used as well. The predictive algorithm may be used to characterize a patient's propensity for the seizure. If the predictive algorithm determines that the patient has an elevated propensity for an epileptic seizure or otherwise predicts the onset of a seizure, the system may provide an output that recommends or instructs the patient to take an acute dosage of a pharmacological agent (such as an AED) to prevent the occurrence of the seizure or reduce the magnitude or duration of the seizure.

As used herein, the term "anti-epileptic drug" or "AED" generally encompasses pharmacological agents that reduce the frequency or likelihood of a seizure. There are many drug classes that comprise the set of antiepileptic drugs (AEDs), and many different mechanisms of action are represented. For example, some medications are believed to increase the seizure threshold, thereby making the brain less likely to initiate a seizure. Other medications retard the spread of neural bursting activity and tend to prevent the propagation or spread of seizure activity. Some AEDs, such as the Benzodiazepines, act via the GABA receptor and globally suppress neural activity. However, other AEDs may act by modulating a neuronal calcium channel, a neuronal potassium channel, a neuronal NMDA channel, a neuronal AMPA channel, a neuronal metabotropic type channel, a neuronal sodium channel, and/or a neuronal kainite channel.

Unlike conventional anti-epileptic drug treatments, which provide for a chronic regimen of pharmacological agents, the present invention is able to manage seizures acutely while substantially optimizing the intake of the pharmacological agent by instructing the patient to take a pharmacological agent only when it is determined that a pharmacological agent is necessary. Furthermore, with this new paradigm of seizure prevention, the present invention provides a new indication for pharmacotherapy. This new indication is served by several existing medications, including AEDs, given at doses which are sub-therapeutic to their previously known indications, such as acute AED administration for seizure termination or status epilepticus. Since his new indication is served by a new and much lower dosing regimen and consequently a new therapeutic window, the present invention is able to provide a correspondingly new and substantially reduced side effect profile. For example, the present invention allows the use of dosages that are lower than FDA-approved dosages for the various anti-epileptic agents. This dosing may be about 5% to about 95% lower than the FDA-recommended dose for the drug, and preferably at or below 90% of the FDA-recommended dose, and most preferably below about 50% of the FDA-recommended dose, below about 25% of the FDA-recommended dose, below about 10% of the FDA recommended dose, or below about 5% of the FDA recommended dose. But as can be appreciated, if the measured signals indicate a high risk for a seizure, the methods and systems of the present invention may recommend taking the FDA approved dose or a higher than FDA approved dose of the AED to prevent the predicted seizure.

In addition to or as an alternative to the recommendation provided to the patient, the systems and methods of the present invention may also provide an automatic, closed-loop treatment to the patient to prevent or manage the predicted seizure. The automatic treatment may comprise electrical stimulation and/or drug delivery via an implanted or external drug dispenser. The electrical stimulation may be intracranial stimulation of a nervous system component, extracranial stimulation of a nervous system component, (e.g., a peripheral nerve, such as the vagus nerve), or a combination thereof.

In another specific embodiment, the present invention provides a system that comprises a predictive algorithm that may be used to modify or alter the scheduling and dosing of a chronically prescribed pharmacological agent, such as an AED, to optimize or custom tailor the dosing to a particular patient at a particular point in time. This allows for improved (1) efficacy for individual patients, since there is variation of therapeutic needs among patients, and for (2) improved response to variation in therapeutic needs for a given patient with time, resulting form normal physiological variations as well as from external and environmental influences, such as stress, sleep deprivation, the presence of flashing lights, alcohol intake, and the like The predictive algorithm may be used to characterize a patient's propensity for the future seizure, typically by monitoring the patient's neural state. If the predictive algorithm determines that the patient is at an increased propensity or probability of an epileptic seizure or otherwise predicts the onset of a seizure, the system may provide an output that indicates or otherwise recommends or instructs the patient to take an accelerated or increased dosage of a chronically prescribed pharmacological agent. Consequently, the present invention is able to provide a lower chronic plasma level of the AED and modulate the intake of the prescribed agent in order to decrease side effects and maximize benefit of the AED.

While the following discussion focuses on characterizing the patient's propensity for the epileptic seizure and managing and treating the epileptic seizures through providing recommendations or instructions to the patient to take an action (e.g., take an acute dosage of a medication, improved dosing of chronic medication, or other therapies for managing the epileptic seizures), the present invention may also be applicable to controlling other neurological or non-neurological disorders with a predictive algorithm and the administration of other acute pharmacological agents or other acute treatments. For example, the present invention may also be applicable to management of Parkinson's disease, essential tremor, Alzheimer's disease, migraine headaches, depression, or the like. As can be appreciated, the features extracted from the signals and used by the predictive algorithm will be specific to the underlying disorder that is being managed. While certain features may be relevant to epilepsy, such features may or may not be relevant to the state measurement for other disorders.

For a further understanding of the nature and advantages of the present invention, reference should be made to the following description taken in conjunction with the accompanying drawings.

INCORPORATION BY REFERENCE

All publications, patents, and patent applications mentioned in this specification are herein incorporated by reference to the same extent as if each individual publication, patents, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
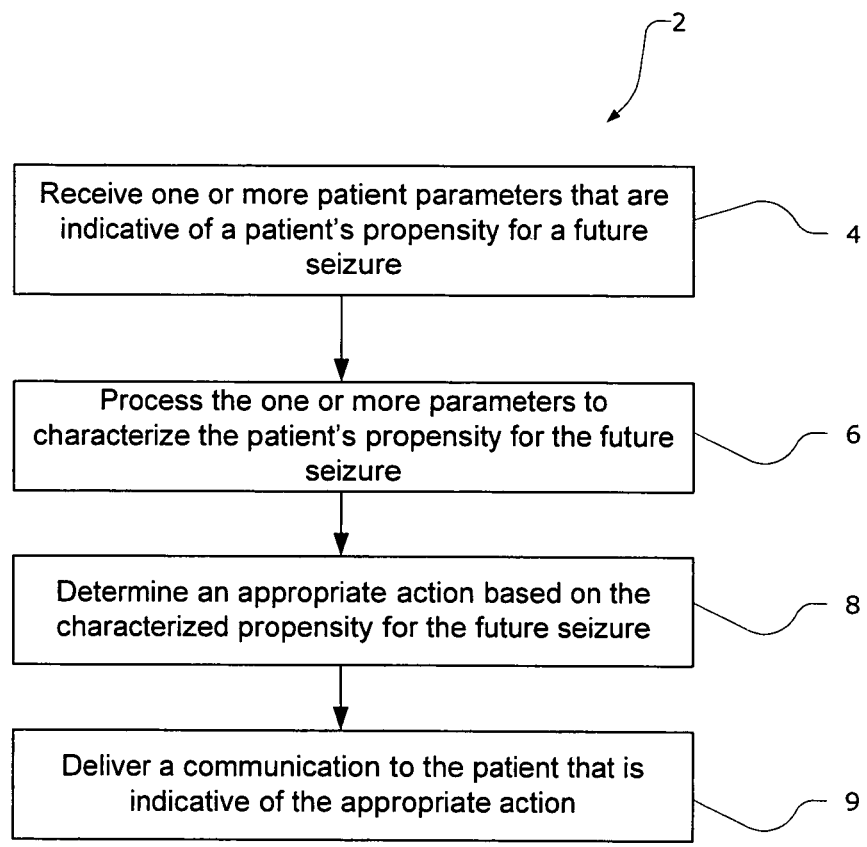
FIG. 1 illustrates a simplified method encompassed by the present invention.

The present invention provides systems and methods for characterizing a patient's propensity for a future seizure and communicating an automated prodrome, such as a recommendation to the patient regarding an appropriate action for managing (e.g., preventing, reducing a magnitude, or reducing a duration of the seizure) the future seizure. FIG. 1 illustrates a simplified method 2 encompassed by the present invention. In the illustrated embodiment, one or more patient dependent parameters are received from a patient (Step 4). The one or more parameters are processed and if the output is undesirable in some way or is indicative of an increased or elevated propensity for a future seizure, an appropriate action is determined that will prevent or reduce the likelihood, magnitude, or duration of the seizure (Steps 6 and 8). A communication may be generated that is indicative of the appropriate action and the communication may be provided to the patient, health care provider, and/or caregiver of the patient (Step 9). Typically, the communication will be in the form of a warning, instruction, or recommendation.

Figure 21:
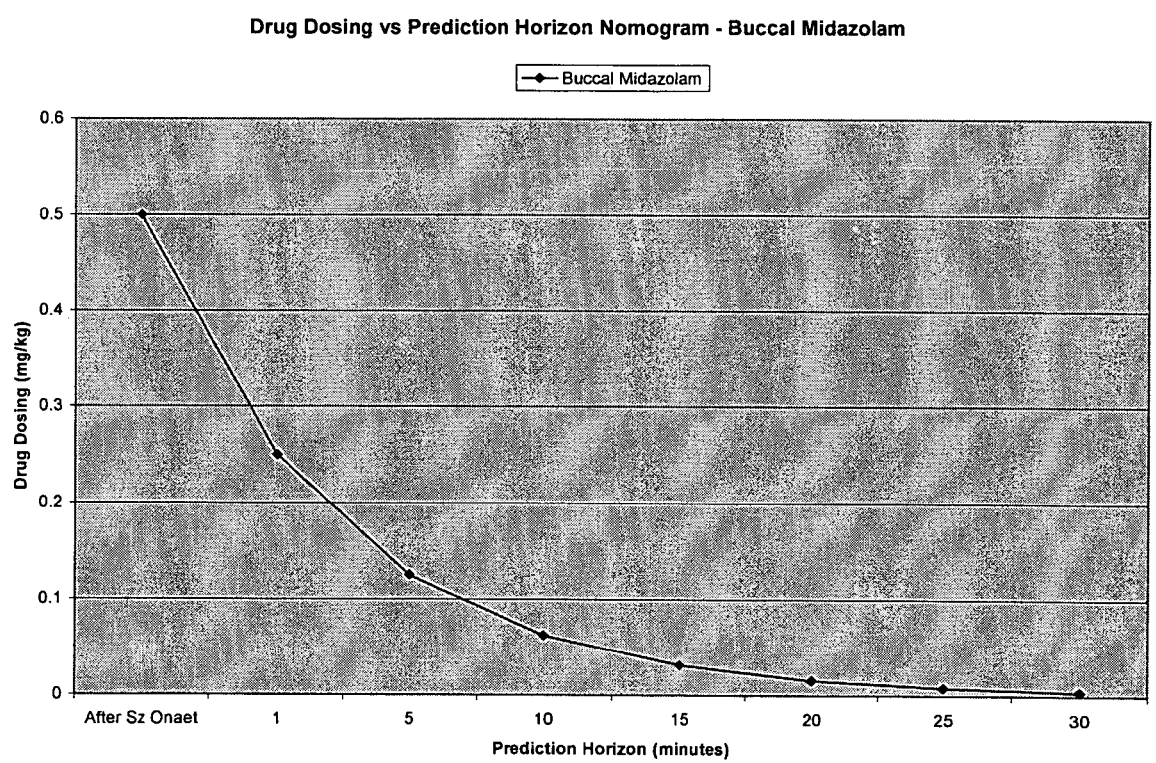
FIG. 21 is a sample nomogram that illustrates a sample drug dosing versus a prediction time horizon for buccal midazolam.
Figure 22:
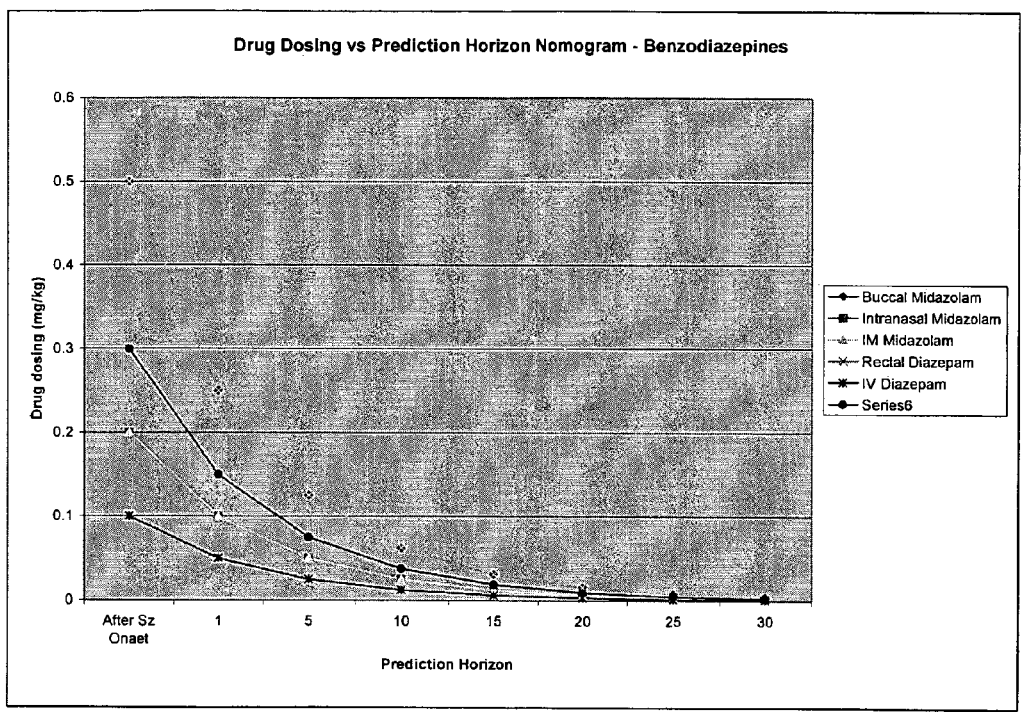
FIG. 22 is a sample nomogram that illustrates a sample drug dosing versus a prediction time horizon for benzodiazepines.

Advantageously, the methods and system of the present invention allow a physician to customize the information or recommendations provided to the patient. Certain patients may benefit from certain actions, when performed in a timeframe preceding a seizure. For example, the appropriate action is typically in the form of electrical stimulation or manual or automatic delivery of a pharmacological agent. In preferred embodiments, parameters of the stimulation and/or pharmacological agent intervention (and the communication to the patient) may be co-related to or a function of the prediction of the seizure and customized for the patient. For example, if the patient's propensity for the seizure is low and/or a long time horizon is estimated for the seizure, the dosage of the recommended drug could be lower or the parameters of the electrical stimulation could be reduced, or the like. On the other hand, if patient's propensity for the seizure is high or a short time horizon is estimated for the seizure, the dosage of the recommended drug could be higher or the parameters of the electrical stimulation could be increased. Two sample nomogram relating the dose versus a prediction horizon is shown in FIGS. 21 and 22.

While electrical stimulation and pharmacological treatment recommendations are preferred actions, the present invention further encompasses other recommendations, such as resting, turning off the lights, performing non-repetitive tasks (or repetitive ones to induce a seizure), facial touching or other tactile stimulation, some forms of gastrointestinal stimulation, and others. These actions may serve to reduce the likelihood, magnitude, or duration of a seizure.

Additionally, the physician can customize preventative therapy for specific propensity levels, time horizons, probabilities, or neural state measurements, including making recommendations for specific doses of certain medications that have efficacy in the prevention of seizures. This actionable information is valuable for all patients, and more so for cognitively impaired patients; the presentation of actionable information elicits improved compliance in comparison to a simple seizure prediction or probability estimation, which is more apt to elicit anxiety which can negatively impact compliance.

Figure 2:
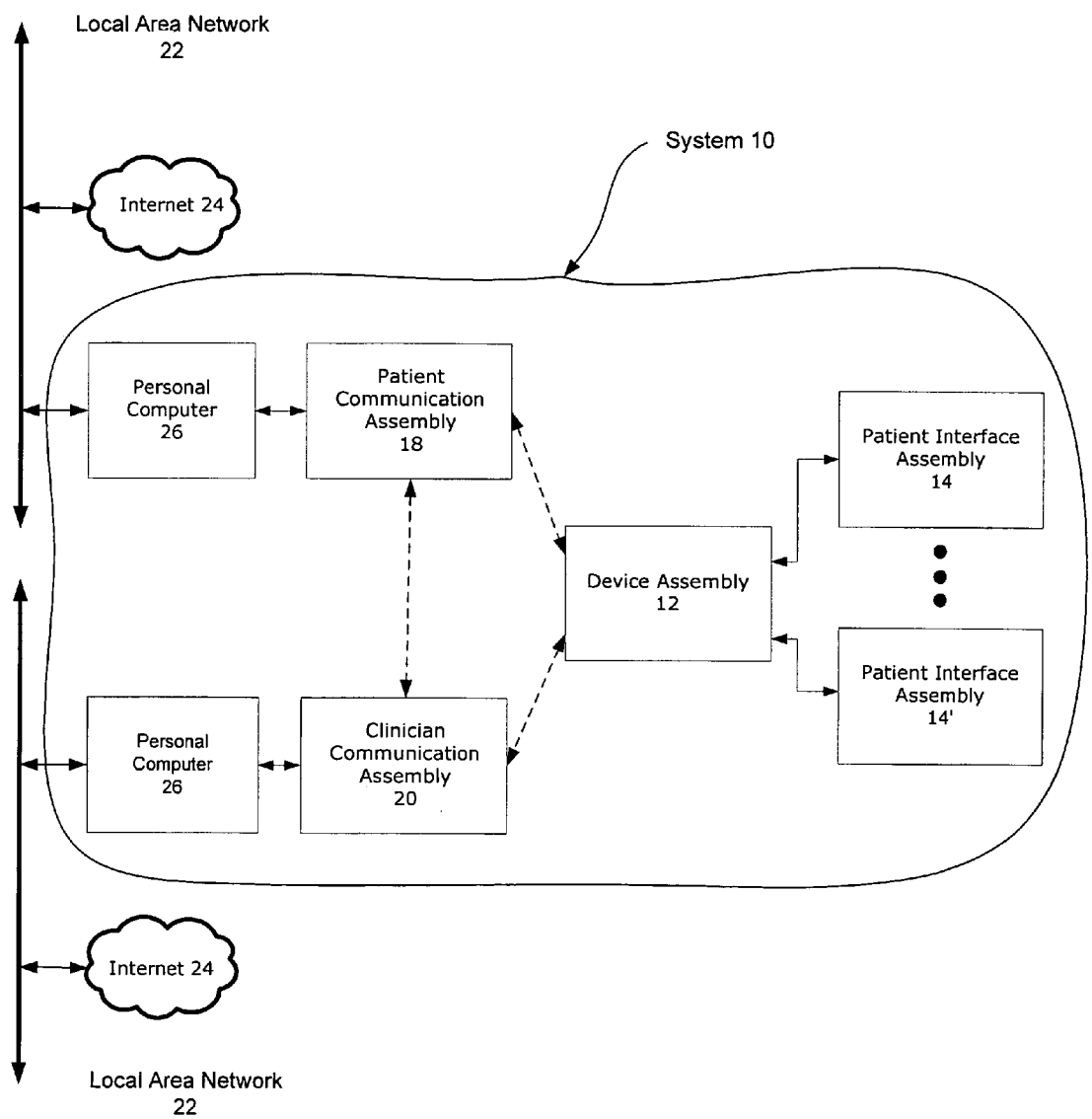
FIG. 2 shows a simplified system that may be used to carry out the method illustrated in FIG. 1.

FIG. 2 illustrates a simplified system for carrying out the present invention. System 10 comprises a device assembly 12 that is in communication with one or more patient interface assembly(s) 14, 14'. Patient interface assembly 14 typically comprises one or more electrode arrays, such as a multichannel intracranial EEG electrode array, temperature sensors, biochemical sensors, stimulation electrodes, and/or drug dispensing ports. If patient interface assembly 14 is used for sensing signals from the patient, signal(s) from patient interface assembly 14 are transmitted over a communication link to device assembly 12 where the measured signal(s) are processed in order to determine a patient's propensity for the seizure, which may indicate normal neural activity, abnormal neural activity that is indicative of an elevated risk of future seizure activity, or the like. Based at least in part on the patient's propensity for the seizure, device assembly 12 may optionally generate a therapeutic output signal, and automatically deliver a therapeutic treatment to the patient through one or more of the patient interface assemblies 14. The patient interface assembly 14 used to deliver the therapeutic treatment may be the same patient interface assembly 14 used for sensing the signals from the patient, or the patient interface assembly 14 may be a different assembly.

A patient communication assembly 18 may be in wireless or wired communication with device assembly 12 so as to provide a user interface for one-way or two-way communication between the patient and other components of system 10. Patient communication assembly 18 may be used to deliver warnings, information, recommendations, or instructions to the patient. Optionally, patient communication assembly 18 may also allow the patient to provide inputs to the system 10 so as to provide an interactive communication protocol between system 10 and the patient. The inputs from the patient may be used to indicate that a seizure has occurred, that the patient is having an "aura", or the like. Additionally, the patient may indicate states of mental or physiological stress, sleep deprivation, alcohol consumption or withdrawal, presence or absence of other pharmacological agents, dosing and timing of antiepileptic drugs or other medications, each of which may alter neural state, seizure thresholds, and/or propensity for seizures. The patient inputs may be stored in memory and used by system 10 or clinician for training of the prediction algorithm.

The patient may also use patient communication assembly 18 to query information from system 10; this information includes propensity for seizure, neural state, estimations for the likelihood or probability of a seizure, estimated time horizons, and responses to pharmacological agents, such as antiepileptic drugs, which the patient may be taking chronically, acutely, or as part of a trial dose.

Optionally, system 10 may include a personal computer or other external computing device 26 that is configured to communicate with the patient communication assembly 18. Personal computer 26 may allow for download or upload of data from patient communication assembly 18 or device assembly 12, programming of the patient communication assembly 18 or for programming of the device assembly 12, or the like.

System 10 may also optionally include a clinician communication assembly 20 that is in direct or indirect communication with device assembly 12. For example, clinician communication assembly may communicate with device assembly 12 with a direct communication link, or may communicate with device assembly 12 indirectly through patient communication assembly 18 (or another communication assembly (not shown)). Clinician communication assembly 20 may also be in communication with a personal computer 26 to allow for download or upload of information from clinician communication assembly 20, or configuration or programming of the clinician communication assembly 20, patient communication assembly 18, device assembly 12, or the like. Clinician communication assembly 20 and personal computer 26 may allow a patient's guardian or clinician to remotely monitor the patient's neural state and/or medication intake in a real-time or non-real time basis.

System 10 may also have the capability to directly or indirectly connect to the Internet 24, or a wide area network or a local area network 22 so as to allow uploading or downloading of information from patient communication assembly 18 or clinician communication assembly 20 to a remote server or database, or to allow a clinician or supervisor to remotely monitor the patient's propensity for seizure on a real-time or non-real-time basis. In the illustrated embodiment, connection to the Internet is carried out through personal computers 26, but in other embodiments, it may be possible to directly connect to the Internet 24 through a communication port on patient communication assembly 18, clinician communication assembly 20, or device assembly 12.

Patient interface assembly 14 illustrated to in FIG. 2 typically includes a plurality of electrodes, thermistors, or other sensors, as known in the art. For embodiments that include electrodes, patient interface assembly 14 may include any number of electrodes, but typically has between about 1 electrode and about 64 electrodes, and preferably between about 2 electrodes and about 8 electrodes. The electrodes may be in communication with a nervous system component (which is used herein to refer to any component or structure that is part of or interfaced to the nervous system), a non-nervous system component, or a combination thereof. Patient interface assembly 14 typically includes an array of intracranial EEG electrodes that are either in a subgaleal location within or below the scalp and above the skull (FIGS. 3B and 4), or beneath the skull, each of which facilitates communication with some portion of the patient's nervous system. Some useful areas for placing the intracranial electrodes include, but are not limited to, the hippocampus, amygdala, anterior nucleus of the thalamus, centromedian nucleus of the thalamus, other portion of the thalamus, subthalamic nucleus, motor cortex, premotor cortex, supplementary motor cortex, other motor cortical areas, somatosensory cortex, other sensory cortical areas, Wernicke's area, Broca's area, pallido-thalamic axons, lenticulo-thalamic fiber pathway, substantia nigra pars reticulata, basal ganglia, external segment of globus pallidus, subthalalmic to pallidal fiber tracts, putamen, putamen to PGe fibers, other areas of seizure focus, other cortical regions, or combinations thereof.

In addition to being placed intracranially, the patient interface assembly 14 may be placed extracranially and in communication with an extracranial nervous system component, such as a peripheral nerve or cranial nerve, (e.g., the vagus nerve, olfactory nerve optic nerve, oculomotor nerve, trochlear nerve, trigeminal nerve, abducens nerve, facial nerve, vestibulocochlear nerve, glossopharyngeal nerve, accessory nerve, hypoglossal nerve) or it may be coupled to other portions of the patient's body, such as to an external surface of the patient's cranium (e.g., above, below, or within the patient's scalp).

In addition to or as an alternative to the EEG electrode array that are in communication with a nervous system component, patient interface assembly 14 may comprise electrodes or other sensors that are configured to sense signals from a non-nervous system component of the patient. Some examples of such signals include but are not limited to, electromyography (EMG) signals, electrocardiogram (ECG) signals, temperature signals from the brain or other portions of the body, oximetry, blood flow measurements in the brain and/or other parts of the body, heart rate signals and/or change in heart rate signals, respiratory rate signals and/or change in respiratory rate signals, chemical concentrations of AED or other medications, pH in the brain, blood, or other portions of the body, blood pressure, or other vital signs or physiological parameters of the patient's body.

As noted above, patient interface assembly 14 may also be used to deliver an electrical, thermal, optical, or medicinal therapy to a nervous system component of the patient. In such embodiments, patient interface assembly 14 may comprise one or more stimulation electrodes, a medication dispenser, or a combination thereof. The patient interface assembly 14 may be implanted within the patient's body or positioned external to the patient's body, as is known in the art.

If the patient interface assembly 14 is in the form of a medication dispenser, the medication dispenser will typically be implanted within the patient's body so as to directly infuse therapeutic dosages of one or more pharmacological agents into the patient, and preferably directly into the affected portion(s) of the brain. The medications will generally either decrease/increase excitation or increase/decrease inhibition. Consequently, the type of drugs infused and the patient's disorder will affect the area in which the medication dispenser is placed. Implanted medication reservoirs may be used, including intracranial, intraventricular (in the cerebral ventricle), intrathecal, intravenous, and other catheters. Such embodiments include indwelling central venous catheters for rapid administration as well as peripheral venous catheters. Some additional examples of medication dispensers that can be used with the system of the present invention are described in U.S. Pat. Nos. 6,094,598, 5,735,814, 5,716,377, 5,711,316, and 5,683,422. In some embodiments, the dosage and/or timing of the medication delivery may be varied depending on the output of the predictive algorithm. For example, larger dosages may be provided if the patient's propensity for a future seizure is high and smaller dosages of medication may be delivered if the patient's propensity for a seizure is low.

Figure 3A:
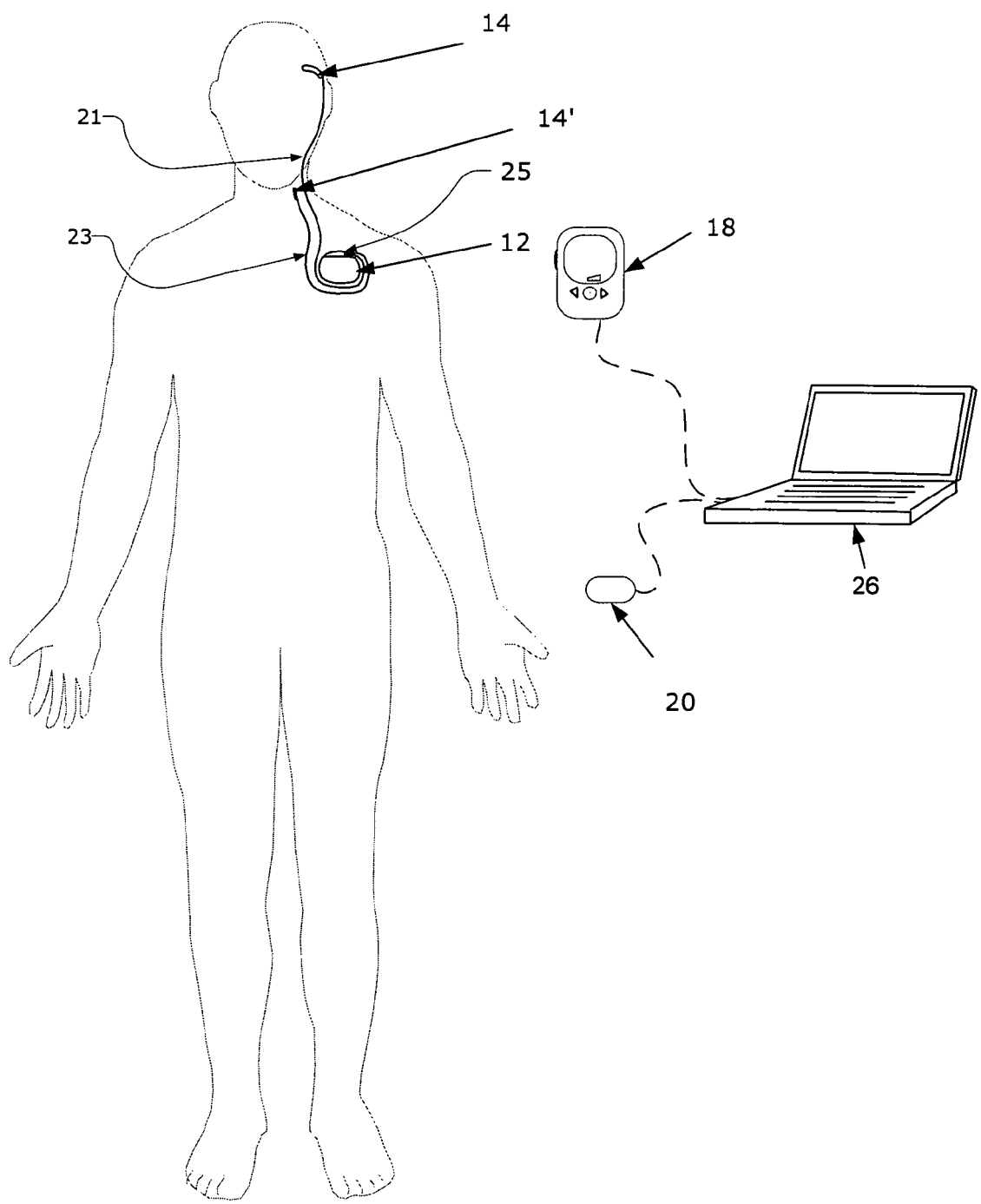
FIG. 3A illustrates an embodiment of the system in which a device assembly is implanted in a sub-clavian pocket in the patient's body and is in communication with an intracranial electrode array, a vagus nerve electrode, and a handheld, external patient communication assembly.
Figure 3B:
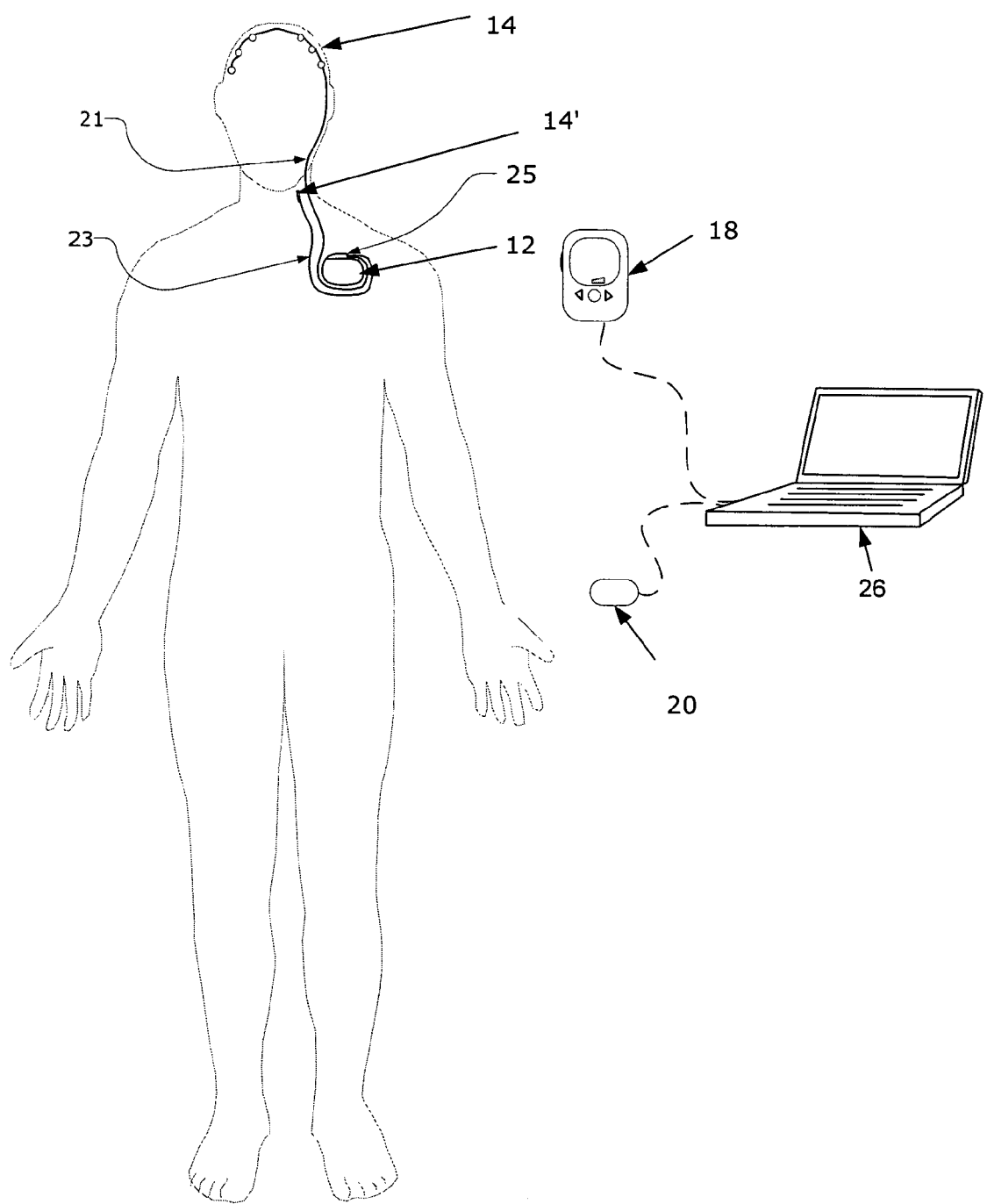
FIG. 3B illustrates an embodiment of the system in which a device assembly is implanted in a sub-clavian pocket in the patient's body and is in communication with a subgaleal electrode array, a vagus nerve electrode, and a handheld, external patient communication assembly.
Figure 4:
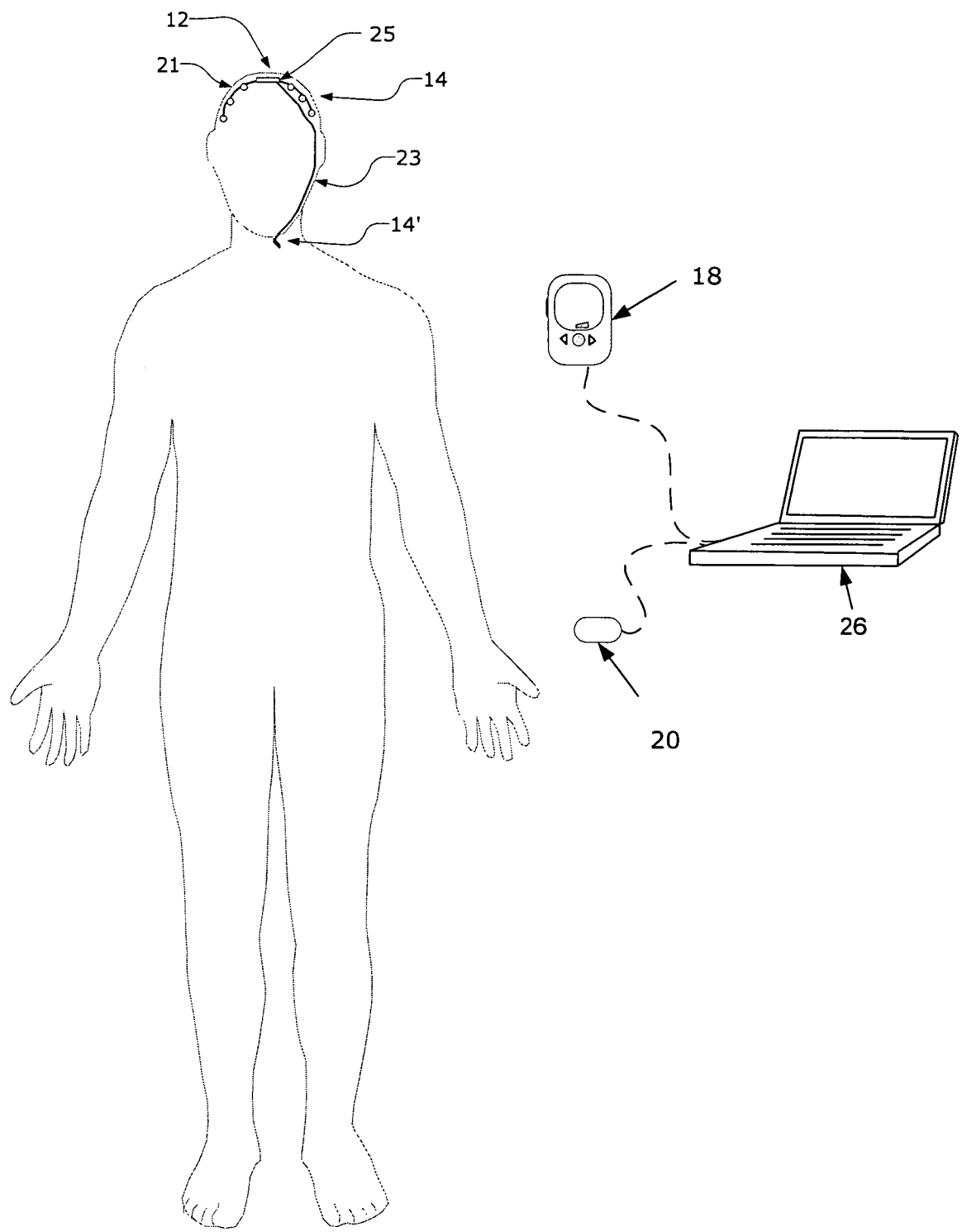
FIG. 4 illustrates an embodiment in which a device assembly is coupled to a patient's calvarium in the patient's body and in communication with a subgaleal electrode array, a vagus nerve electrode, and a handheld, external patient communication assembly.

FIGS. 3A, 3B, and 4 illustrate some specific embodiments of system 10 that are encompassed by the present invention. The illustrated system 10 includes an implanted device assembly 12 that is positioned within the patient's body. Typically, device assembly 12 is placed extracranially in a subcutaneous pocket in the patient, such as in a sub-clavicular pocket (FIGS. 3A and 3B). Alternatively, the device assembly 12 may be implanted intracranially, or otherwise coupled to the patient's skull, such as attached to or within an opening formed in the patient's calvarium (FIG. 4). Device assembly 12 typically comprises a biocompatible housing 25 (e.g. titanium, stainless steel, silicone, polyurethane, epoxy, or other such biocompatible material) that protects the internal components of the device assembly 12. While not shown, in alternative embodiments portions of device assembly 12 may be disposed external to the patient's body and worn on or around the patient's body and coupled to the implanted components. In such embodiments, device assembly 12 may be integrated into the same housing as the patient communication assembly 18 or other handheld device, or it may be in a separate housing from the patient communication assembly 18.

Device assembly 12 may be coupled to the patient interface assemblies 14, 14' (e.g., electrodes, thermistors, and other sensors) patient communication assembly 18, and a clinician communication assembly (not shown) through wireless connections, wired connections, or any combination thereof. For example, as shown in FIG. 3A, patient interface assembly 14 is in the form of intracranial electrodes that are used to sense intracranial EEG signals from the patient. FIG. 3B illustrates an embodiment of a subgaleal electrode array that is used to sense intracranial EEG signals. In both embodiments, implanted device assembly 12 is coupled to intracranial patient interface assembly 14 through conductive leads 21 that are tunneled through the patient's neck from an intracranial sensor head to the device assembly 12. As shown in FIG. 4, in embodiments in which the device assembly 12 is disposed in or on the patient's head, conductive leads 21 will have a shorter path from the sensor head to the device assembly 12. Conductive leads 23 may also be tunneled through the patient's body from the device assembly 12 to the implanted patient interface assembly 14' that is coupled to a patient's peripheral nerve, such as the vagus nerve. If device assembly 12 determines that the patient is at an elevated propensity for a seizure, extracranial patient interface assembly 14' may be used in a closed-loop fashion to selectively deliver electrical stimulation to the patient.

Device assembly 12 may transcutaneously deliver a communication output to an external patient communication assembly 18 or a clinician communication assembly 20 with a telemetry link, radiofrequency link, optical link, magnetic link, a wired link, or other wireless links. It may also be possible to transmit a communication output to the external communication assembly 18 or clinician communication assembly 20 with a wired communication link, if desired.

The parameters of the output delivered from patient interface assembly 14', whether it is the parameters of the electrical stimulation or the dosage, form, formulation, route of administration and/or timing of delivery of the pharmacological agent, will typically depend on the patient's propensity for the future seizure (e.g., which may be based at least in part on the characterized neural state). Specifically, the therapy regimen may be varied or otherwise adapted in a closed-loop manner, depending on the level of the patient's characterized propensity for a seizure. In some embodiments, device assembly 12 may automatically activate patient interface assembly 14 to deliver one or more modes of therapy to the patient and closed-loop feedback will allow device assembly 12 to dynamically adjust the parameters of the therapy so that the therapy is commensurate with or a function of the patient's characterized propensity for a seizure. For example, the patient dependent parameters may be processed to characterize the patient's propensity for seizure. If the propensity for seizure is elevated and is indicative of an imminent seizure, such a characterization will likely result in a larger magnitude of therapy than for a propensity for seizure characterization that is indicative of a longer time horizon for the future seizure. A more complete description of systems and methods for delivering electrical stimulation and for providing closed-loop control of a patient's state is found in commonly owned U.S. Pat. Nos. 6,366,813 and 6,819,956 and U.S. patent application Ser. No. 10/753,205 (filed Jan. 6, 2004), Ser. No. 10/818,833 (filed Apr. 5, 2004), Ser. No. 10/858,899 (filed Jun. 1, 2004), Ser. No. 10/889,844 (filed Jul. 12, 2004), and Ser. No. 11/159,842 (filed Jun. 22, 2005), all to DiLorenzo.

Figure 5:
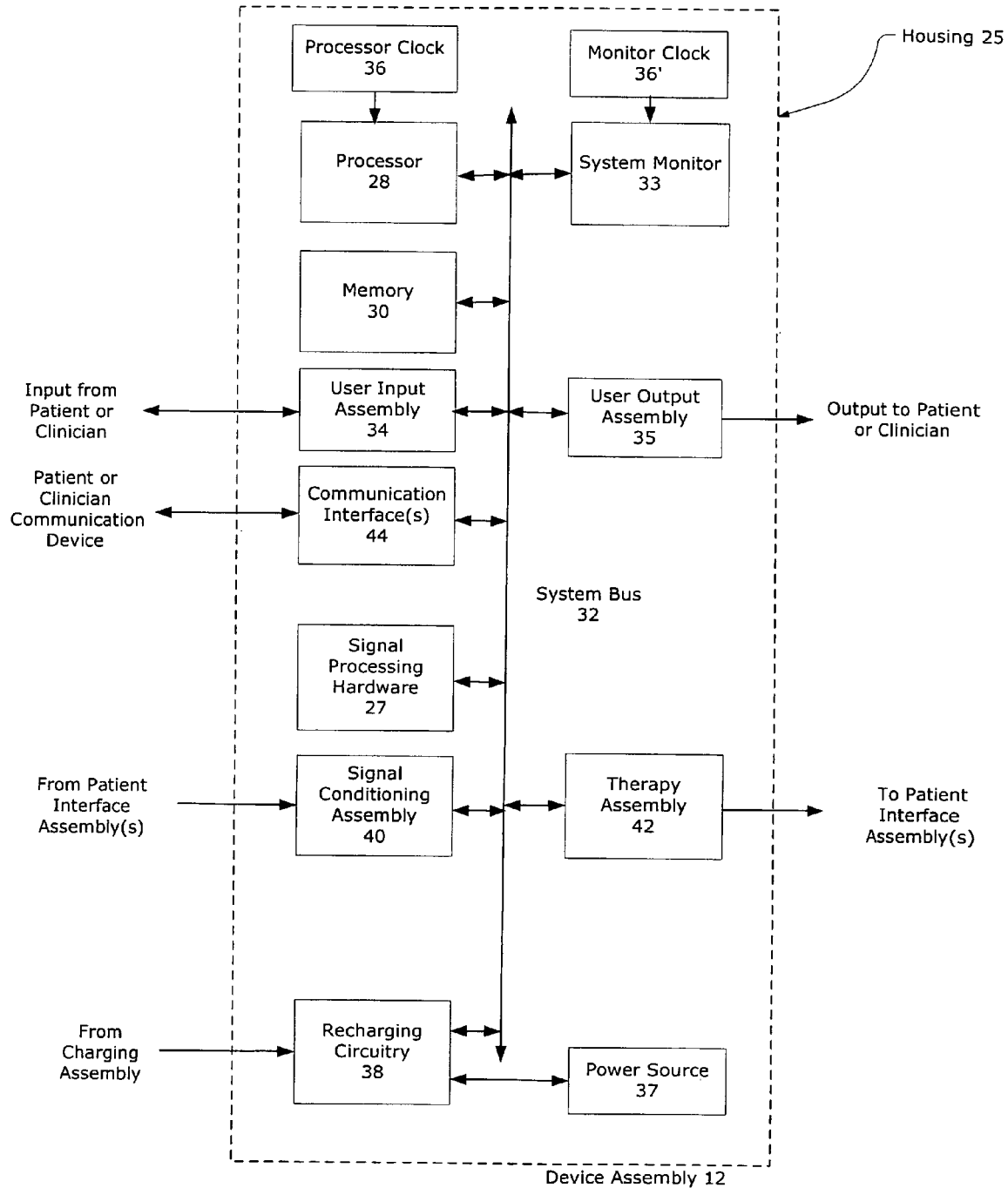
FIG. 5 illustrates a simplified device assembly that is encompassed by the present invention.

FIG. 5 illustrates one embodiment of a simplified device assembly 12 that is encompassed by the present invention. Device assembly 12 typically carries out the methods of the present invention through dedicated hardware components, software components, firmware components, or a combination thereof. In the illustrated embodiment, device assembly 12 comprises dedicated signal processing hardware 27, e.g., ASIC (Application Specific Integrated Circuit), FPGA (Field Programmable Gate Array), DSP (Digital Signal Processor), or the like, one or more processors 28, and one or more memory modules 30 that are in communication through a system bus 32. System bus 32 may be analog, digital, or a combination thereof, and system bus 32 may be wired, wireless, or a combination thereof. For ease of reference system bus 32 is illustrated as a single component, but as known to those of skill in the art, system bus 32 will typically comprise a separate data bus and power bus. The components of device assembly 12 are configured to process the data received from patient interface assembly 14, characterize the patient's propensity for a seizure, generate therapy signals for patient interface assembly 14, formulate output signals to the patient communication assembly 18, and control and coordinate most functions of device assembly 12.

Memory 30 may be used to store some or all of the constructs of the software algorithms and other software modules that carry out the functionality of the present invention. Memory 30 may also be used to store some or all of the raw or filtered signals used to characterize the patient's propensity for seizure, the patient's neural state, data regarding communications to or from the patient, data regarding the patient's history, filter settings, control law gains and parameters, therapeutic treatments, protocols, physician recommendations, or the like. While processor 28 and memory 30 are illustrated as a single element, it should be appreciated that the processor 28 and memory 30 may take the form of a plurality of different memory modules, in which various memory modules (RAM, ROM, EEPROM, volatile memory, non-volatile memory, or any combination thereof) are in communication with at least one of the processors 28 to carry out the present invention.

A system monitor 33 may be coupled to system bus 32. System monitor 33 is configured to monitor and automatically stop or otherwise interrupt processor 28 and provide some sort of notification to the patient in the event that the power source in device assembly 12 has failed or is about to fail, or if another error in device assembly 12 has occurred. Furthermore, system monitor 33 may be coupled to a reed switch (not shown) or other means that allow the patient to manually actuate system monitor 33 so as to stop or start delivery of therapy or to otherwise actuate or stop system 10. Typically, the patient may activate the reed switch with an external magnet or wand (not shown).

Optionally, system monitor 33 may be in communication with an output assembly 35 via system bus 32. Output assembly 35 may comprise a vibratory mechanism, an acoustic mechanism, a shock mechanism, or the like. System monitor 33 may automatically actuate output assembly 35 to deliver a vibratory signal, audio signal, or electrical shock to indicate to the patient that there an error in device assembly 12 or maintenance is needed to the system 10. Advantageously, the output from output assembly 35 may itself be useful for preventing the neurological event from occurring (e.g., reduce the patient's propensity for the future seizure).

Processor 28 may be coupled to a system clock 36 for timing and synchronizing the system 10. System clock 36 or additional clocks, such as system monitor clock 36' may also provide timing information for system monitor 33, or for providing timing information related to therapy delivery, recorded neural state measurements, propensity for seizure characterizations, delivery of instructions to the patient, response by the patient, time stamping of inputs from patients, or the like.

Device assembly 12 may comprise a rechargeable or non-rechargeable power source 37. Some examples of a power source that may be used with the device assembly 12 include the batteries of the type that are used to power a heart pacemaker, heart defibrillator or neurostimulator. Power source 37 provides power to the components of device assembly 12 through system bus 32. If the power source is rechargeable, a recharging communication interface, such as recharging circuitry 38 will be coupled to power source 37 to receive energy from an external recharging assembly (not shown), such as an RF transmitter or other electromagnetic field, magnetic field, or optical transmission assembly.

In addition to the recharging communication interface 38, device assembly 12 will typically comprise one or more additional communication interfaces for communicating with other components of system 10. For example, device assembly 12 may comprise a signal conditioning assembly 40 that acts as an interface between the patient interface assembly 14 and device assembly 12. Signal conditioning assembly 40 which may be comprised of hardware, software, or both, may be configured to condition or otherwise pre-process the raw signals (e.g., EEG data, ECG data, temperature data, blood flow data, chemical concentration data, etc.) received from patient interface assembly 14. Signal conditioning assembly 40 may comprise any number of conventional components such as an amplifier, one or more filters (e.g., low pass, high pass, band pass, notch filter, or a combination thereof), analog-to-digital converter, spike counters, zero crossing counters, impedance check circuitry, and the like.

Device assembly 12 may further comprise a therapy assembly 42 to interface with patient interface assembly 14' that is used to deliver therapy to the patient. Therapy assembly 42 may be comprised of software, hardware, or both, and may receive the output from processor 28 (which may be the yes/no prediction of an onset of a seizure in a near term, a characterized propensity for a future seizure, probability output of a seizure, time horizon to a predicted seizure, the patient's characterized neural state, a signal that is indicative of the patient's neural state, a control signal for controlling the therapy assembly, or the like) and use the output to generate or modify the therapy that is delivered to the patient through the patient interface assembly 14'. The therapy assembly 42 may include a control circuit and associated software, an output stage circuit, and any actuators including pulse generators, patient interfaces, electrode interfaces, drug dispenser interfaces, and other modules that may initiate a preventative or therapeutic action to be taken by or on behalf of the patient.

One or more communication interfaces 44 will facilitate communication between device assembly 12 and a remote clinician communication assembly 20, patient communication assembly 18, personal computer 26, a network 22, 24, so as to allow for communication of data, programming commands, patient instructions, or the like. Communication may be carried out via conventional wireless protocols, such as telemetry, inductive coil links, RF links, other electromagnetic links, magnetic links, infrared links, optical links, ultrasound links, or the like. Communication interface 44 will typically include both a receiver and a transmitter to allow for two-way communication so as to allow for providing software updates to device assembly 12, transmit stored or real-time data (e.g., neural state data, propensity for seizure characterizations, raw data from sensors, etc.) to the patient/clinician communication assembly, transmit inputs from the patient/clinician, or the like. However, if only one-way communication is desired, then communication interface 44 will include only one of the receiver and transmitter. Of course, in alternative embodiments in which the device assembly 12 is not fully implanted within the patient's body, it may be possible to provide a direct wired communication link with patient communication assembly 18.

Figure 6:
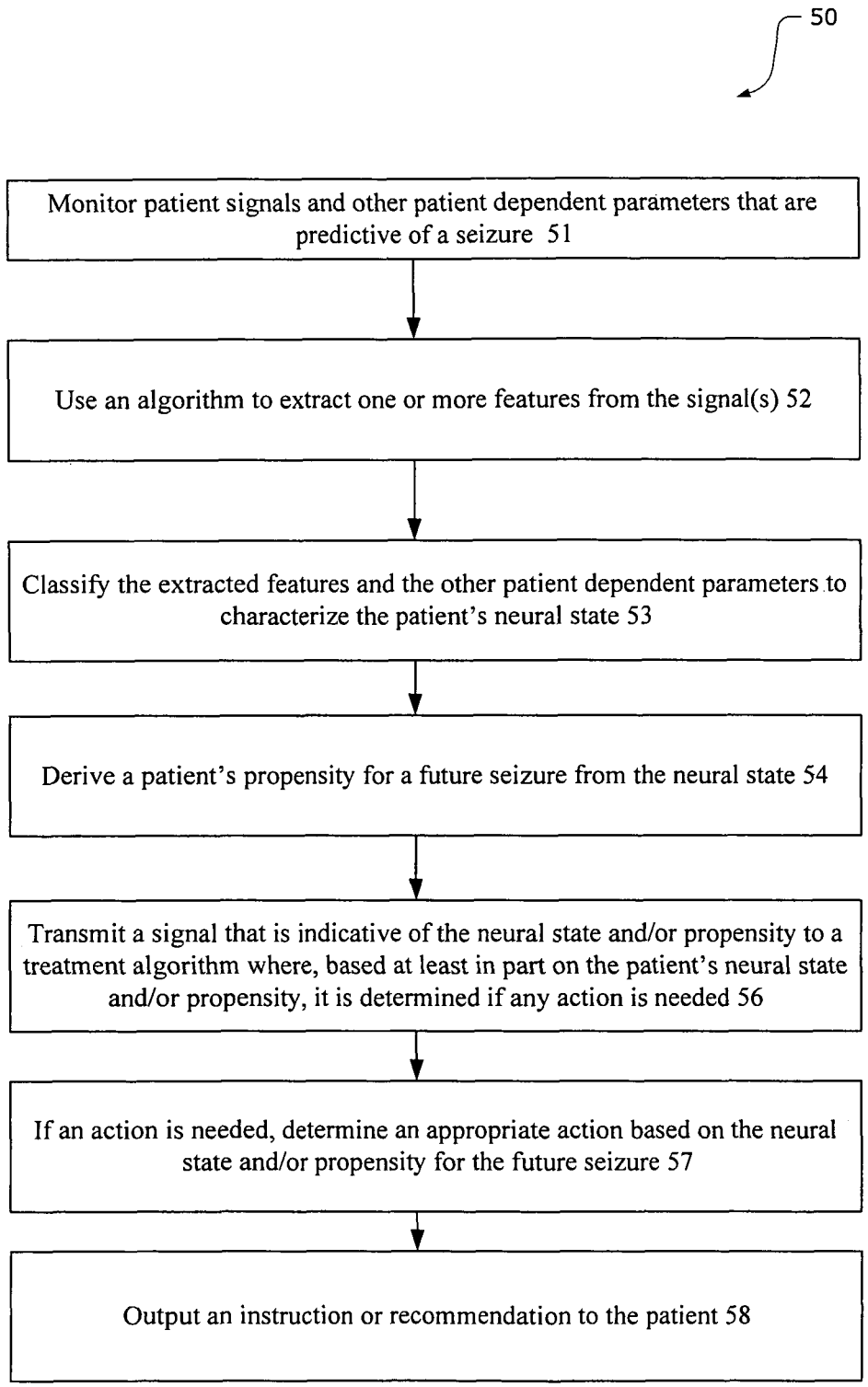
FIG. 6 is a block diagram illustrating another method encompassed by the present invention.

FIG. 6 schematically illustrates a simplified method 50 that is carried out with a system 10 of the present invention. For ease of illustrating data processing, FIG. 6 describes using two separate algorithms that may be run by a processor of the present invention. However, the present invention also encompasses a single algorithm, a combination of hardware and software, and hardware alone that carries out the functionality of the two algorithms described in relation to FIG. 6.

Referring again to FIG. 6, patient signals (neural signals and other physiological signals) and other patient dependent parameters (such as patient inputs and/or patient history data) that are indicative of a patient's propensity for a seizure are monitored (Step 51). Typically, the raw or pre-processed signal(s) from the patient are monitored during a sliding observation window or epoch. The sliding windows may be monitored continuously, periodically during predetermined intervals, or during an adaptively modified schedule (to customize it to the specific patient's cycles). For example, if it is known that the patient is prone to have a seizure in the morning, the clinician may program system 10 to continuously monitor the patient during the morning hours, while only periodically monitoring the patient during the remainder of the day. Similarly, it may be less desirable to monitor a patient and provide an output to a patient when the patient is asleep. In such cases, the system 10 may be programmed to discontinue monitoring or change the monitoring and communication protocol with the patient during a predetermined "sleep time" or whenever a patient inputs into the system that the patient is asleep (or when the system 10 determines that the patient is asleep). This could include intermittent monitoring, monitoring with a varying duty cycle, decreasing of the sampling frequency, or other power saving or data minimization strategy during a time period in which the risk for a seizure is low. Additionally, the system could enter into a low risk mode for a time period following each medication dose. One exemplary method of operating a neurostimulation or drug delivery device during a patient's sleep cycle is described in U.S. Pat. No. 6,923,784

The measured signals are input into a predictive algorithm, where one or more features are extracted (Step 52). The extracted features and the other patient dependent parameters are classified to characterize the patient's propensity for seizure (Step 54). If desired, a neural state index, which is reflective of the patient's propensity for seizure, may be displayed to the patient or caregiver. The neural state index may be a derivative of the patient's propensity for seizure, or a simplified output of measurements performed by the predictive algorithm, and it may be simplified to one or more scalar numbers, one or more vectors, a symbol, a color, or any other output that is indicative of differences in the patient's neural state.

Once the patient's propensity for seizure is characterized by the predictive algorithm, a signal that is indicative of the propensity for the future seizure is transmitted to a treatment algorithm, where, based at least in part on the patient's propensity for seizure, it is determined if any action is needed (Step 56). If an action is needed (e.g., the patient has an elevated propensity for seizure), the appropriate action is determined by the treatment algorithm using the elevated propensity for seizure (Step 57), and a communication is output to the patient that is indicative of the appropriate action for the patient to take (Step 58).

In the simplest embodiment, the predictive algorithm provides an output that indicates that the patient has an elevated propensity for seizure. In such embodiments, the communication output to the patient may simply be a warning or a recommendation to the patient that was programmed into the system by the clinician. In other embodiments, the predictive algorithm may output a graded propensity assessment, a quantitative assessment of the patient's state, a time horizon until the predicted seizure will occur, or some combination thereof. In such embodiments, the communication output to the patient may provide a recommendation or instruction that is a function of the risk assessment, probability, or time horizon.

Figure 7:
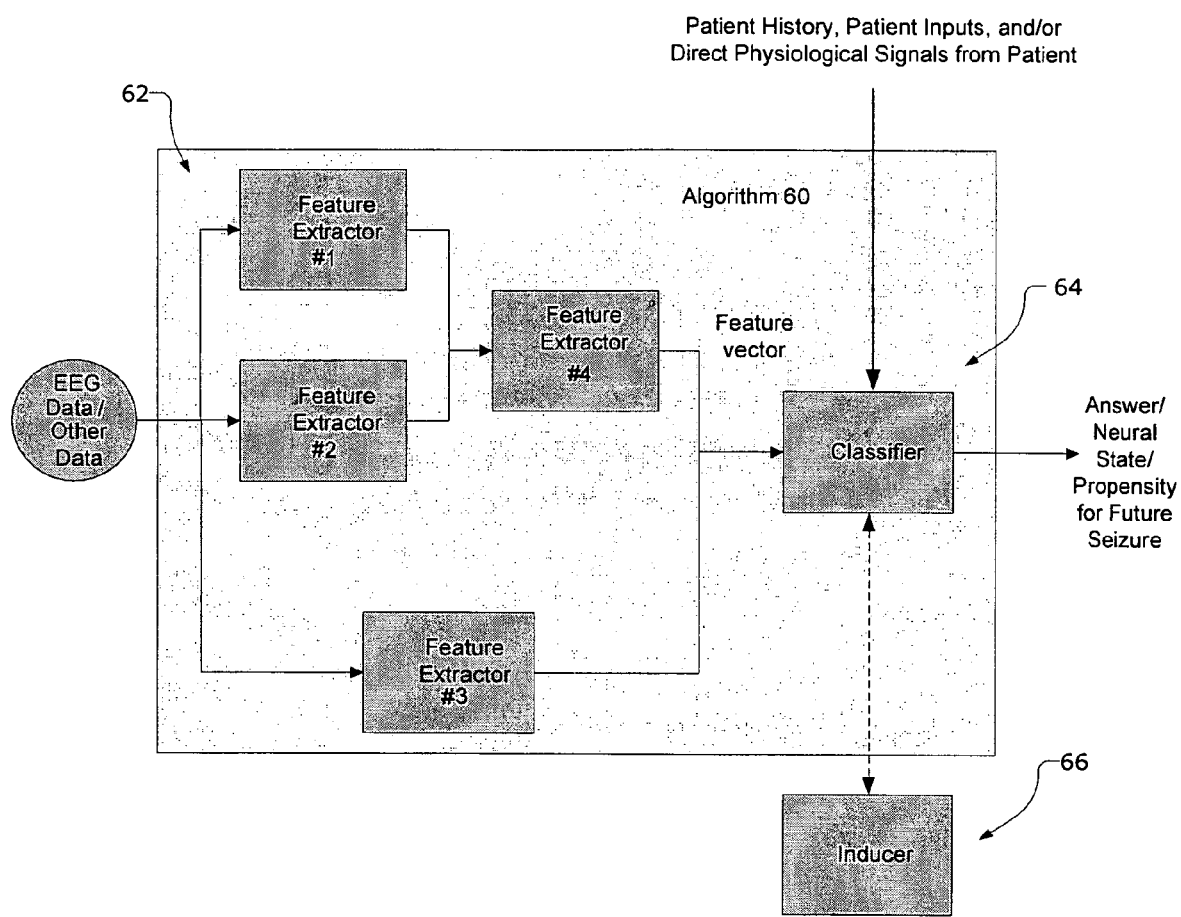
FIG. 7 illustrates a simplified predictive algorithm that may be used by the device assembly of FIG. 5.

FIG. 7 illustrates one embodiment of a predictive algorithm 60 that is encompassed by the present invention. Predictive algorithms 60 are routinely considered to be comprised of arrangements of feature extractors or measures 62, and classifiers 64. Feature extractors 62 are used to quantify or characterize certain aspects of the measured input signals. Classifiers 64 are then used to combine the results obtained from the feature extractors into an overall answer or result. Algorithms may be designed to detect different types of conditions of which neural state may be reflective. These could include but are not limited to algorithms designed to detect if the patient's neural state indicative of an increased propensity for a seizure or algorithms designed to detect deviation from a normal state. As can be appreciated, for other neurological or non-neurological disorders, the patient's neural state will be based on algorithms, feature extractors and classifiers that are deemed to be relevant to the particular disorder.

As shown in FIG. 7, in use, signals from patient interface assembly 14 may be transmitted to predictive algorithm from the patient interface assembly, as described above. The signals may be first pre-processed by the signal conditioning assembly 40 (FIG. 5), or predictive algorithm 60 itself may have a pre-conditioning component (not shown). In one preferred embodiment, the predictive algorithm 60 comprises feature extractors for brain signals (e.g., EEG signals, brain temperature signals, brain blood flow, etc.) that are used to characterize the patient's neural state and feature extractors for other patient parameters (e.g., non-brain, physiological signals, patient history, patient inputs). The predictive algorithm typically uses some combination of the brain signal and other patient parameters to characterize the patient's propensity for seizure, but it may be possible that only the brain signals (e.g., neural state) or only the other patient parameters may be used to characterize the patient's propensity for seizure.

Feature extractors 62 receive the signals and extract various quantifiable features or parameters from the signal to generate an output for classifier 64. Feature extractor 62 may extract univariate and bivariate measures and may use linear or non-linear approaches. While the output from feature extractor 62 may be a scalar, the output is typically in the form of a multivariable feature vector. As shown in FIG. 7, each of the features themselves may be combined with other features and used as inputs for a separate feature extractor. For example, in the illustrated example, the output from Feature Extractor #1 and the output from Feature Extractor #2 are used as inputs into Feature Extractor #4. Any number of different feature extractors may be used to characterize the patient's propensity for a seizure. Different combinations of features and/or different features themselves may be used for different patients to characterize the patient's propensity for the future seizure. Furthermore, it may be desirable to customize the predictive algorithm to the patient so that only selected features are extracted and/or sent to the classifier.

Some examples of potentially useful features to extract from the signals for use in determining the patient's propensity for the seizure, include but are not limited to, alpha band power (8-13 Hz), beta band power (13-18 Hz), delta band power (0.1-4 Hz), theta band power (4-8 Hz), low beta band power (12-15 Hz), mid-beta band power (15-18 Hz), high beta band power (18-30 Hz), gamma band power (30-48 Hz), second, third and fourth (and higher) statistical moments of the EEG amplitudes, spectral edge frequency, decorrelation time, Hjorth mobility (HM), Hjorth complexity (HC), the largest Lyapunov exponent L(max), effective correlation dimension, local flow, entropy, loss of recurrence LR as a measure of non-stationarity, mean phase coherence, conditional probability, brain dynamics (synchronization or desynchronization of neural activity, STLmax, T-index, angular frequency, and entropy), line length calculations, area under the curve, first, second and higher derivatives, integrals, or a combination thereof. Some additional features that may be useful are described in Mormann et al., "On the predictability of epileptic seizures," Clinical Neurophysiology 116 (200) 569-587.

Once the desired features are extracted from the signal 52, the at least some of the extracted features (and optionally other patient dependent parameters, such as patient history, patient inputs, and/or other direct physiological signals from the patient) are input into one or more classifiers 64, where the feature vector (or scalar) is examined so as to classify the patient's propensity for a future seizure (e.g., neural state). The classifier 64 classifies the measured feature vector to provide a logical answer or weighted answer. The classifier 64 may be customized for the individual patient and the classifier may be adapted to use only a subset of the features that are most useful for the specific patients. Additionally, over time, as the system adapts to the patient, the classifier 64 may reselect the features that are used for the specific patient.

In order to provide the classifications for the classifier 64, an inducer 66 may use historical/training feature vector data to automatically train the classifier 64. The inducer 66 may be used prior to implantation and/or may be used to adaptively monitor the neural state and dynamically adapt the classifier in vivo.

Using any of the accepted classification methods known in the art, the measured feature vector is compared to historical or baseline feature vectors to classify the patient's propensity for a future epileptic seizure. For example, the classifier may comprise a support vector machine classifier, a predictive neural network, artificial intelligence structures, a k-nearest neighbor classifier, or the like.

As it relates to epilepsy, one implementation of the classification of states defined by the classifier may include (1) a "normal" state or inter-ictal state, and (2) an "abnormal" state or pre-seizure state (sometimes referred to herein as "pre-ictal state"), (3) a seizure state or ictal state, and (4) a post-seizure state or post ictal state. However, since the primary purpose of the algorithm is to determine if the patient is in a "normal state" or "abnormal state," it may be desirable to have the classifier only classify the patient as being in one of the two most important states—a pre-ictal state or inter-ictal state—which could correspond to a high propensity for a future seizure or a low propensity for a future seizure.

As noted above, instead of providing a logical answer, it may be desirable to provide a weighted answer so as to further delineate within the pre-ictal state to further allow system 10 to provide a more specific output communication for the patient. For example, instead of a simple logical answer (e.g., pre-ictal or inter-ictal) it may be desirable to provide a weighted output in the form of a simplified neural state index (NSI) or other output that quantifies the patient's propensity, probability, likelihood or risk of a future seizure using some predetermined scale (e.g., scale of 1-10, with a "1" meaning "normal" and a "10" meaning seizure is imminent). For example, if it is determined that the patient has an increased propensity for a seizure (e.g., patient has entered the pre-ictal state), but the seizure is likely to occur on a long time horizon, the output signal could be weighted to be reflective of the long time horizon, e.g., an NSI output of "5". However, if the NSI indicates that the patient is in a pre-ictal state and it is predicted that the seizure is imminent within the next 10 minutes, the output could be weighted to be reflective of the shorter time horizon to the seizure, e.g., an NSI output of "9." On the other hand, if the patient's neural state is normal, the algorithm may provide an NSI output of "1".

Another implementation involves expressing the inter-ictal and pre-ictal states as a continuum, with a scalar or vector of parameters describing the actual state and its variation. Such a continuous variable or set of variables can be communicated to the patient, enabling the patient to employ his or her own judgment and interpretation to then guide palliative or preventative behaviors or therapies or the continuous variable or set of variables may be used by the system 10 of the present invention to determine and recommend an appropriate therapy based on the patient's state within the continuum.

Once the classifier has classified the patient's propensity for seizure, (e.g., elevated/pre-ictal or normal/not pre-ictal) the output from the classifier is transmitted to the treatment algorithm, such as a configurable communication state machine (see for example, FIG. 8), where the appropriate action is determined.

The predictive algorithms and treatment algorithms may be embodied in a device that is implanted in the patient's body, external to the patient's body, or a combination thereof. For example, in one embodiment the predictive algorithm may be stored in memory 30 and processed in processor 28, both of which are in a device assembly 12 that is implanted in the patient's body. The treatment algorithm, in contrast, may be processed in a processor that is embodied in an external patient communication assembly 18. In such embodiments, the patient's propensity for seizure characterization (or whatever output is generated by the predictive algorithm that is predictive of the onset of the seizure) is transmitted to the external patient communication assembly, and the external processor performs any remaining processing to generate and display the output from the predictive algorithm and communicate this to the patient. Such embodiments have the benefit of sharing processing power, while reducing the battery usage of the implanted assembly 12. Furthermore, because the treatment algorithm is external to the patient, updating or reprogramming the treatment algorithm may be carried out more easily.

In other embodiments however, both the predictive algorithm and the treatment algorithm may be processed by processor 28 and/or hardware 27 that are implanted within the patient, and an output signal is transmitted to the patient communication assembly 18, where the output signal may or may not undergo additional processing before being communicated to the patient. Such a configuration minimizes the data transmission route and reduces potential bandwidth issues with the telemetry communication between the device assembly 12 and the patient communication assembly. Furthermore, if the appropriate action is automatically facilitated by the device assembly 12, such treatment may be provided even if the patient communication assembly 18 is non-functional or lost.

Alternatively, it may be possible that most or all of the processing of the signals measured by patient interface 14 is done in a device that is external to the patient's body. In such embodiments, the implanted device assembly 12 would receive the signals from patient interface 14 and may or may not pre-process the signals and transmit some or all of the measured signals transcutaneously to an external patient communication assembly 18, where the prediction of the seizure and therapy determination is made. Advantageously, such embodiments reduce the amount of computational processing power that needs to be implanted in the patient, thus potentially reducing power consumption and increasing battery life. Furthermore, by having the processing external to the patient, the judgment or decision making components of the system may be easily reprogrammed or custom tailored to the patient without having to reprogram the implanted device assembly 12.

In yet other embodiments of the present invention, it may be possible to perform some of the prediction in the implanted device assembly 12 and some of the prediction and treatment determination in an external device, such as the patient communication assembly 18. For example, one or more features from the one or more signals may be extracted with feature extractors in the implanted device assembly 12. Some or all of the extracted features may be transmitted to the patient communication assembly, where the features may be classified to predict the onset of a seizure. Thereafter, an appropriate action (if needed) may be determined by the treatment algorithm (which may be stored in the device that is implanted in the patient's body or in a device that is external to the patient's body). If desired, patient communication assembly 18 may be customizable to the individual patient. Consequently, the classifier may be adapted to allow for transmission or receipt of only the features from the implanted device assembly 12 that are predictive for that individual patient. Advantageously, by performing feature extraction in the implant and classification in the external device at least two benefits may be realized. First, the wireless data transmission rate from the implanted device assembly 12 to the patient communication assembly 18 is reduced (versus transmitting pre-processed data). Second, classification, which embodies the decision or judgment component, may be easily reprogrammed or custom tailored to the patient without having to reprogram the implanted device assembly 12.

In yet another embodiment, it may be possible to switch the positions of the classifier and the feature extractors so that feature extraction may be performed external to the body. Pre-processed signals (e.g., filtered, amplified, conversion to a digital signal) may be transcutaneously transmitted from device assembly 12 to the patient communication assembly 18 where one or more features are extracted from the one or more signals with feature extractors. Some or all of the extracted features may be transcutaneously transmitted back into the device assembly 12, where a second level of processing may be performed on the features, such as classifying of the features (and other signals) to characterize the patient's propensity for the onset of a future seizure. Thereafter, the patient's propensity for the future seizure or other answer may be transmitted to the treatment algorithm (which may be in the device assembly 12 or the patient communication assembly 18) to determine an appropriate action (if needed). If desired, to improve bandwidth, the classifier may be adapted to allow for transmission or receipt of only the features from the patient communication assembly that are predictive for that individual patient. Advantageously, because feature extractors may be computationally expensive and power hungry, it may be desirable to have the feature extractors external to the body, where it is easier to provide more processing and larger power sources.

Figure 8:
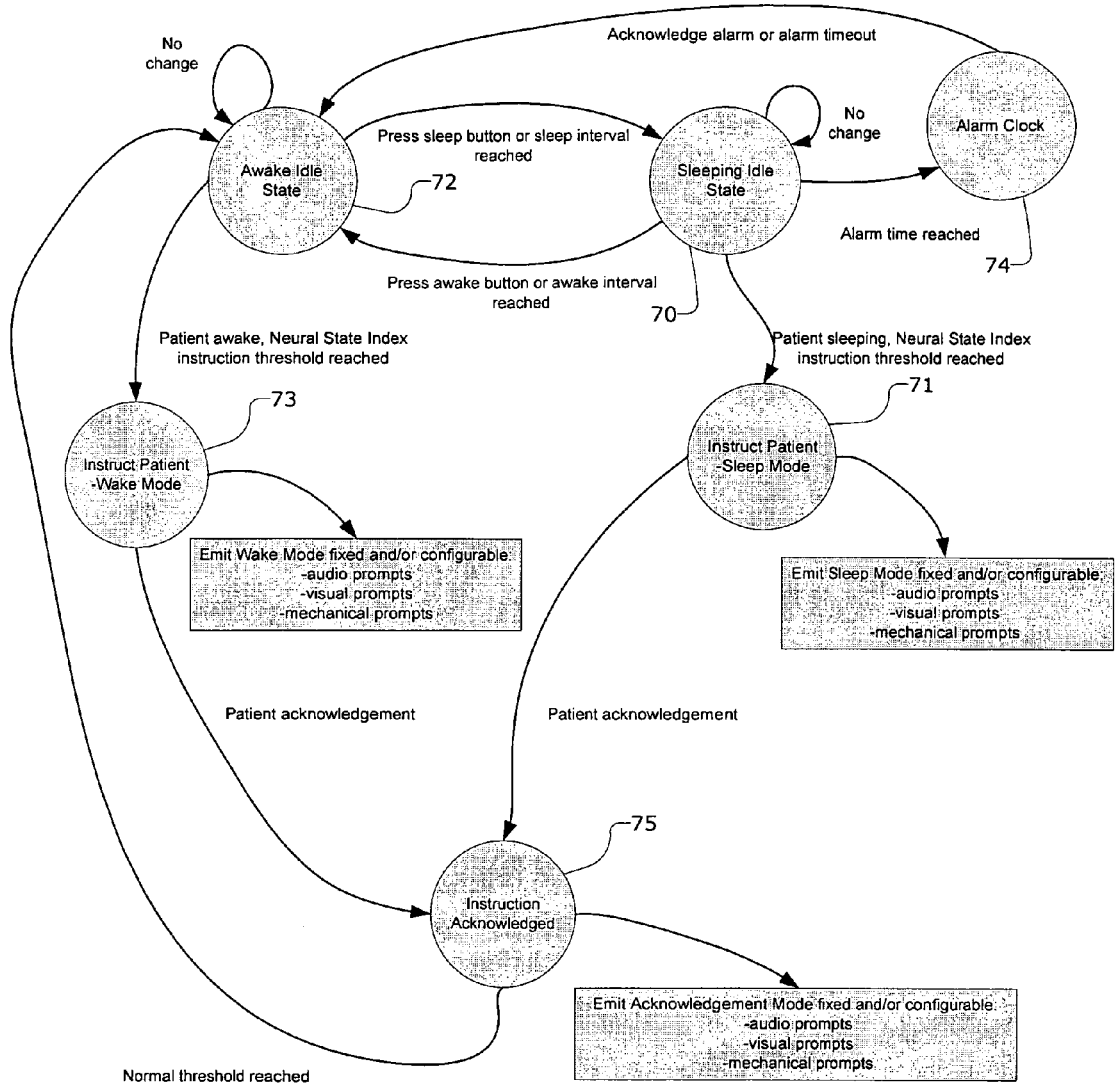
FIG. 8 illustrates an embodiment of a configurable communication state machine that may be used by the patient communication assembly of FIG. 7.

FIG. 8 shows one example of a state machine that may be used with the present invention. As shown in FIG. 8, a configurable communication state machine is responsive to the Neural State Index or other output of the predictive algorithm, patient inputs and other variables such as time-of-day. The outputs from the configurable communication state machine may vary depending on the machine state. Some output behaviors may be fixed, and some output behaviors may be configurable. For example, a clinician could configure a different set of prompts for a patient who is considered to be sleeping 70 than for when the same patient is considered to be awake 72. Moreover, the clinician can program a different set of prompts depending on any of the patient dependent parameters. For example, if the patient indicates that they recently had an aura, the configurable state machine may be adapted to vary the machine state and provide different sets of prompts or thresholds.

In the illustrated example, a standard mode for the state machine in which the patient's propensity for seizure is monitored is an Awake Idle State 72. If and when the patient's propensity for seizure reaches one or more thresholds that are indicative of an elevated propensity of a seizure, the state machine moves to an "Instruct Patient—Wake Mode" 73 in which a fixed and/or configurable instruction is communicated to the patient depending on the patient's characterized propensity for seizure (see FIG. 8). The instruction may take the form of an audio prompt, a visual prompt, a text prompt, a mechanical prompt, or a combination thereof. As described herein, the instructions may recommend that the patient take an acute dosage of an AED or other pharmacological agent, activate a vagus nerve stimulator or other stimulator, activate a thermal cooling device, make themselves safe, or the like. The instructions will continue until the patient acknowledges the instruction. The state machine will continue monitoring the patient's propensity for seizure to register any change in propensity for seizure (resulting from implementation of the instructions or otherwise) and to determine whether any further instructions are required. Optionally, once the patient acknowledges the instruction 75, the state machine may emit an acknowledgement mode fixed and/or configurable output to the patient. Such acknowledgement output may be an audio prompt, visual prompt, text prompt, mechanical prompt, or a combination thereof.

As shown in FIG. 8, it may be desirable to change from an Awake State to a Sleep State. For example, some patient's may have more frequent seizures during their sleep cycle, while other patients may have fewer seizures during their sleep cycle. Thus for the different patients it may be desirable for the clinician to customize the types of communication provided to the patient, the specific instructions provided to the patient, the frequency of monitoring the propensity for seizure during the patient's sleep cycle, or the like. Thus, in the illustrated embodiment, if the patient is going to sleep and activates a sleep button or if the state machine determines that the patient is sleeping, the state machine enters the Sleeping Idle State 70. When the patient is sleeping and the patient's propensity for seizure measurement reaches one or more defined thresholds that are indicative of a higher propensity for a future seizure (which may be the same thresholds or different thresholds from the Awake Idle State 72), the state machine may enter an "Instruct Patient—Sleep Mode" 71, in which a fixed and/or configurable instruction is provided to the patient. The instruction to the patient may include an audio prompt, visual prompt, text prompt, mechanical prompt, or a combination thereof. Similar to the Instruct Patient—Wake Mode 73, when the state machine is in the Instruct Patient—Sleep Mode 71, the instructions will continue until the patient acknowledges the instruction. Once the patient acknowledges the instruction 75, the state machine may return to the Awake Idle State 72.

If the patient awakes from sleep, the patient may press an awake button or other input device on the patient communication assembly 18 to change the state machine from the Sleeping Idle State 70 to the Awake Idle State 72. Alternatively, the state machine may be programmed to change to the Awake Idle State 72 when an awake interval is reached. Optionally, an alarm clock 74 may be integrated as a method for further ascertaining whether or not the patient is asleep. Furthermore, the state machine may itself automatically transition from a Sleeping Idle State 70 to and Awake Idle State 72 when certain conditions are present. In the Sleeping Idle State, a low-power mode may calculate an approximation of the propensity for seizure, and if certain ranges or behaviors of the propensity for seizure are detected, then the system may automatically transition from the Sleeping Idle State 70 to the Awake Idle State 72, where the "full power" mode may be used to characterize the patient's propensity for seizure.

While the configuration communication state machine of FIG. 8 is one embodiment for providing an instruction or recommendation to the patient based on the patient's propensity for seizure, in other embodiments, a treatment algorithm may be embodied in an embedded microprocessor to process linear or nonlinear control laws and may also use the output from the predictive algorithm to provide a communication output to the patient and/or generate or adjust a magnitude of the therapy (e.g., an electrical stimulation signal or the type or amount of medication delivered). Some examples of useful means for generating the therapy or output to the patient may be found in commonly owned U.S. Pat. Nos. 6,366,813 and 6,819,956.

It is contemplated that the predictive algorithms and treatment recommendations specified by the clinician are likely to be customized for each individual patient. As such, the number and/or type of features extracted, the, the classifier, the types of treatment prescribed will likely be customized for the patient. Moreover, it may be desirable to have the predictive algorithm adapt to the patient over time, and modify the feature extractors to track the patient's propensity for seizure changes over time.

While FIGS. 7-8 illustrate exemplary algorithms of the present invention, a variety of other predictive algorithms and treatment algorithms may be useful with the systems 10 of the present invention to predict the onset of an epileptic seizure. Some examples of other useful detection or prediction algorithms include those described in U.S. Pat. No. 3,863,625 to Viglione, U.S. Pat. No. 6,658,287 to Litt, U.S. Pat. No. 5,857,978 to Hively, and U.S. Pat. No. 6,304,775 to Iasemidis, U.S. Pat. No. 6,507,754 to Le Van Quyen et al., U.S. Pat. No. 6,594,524 to Esteller et al. Any of such detection and prediction algorithms may be used by system 10 of the present invention to produce an output that may be used by the treatment algorithm to determine the communication (e.g., recommendation or instruction) that is output to the patient. For example, one or more probability outputs or time horizons of Litt's '978 algorithm may be used to determine the appropriate action output that is provided to the patient. Thus, while the above description describes using a neural state to characterize the patient's propensity for a future seizure, any of the outputs provided by the prediction algorithms described in the aforementioned patents may be used to characterize the patient's propensity for the future seizure.

Figure 9:
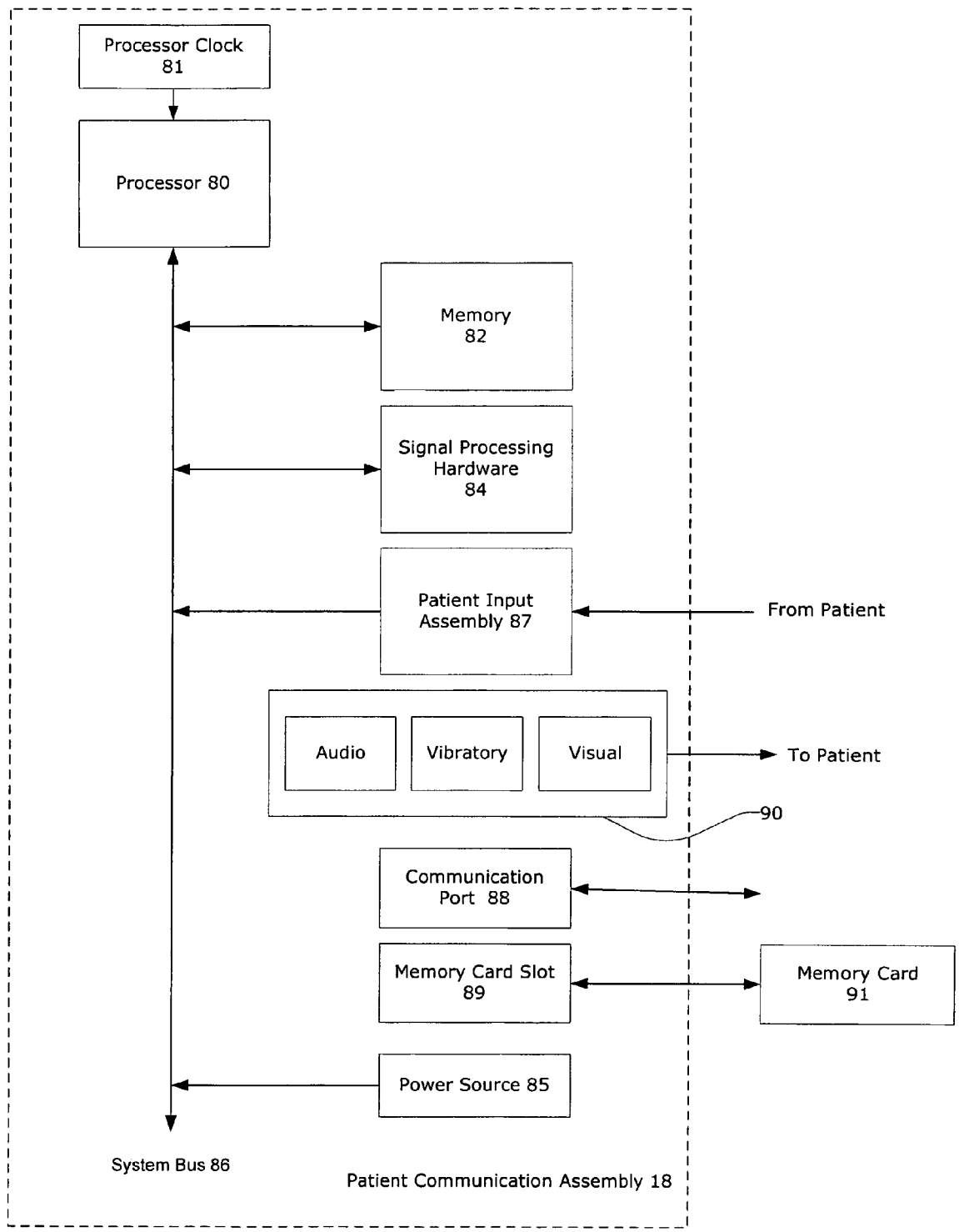
FIG. 9 illustrates a block diagram of a patient communication assembly of the present invention.

FIG. 9 schematically illustrates a patient communication assembly 18 of the present invention that may house a portion of or all of the algorithms of the present invention and/or provide the output communication to the patient. Patient communication assembly 18 will typically be in the form of an external, handheld device. If desired, the patient communication assembly 18 may be integrated with other handheld devices, such as a cellular phone, pager, personal digital assistant (PDA), glucose monitor, MP3 or other audio or video player, wristwatch, portable gaming device, or the other handheld devices. However, as can be appreciated, the patient communication assembly 12 does not have to be handheld and may be incorporated into a personal computer or workstation.

Patient communication assembly 18 generates the output to the patient using software, hardware, or a combination thereof. Patient communication assembly 18, typically comprises one or more processors 80, a processor clock 81, one or more permanent or removable memory modules 82 (e.g., RAM, ROM, EEPROM, flash memory, or the like), dedicated signal processing hardware 84, and a power source/battery 85. A system bus 86 may provide a communication path and power path for the various components of patient communication assembly 18. Memory modules 82 may be use to store one or more algorithms used by patient communication assembly 18 and/or to store data transmitted from signal processing device 12. In addition to memory modules, patient communication assembly 18 may comprise a memory card slot 89 for receiving a removable memory card 91, such as a flash memory stick.

A patient input assembly 87 allows a patient to communicate with processor 80 and device assembly 12. Patient communication assembly 18 may include any number of patient inputs that allows the patient to query device assembly 12 and to provide inputs into system 10. Some useful inputs include buttons, levers, switches, touchscreen, touchpad, joystick, wheel, dial, an alphanumeric keypad, or the like. User inputs may be used by the patient to turn off an alarm, activate therapy (e.g., manually activate electrical stimulation or drug delivery), indicate that a pharmacological agent has been taken, scroll through menus, provide an indication to system 10 that a seizure is occurring or about to occur, or the like.

Advantageously, the present invention will allow the patient to provide inputs to provide patient feedback into system 10 that may be used by the prediction algorithm 60 (FIG. 7) as a "feature" to improve the characterization of the patient's propensity for the future seizure. Additionally, the inputs provided by the patient may be stored in memory 82 and used as a "diary" to allow for later analysis by the clinician and/or device assembly. Additional information that may be input include patient state, such as sleep deprivation, exposure to or "withdrawal" from alcohol or other medications, physiological or emotional stress, presence or absence of antiepileptic drugs (AEDs) or other medications, start of menstrual cycle, or the like. Since many patients have auras prior to having a seizure, the input from the patient into the system that indicates that an aura is occurring may be used by algorithm 60 to characterize the patient's propensity or by the treatment algorithm to determine the appropriate treatment.

Patient communication assembly 18 may include one or more communication ports 88 that facilitate communication with the device assembly 12. The data from device assembly 12 is preferably transmitted substantially in real time from the device assembly 12 to the patient communication assembly 18. Communication port 88 provides for one-way or two way transcutaneous communication with the implanted device assembly 12 through conventional wireless communication protocols, such as through telemetry, radiofrequency, ultrasonic, optical, or magnetic communication protocols.

Communication port 88 may further facilitate wireless or wired communication with other external devices or networks. For example, the communication port may be used to communicate with clinician communication assembly 20, a LAN, a WAN, the Internet, a local or remote server/computer 26, or the like (FIG. 2). Communication with a network would allow for downloading of patient history data (e.g., neural state, medication intake, etc.) to a remote server for future or substantially real-time review by a clinician or the patient's guardian. Furthermore, software updates or parameter changes for the patient communication assembly 18 or the signal processing device 12 may be transmitted and uploaded to the system 10 via communication port 88.

Patient communication assembly 18 will comprise a patient output assembly 90 that includes one or more output mechanisms for communicating with the patient. Patient output assembly 90 may include an audio mechanism, a vibratory mechanism, a visual mechanism (e.g., LEDs, LCD, or the like), or any combination thereof. Patient communication assembly 18 will be programmed to deliver a plurality of different outputs to the patient, in which each of the different outputs will be reflective of either a different propensity for seizure or a different action that the patient should take. For example, it may be desirable to provide different patterns or intensities of beeps, flashing lights or vibrations to be indicative of different propensity for seizures or neural states. Some examples of different outputs that may be provided to the patient are described more fully below.

In some embodiments, patient communication assembly 18 may include a charging assembly (not shown) for charging the power source 85 of the implanted device assembly 12. The charging assembly may be placed above or against the patient's skin where the device assembly is implanted and activated to interact with the recharging communication interface to charge the power source 85. Of course, in other embodiments, the external recharging assembly may be a separate device.

While not shown in FIG. 9, a clinician communication assembly will typically have similar or a superset of the components in the illustrated patient communication assembly 18. A significant difference between the patient communication assembly 18 and the clinician communication assembly is that the clinician communication assembly 20 may be used as a programmer that allows a clinician or supervisor to reprogram device assembly 12. The clinician may update the software of device assembly 12, update the treatment algorithm, change the parameters of the recommended therapies, change the outputs provided to the patient, change the clinician defined recommendations/instructions, or the like. Clinician communication assembly 20 does not have to be a handheld device, and it may be desirable to allow the clinician to monitor a variety of different patients with a single device. Consequently, it may be desirable to have the clinician communication assembly be in the form of a personal computer or other device that is able to communicate with patient communication assembly 18.

When communication with the implanted device assembly 12 is desired, a programming device, such as clinician communication assembly 20 is brought into a communication range with the device assembly 12 or the patient communication assembly 18. This may be achieved simply by placing the programming device above or against the patient's skin where the device assembly 12 is implanted in the patient. The communication port of the clinician communication assembly 20 transmits data to and from the communication port 44 of device assembly 12 via conventional wireless protocols, such as telemetry, inductive links, magnetic links, RF links, infrared links, optical links, ultrasound links, or the like. Alternatively, it may be possible to provide for indirect communication with implanted device assembly 12 via the patient communication assembly 18. Reprogramming of device assembly 12 may be indirectly achieved by sending programming instructions from the clinician communication assembly 20 (or personal computer 26 (FIG. 2)) to the patient communication assembly 18 through a wired or wireless communication link. Thereafter, the programming data may be transmitted wirelessly from patient communication assembly 18 to the device assembly 12 using conventional protocols or any of the communication protocols described above.

In certain embodiments, it may be possible to automatically contact the patient's clinician with the device assembly 12 and/or patient communication assembly 18. For example, if a specified threshold is reached, a seizure of sufficient duration has occurred, a sufficient quantity of seizures has occurred, a maximum amount of pharmacological agent has been taken within a predetermined time period, or an undesirable state is reached, the patient communication assembly 18 may initiate a communication link (e.g., a call, email, text message, etc.) to the clinician communication assembly 20 or other remote server. If desired, the communication may include the patient's neural state data, propensity for seizure, instructions provided to the patient, pharmacological agent intake, or any other data generated or stored by system 10. Such a communication may take place in real time, or within a delayed time period that would still allow the patient and/or clinician to take the appropriate action.

While the patient communication assembly illustrated in FIG. 9 comprises a plurality of digital components, the present invention is not limited to such a configuration, and the patient communication assembly may be carried out with a different combination of components, e.g., different components, additional digital components, fewer digital components, a combination of digital components and analog circuitry, solely analog circuitry, or the like.

Figure 10:
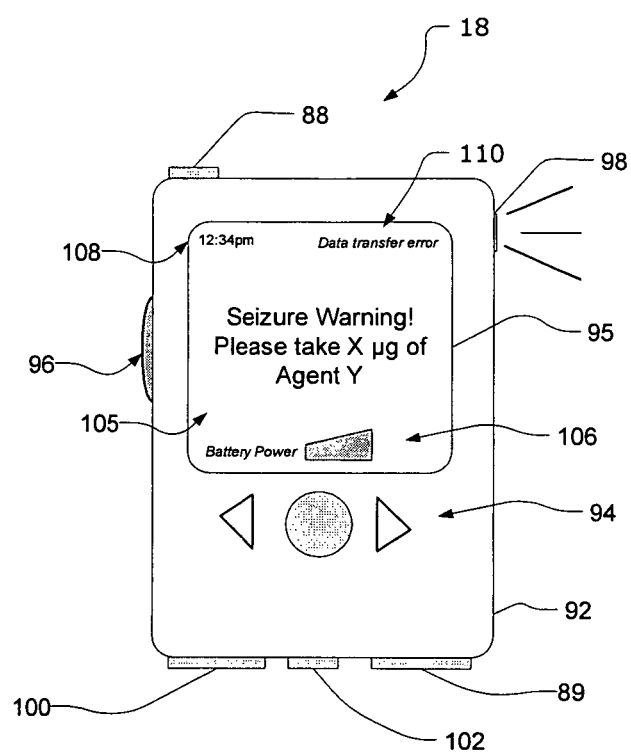
FIG. 10 illustrates an embodiment of a patient communication assembly that may be used to provide an instruction to the patient regarding an appropriate action.

FIG. 10 illustrates one embodiment of a simplified handheld patient communication assembly 18 that is encompassed by the present invention. Patient communication assembly comprises a housing 92 that is sized and shaped to be held in a patient's hand. Housing 92 includes a patient input assembly that comprises one or more input devices. In the illustrated embodiment, the patient communication assembly comprises a plurality of buttons 94, a touch screen 95, and a scroll wheel 96 that allows a patient to provide inputs into system 10, query device assembly 12, scroll through display menus, and the like. Communications to the patient may be provided to the patient through patient output assembly, which includes the touch screen display 95, speaker 98, and a vibration mechanism (not shown). Patient communication assembly 18 will typically have the following communication ports—a charging port 100 coupled to the power source, a USB port 102 or other port for providing wired or wireless communication with a host computer, and communication port 88 for communicating with the implanted device assembly 12. Optionally, patient communication assembly may comprise slot 89 for receiving a removable memory, such as a flash memory stick.

As shown in FIG. 10, patient communication assembly 18 preferably provides a visual communications to the patient via screen 95, but as can be appreciated it may be desirable to provide an auditory, vibratory or other output in addition to or as an alternative to the visual display. Screen 95 may display to the patient an output 105 that is indicative of the appropriate action to take. Display 95 may also be used to display other data to the patient, such as battery power 106, time 108, error messages 110, or the like. While not shown, patient communication assembly 18 may comprise a menu driven interface that allows the patient to toggle from a home screen display to other display screens. Such an interface would allow the patient to access other menus and sub-menus that have additional information that the patient may find desirable. Such a menu structure would allow more advanced users to access more detailed information, while providing less advanced users a display of the most relevant information on the home screen. For example, the sub-menus may include historical information on the patient's drug intake, estimations of the drug plasma levels, number of seizures over a time period, duration of seizures, the patient's real-time neural state, propensity for seizure, a time history of the patient's neural state, other information relating to neural state and response to therapy, and the like. If desired, the menu interface may be customizable to suit the patient's preferences. The communication assembly 18 may also provide information to the patient relating to the estimated effect or response to chronic or acute therapy and may make adjustments to these recommendations including recommendations for augmentative or supplementary therapy, with the same or additional medications or other modalities. Recommendations for behavioral modification may also be provided, these including recommendations to avoid hazardous activities such as driving or operating machinery or cooking, to sit in a quiet dark room, to rest, or to avoid walking outside or going to work that day.

The output 105 that is indicative of the appropriate action may specify any number of different actions, depending on the output from the predictive algorithm and therapy regimen prescribed by the clinician. In most cases, the therapy regimen prescribed by the clinician will include the use of one or more pharmacological agents, such as an anticonvulsant or anti-epileptic drug. As such, in the simplest embodiment, when system 10 determines that the patient has an elevated propensity for a seizure, patient communication assembly 18 may provide a warning, and the patient will know to take a certain dosage of a specified pharmacological agent. In preferred embodiments, however, the patient communication assembly 18 outputs a communication which recommends that the patient take one or more pharmacological agents and may specify the dosage or other parameters of the pharmacological agent.

In embodiments where the predictive algorithm is able to provide a weighted answer and provide a greater specificity regarding the pre-ictal state (e.g., the NSI), the output to the patient may also be indicative of a graded response, such as the dosage, form, formulation, and/or route of administration for the pharmacological agents. Depending on the output from the predictive algorithm, the patient communication assembly may recommend that the patient take a lower than normal dosage (e.g., ½ a normal dosage), a normal dosage or a higher than normal dosage (e.g., 2× the normal dosage) of a pharmacological agent. For example, if the patient's propensity for a seizure (or probability for a seizure) is low and/or there is a long predicted time horizon before the seizure occurs, depending on the clinician's and patient's preference, the patient communication assembly 18 may be configured to output a recommendation that the patient to take a lower than normal dosage of a pharmacological agent or a milder type of pharmacological agent that has less severe side effects than the patient's primary pharmacological agent(s). However, if the lower than normal dosage of the pharmacological agent or the milder pharmacological agent, either of which may be considered to be a "preventative dose", does not reduce the patient's propensity for the seizure and the patient continues to trend toward a seizure, (or if the system initially determines a high propensity or probability of a seizure or a short time horizon for the seizure) the patient communication assembly 18 may output a recommendation that the patient take a more severe action, such as taking an additional dose or a higher than normal dosage of the pharmacological agent or a more potent type of pharmacological agent.

In addition to prescribing a dosage of the pharmacological agent, the output to the patient may also specify a time for taking the pharmacological agent and/or a form of the pharmacological agent. If system 10 determines that there is a moderate propensity, moderate probability of a seizure, or there is a long predicted time horizon before the next seizure will occur the patient may be instructed to take a slower acting pharmacological agent or a slower acting form of a pharmacological agent within a specified time period (e.g., within the next 20 minutes). On the other hand, if system 10 determines that there is a high propensity of seizure, high probability of a seizure, or if the predicted time horizon is short, the patient may be instructed to take a faster acting type of pharmacological agent or a faster acting form of a pharmacological agent within a shorter specified time period (e.g., within the next 5 minutes). Such faster acting pharmacological agents may include sublingual medications, intranasal medications, intramuscular injections, intravenous injections, or other injections or routes of administration.

The output to the patient is not limited to recommending or instructing the patient to take a pharmacological agent. An instruction to perform any accepted means for managing or treating epileptic seizures may be output to the patient. For example, if the seizure is imminent and is likely not to be averted with electrical stimulation or pharmacological agents, the communication device 18 may warn the patient of the imminent seizure and simply instruct the patient to "make themselves safe." This would allow the patient to stop driving, lie down, stop cooking, or the like. Some additional instructions or outputs that may be provided to the patient include, but are not limited to, turning off lights, interrupting work, touching the face, hyperventilating, hypoventilating, holding breath, performing the valsalva maneuver, applying an external stimulator (e.g., lights, electrical stimulation, etc.), applying transcutaneous electrical neurostimulation, applying tactile stimulation, activating an implanted deep brain neurostimulator, activating an implanted vagus nerve stimulator, activating another neuromodulator, activating an implanted drug pump, begin taking one or more medications, stop taking medications, increase or reduce medication dosage, change medication dosing regimen, and other initiation of action, change of behavior, or cessation of activity.

Figure 11:
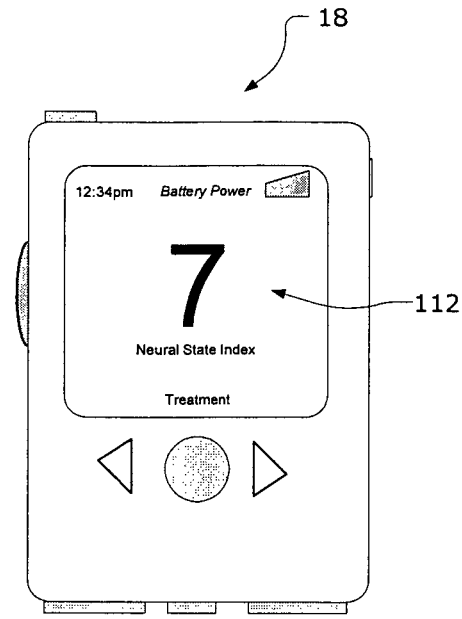
FIG. 11 illustrates an embodiment of a patient communication assembly that displays a patient's neural state index to the patient.

In addition to or as an alternative to the output that is indicative of the appropriate action, the systems of the present invention may provide a variety of other types of outputs to the patient via the patient communication assembly 18. While preferred embodiments provide a communication output to the patient that is indicative of an appropriate action for the patient to take, it may be desirable to merely provide the patient with different warnings that are indicative of the patient's propensity for a seizure or the neural state index. For example, as shown in FIG. 11, it may be desirable to simply display the patient's neural state index 112 that is characterized by the predictive algorithm. The patient's neural state index is preferably displayed in a simplified scalar form and is updated substantially in real time, but a delay may be acceptable, as long as the delay is shorter than the predicted time horizon for the seizure.

While not as straight forward as an instruction to the patient, over time the patient will begin to understand and correlate the neural state information to their particular condition, and the patient will be able to determine or fine tune the appropriate treatment on their own. For example, a patient may know that anytime they have a headache or a specific taste in their mouth and their neural state index stays at level "8" for more than five minutes that a seizure will likely occur sometime that day. Consequently, the patient will know to take an appropriate medication or actuate some sort of treatment to manage or curtail the impending seizure. Furthermore, if the patient's neural state indicates an increased propensity for a seizure, but the patient knows that the neural state measurement may have been affected because the patient hasn't been sleeping or has recently taken an agent that may affect the neural state (e.g., medication, alcohol, etc.), based on the patient's past experiences, the patient may be able to recognize whether or not they actually have an increased risk of a seizure or not.

Figure 12:
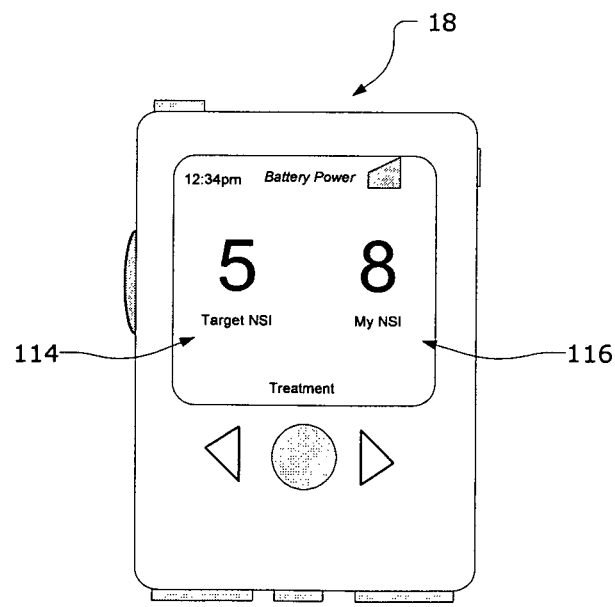
FIG. 12 illustrates an embodiment of a patient communication assembly that displays a patient's target neural state and the patient's measured neural state.
Figure 13:
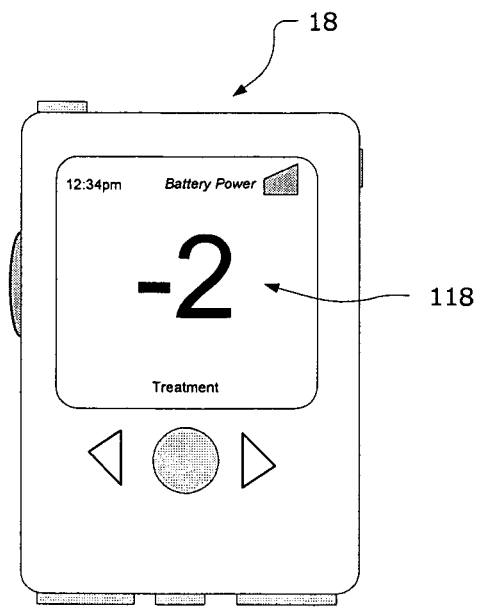
FIG. 13 illustrates an embodiment of a patient communication assembly that displays the difference between the patient's measured neural state and the patient's target neural state.
Figure 14:
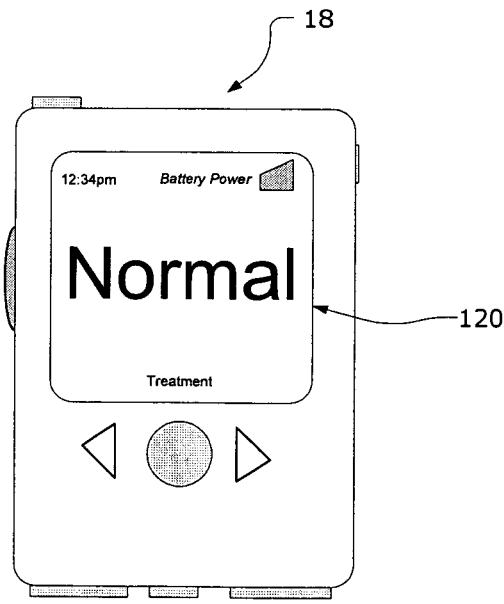
FIG. 14 illustrates an embodiment of a patient communication assembly that displays an alert level to the patient. The illustrated alert level is "normal".

FIGS. 12 to 14 illustrate some additional embodiments of the present invention that illustrate different communication outputs that may be provided to the patient. For ease of reference, the instructions to the patient are not illustrated in the embodiments, but it should be appreciated that the embodiments of FIGS. 12 to 14 may also include instructions that are indicative of the appropriate action. Furthermore, while not described in detail below, instead of displaying the neural state information as an alphanumeric character on an output display of the patient communication assembly 18, the neural state information may be communicated to the patient via other displays (graphs, pie charts, bar charts, line charts, bar displays, etc.) or through other output means, such as differing patterns of vibrations, lights, beeps, rings, voice, or other analog or digital outputs.

FIG. 12 illustrates an embodiment in which a "target" or desired neural state index 114 is shown alongside the patient's measured neural state index 116. Similar to a heart rate monitor, which illustrates a target heart rate and the actual heart rate, this embodiment would allow the patient to know where their neural state index is relative to their target neural state index (or target neural state index range), and would allow the patient to take the appropriate action to move the patient's neural state index toward the target neural state index. As can be appreciated, the patient's target neural state index will likely be pre-determined and programmed into the memory of the system 10 by a clinician and the target neural state will likely vary from patient to patient. Moreover, the target neural state index may vary over time, with such parameters as whether the patient is sleeping or awake, the type or amount of antiepileptic drug or other medication the patient is on, or other factors.

As shown in FIG. 13, in another embodiment, it may be useful to merely show the difference 118 between the patient's target neural state index and the patient's measured neural state index. The output may be a +/–"X" over a target range or target neural state index. Depending on the scalar and the sign of the scalar, the patient should be able to determine the appropriate action needed (if any). For example, if the patient's neural state index is within a normal range, the output provided to the patient would be "0". If a large negative number is shown, such a number may indicate that the patient is overmedicated and no more medication should be taken. On the other hand, a small positive number may indicate that treatment is needed; if a large positive number is shown, such a number may indicate that a seizure is imminent and that the patient should make themselves safe.

FIG. 14 illustrates an embodiment which is configured to provide a variety of different alert levels 120. Generally, the alert levels are based at least in part on the measured propensity for seizure or other output provided by the predictive algorithm. For example, while the propensity for seizure characterizations of the present invention may be simplified down to a scalar between 1-100 (or any other scale), such a scalar may be difficult for some patients to comprehend. To make things easier for the patient to understand, system 10 may be configured to provide for a variety of different "alert levels" that correspond to different propensities for seizure. The patient communication assembly 18 will be capable of producing outputs that correspond to the alert levels.

For example, a patient's propensity for a seizure or neural state index that is below a lower threshold could be indicative of some degree of over-medication and could correspond to alert level one and the patient communication assembly could display an "over-medicated" output. A propensity for seizure or neural state index between a lower threshold and an upper threshold could indicate "normal" or "desired state" and correspond to alert level two. A propensity for seizure or neural state index above a first upper threshold could indicate mild under-treatment or mild worsening in the patient's condition, and could correspond to alert level three. Finally, a propensity for seizure or neural state index above a second, higher threshold could indicate a severe worsening in the patient's condition (and an imminent seizure), and could correspond to alert level four. The output to the patient may include a display on the output display 95 (e.g., alert 1/over-medicated, alert 2/normal, alert 3/action needed, or alert 4/immediate action needed), symbols, charts, colors, patterns of sounds or vibrations, or a combination thereof.

While the above example provides four different levels, the present invention is not limited to four alert levels. Other embodiments of the present invention may have as little as two levels (e.g., normal level and pre-ictal or abnormal level), or any desired number of different alert levels (e.g., greater than four alert levels).

The patient communication assembly 18 may only allow for viewing one of the display types shown in FIGS. 10-14 or the patient may be allowed to select the type of output that is displayed or otherwise provided by the patient communication assembly 18. Thus, the patient may be allowed to toggle between the displays illustrated in FIGS. 10-14. For example, as shown in FIGS. 11-14, if some form of the neural state index or alert level is displayed to the patient, the patient communication assembly 18 may allow the patient to actuate an input 94 to display the treatment that corresponds to the displayed neural state or alert level. Typically, actuation of the input 94 would display an instruction similar to the display shown in FIG. 10.

For any of the above embodiments, the patient communication assembly 18 may be configured to provide a predetermined, variable, or adaptive output that informs the patient of any important changes in the patient's propensity for a future seizure. Typically, the output to the patient may be in the form of a predetermined vibration pattern or ring pattern that indicates to the patient that the patient's condition has changed or that a specific threshold has been crossed. This would allow the patient to monitor their condition without having to require the patient to physically look at the display on the patient communication assembly 18. Additionally, if the situation becomes more critical, the system 10 may be configured to cause the implanted device assembly 12 to vibrate or provide some other type of perceptible output. Typically, the output is provided with output assembly 35 (FIG. 5).

In addition to providing an output to the patient through patient communication assembly 18 that is indicative of the patient's propensity for a future seizure or recommendation regarding the appropriate action, the system 10 of the present invention may be configured to automatically deliver a preventative therapy to the patient. As an initial attempt to prevent a predicted seizure from occurring, the system 10 may automatically deliver an electrical stimulation or other treatment, such as drug infusion, to the patient through an implanted patient interface assembly 14'. Optionally, a warning may be provided on patient communication assembly 18 that informs the patient of the elevated propensity for seizure System 10 may be configured to provide a warning communication to the patient that informs the patient that stimulation is being provided or that an implanted drug pump has been activated so that the patient is aware of the situation. As described above, the characterized propensity for the future seizure, may be used to determine the parameters of the electrical stimulation, drug therapy, or other therapy. Electrical stimulation may be provided substantially continuously in an open-looped fashion or it may be used acutely in a closed-loop fashion to maintain the patient's propensity for seizure in a desirable range. Suitable systems for generating an electrical stimulation therapy based on a measured state of the patient are described in commonly owned U.S. Pat. Nos. 6,366,813 and 6,819,956.

The present invention may also be used for evaluating pharmacological agents and for selecting appropriate pharmacological agents for managing or treating the patient's neurological disorder (e.g., epilepsy). Generally, the methods of the present invention will use the predictive algorithm 60 described above, but other conventional or proprietary means to monitor a patient's neural state and measure the responsiveness of the neural state to the pharmacological agent (or electrical stimulation) may also be used. By changing (1) the drug or drug class used as the pharmacological agent, (2) the form of the pharmacological agent (e.g., aerosol, pill, suppository, injection, sub-lingual, liquid, skin cream, or the like), and/or (3) the dosage of the pharmacological agent and monitoring the patient's neural state a clinician may be able to better evaluate the effectiveness of an acute dosage of a pharmacological agent relative to the patient's neural state, and determine the appropriate type, form, dosage, and timing of pharmacological agent for managing the patient's neurological disorder. Thus, using the present invention it may be possible to reduce the frequency and/or dosage of agent so that the patient is taking a reduced amount of the agent and is only taking the pharmacological agent when it is actually needed.

This invention creates a new usage and indication for several classes of drugs. Using the systems taught in the present invention, a patient may take a medication in a preventative manner, rather than on a chronic basis or on an acute basis to terminate a seizure after it has begun. This seizure preventative indication is a new use of pharmacological agents in and of itself. Furthermore, some of the dosing regimens use significantly less medication than the dosing used for acute seizure termination indications, such as is used for terminating repetitive seizures or status epilepticus.

Neural state may be altered by the administration of chronic and acute antiepileptic drugs, thereby providing a measure of degree of therapy and response to therapy. The monitored neural state is perturbed by therapy, further validating the neural state, and providing a measure of therapy and more specifically of the neural response to therapy. This can be used to titrate therapy as well as to provide real-time feedback on the response to therapy and real-time estimation of the efficacy of therapy. The uses of the present invention are multiple, including titration of chronic medications, dosing of acute therapy, and monitoring of response to chronic and acute therapy.

Figure 15:
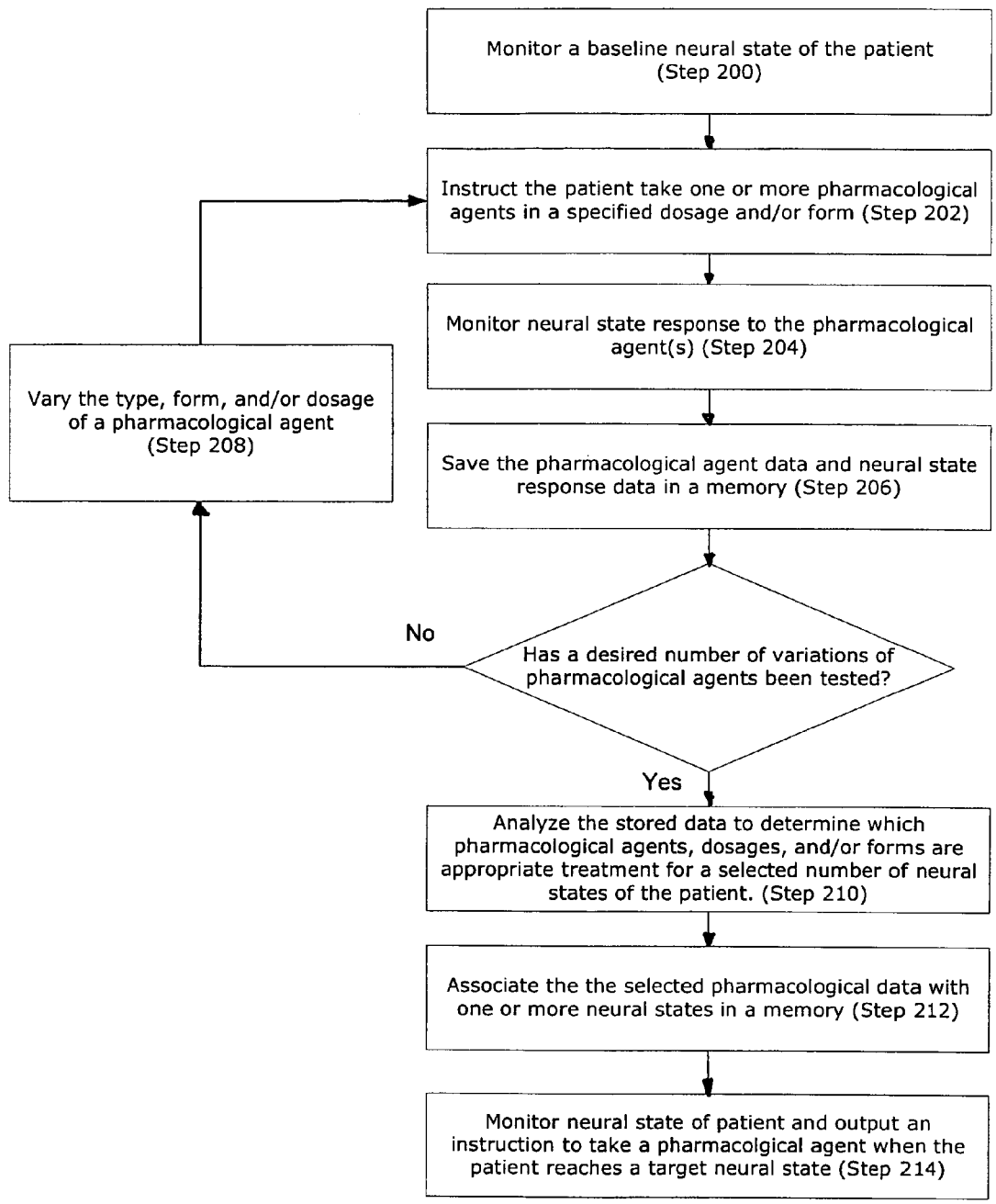
FIG. 15 is a flowchart that illustrates selection of AEDs for use with the systems of the present invention.

FIG. 15 illustrates one simplified method encompassed by the present invention, as applied to the selection and titration of pharmacological agents or other therapies in a patient-specific manner. Such a method allows for the monitoring of a "baseline" neural state, in the absence of a specific therapy or of all therapies, and the response to the addition and/or subtraction of specific therapies.

At step 200, the patient's neural state is monitored for a suitable amount of time to ascertain a patient's "baseline" neural state so as to allow for assessment of the effect that the pharmacological agent has on the patient's neural state. Monitoring of the patient's neural state may be performed in-hospital or out-of-hospital. This in-hospital "baseline" monitoring may be performed in a variety of settings including but not limited to in an epilepsy monitoring unit (EMU), an intensive care unit (ICU), or a regular hospital floor bed. Alternatively, this "Baseline" neural state can be measured in a clinic or in an unconstrained manner using an ambulatory unit, which may be implanted, non-implanted, or a hybrid. The "Baseline" neural state may be calculated using signals obtained from scalp electrodes, implanted electrodes, other electrodes, or a combination thereof. The practical durations for monitoring will vary as a function of the method employed. These ranges include up to several hours or more in a clinic or hospital setting, hours to several weeks in an epilepsy monitoring unit (EMU) or other hospital setting, or hours to months using an ambulatory monitoring system. In any of these or other settings, one may also continue monitoring during the washout or withdrawal of a drug as well as before, during and following the administration of the drug. Neural state monitoring may be performed using any of the embodiments of system 10 described herein or it may be monitored using other invasive or non-invasive conventional or proprietary systems.

At step 202, the patient is instructed to take one or more pharmacological agents in a first specified dosage. Instructions to take the pharmacological agent may be carried out by having the patient follow a clinician defined regimen (e.g., at 12 noon take "X" amount of pharmacological agent "A", and at 8 pm take "Y" amount of pharmacological agent "B") which may be stored in a memory of system 10 and communicated to the patient through the patient communication assembly 18. This regimen may be predefined or it may be dynamically adjusted or a combination of these. For example, certain therapies have a more pronounced effect during specific neural states or ranges thereof; so the timing of therapies may be adjusted to be given during certain neural states and the dosing may be a function of the current, historical, or predicted future neural states. Of course, the clinician defined regimen may be communicated to the patient in a variety of other methods, and the present invention is not limited to using system 10 to provide instructions to the patient.

At step 204, the patient's neural state is monitored to ascertain the perturbation (if any) of the patient's neural state caused by the first specified dosage of the pharmacological agent. The effect of the pharmacological agent on the neural state may be ascertained using system identification methods known in the art of control theory and dynamic system modeling. Depending on the route of administration and the time course of the drug plasma level changes, the perturbation could be modeled as a step, impulse, first order, second order, or higher order process; and the neural state response can be deconvolved with or otherwise analyzed as a response to the drug administration. In this model, the administration of the pharmacological agent is the input function or driving function being input into the system, which is the patient; and the neural state can be viewed as the state or the output function. The transformation from input function to output function represents the neural state response to the administered pharmacological agent.

Perturbation caused by the pharmacological agent may take a variety of forms. For example, depending on what the neural state measures, the pharmacological agent may increase some or all elements of the patient's neural state, decrease some or all elements of the patient's neural state, stabilize some or all elements of the patient's neural state, act to reduce or stop a trending of some or all elements of the patient's neural state, act to maintain a trending of some or all elements of the patient's neural state, or the like. One response to antiepileptic pharmacological agents causes a transient increase in neural state, as the various patterns of neural activity become desynchronized in response to the medication. At least one of the elements of the neural state increases transiently with a time course similar to that of the drug plasma levels. Some responses are predominantly transient and return toward baseline as the drug redistributes, is metabolized, or is excreted. Other responses are more stable and exhibit a change that persists for a longer time period, beyond the increase in plasma level of the drug. A combination of such neural states, which can be viewed as a vector, can provide a richer level of information characterizing the neural state and its response to therapy than a single scalar neural state element does.

Parameters of the neural state responses include the time course of response, time constant of response, magnitude of increase in neural state, magnitude of decrease in neural state, degree of stabilization of neural state, latency of onset of response in neural state, slope or first time derivative of change in neural state, other time derivatives of the response in neural state, area under the curve of the neural state response, or other features or combinations thereof. The dosage, type, and time of administration of the pharmacological agent and neural state response may thereafter be stored in a memory for future analysis by the clinician (step 206).

If a desired number of variations of pharmacological agents have been tested, then the method moves to step 210 (described below). However, if additional pharmacological agents need to be tested, at some desired time after taking the first specified dosage of the pharmacological agent, the patient may be (1) instructed to take the same pharmacological agent in which some parameter (dosage, form, etc.) of the agent is varied or (2) instructed to take a different type of pharmacological agent (step 208, step 202). The different types may include variations in drug class, drug (or agent), drug form (such as intravenous, intramuscular, intranasal, sublingual, buccal, transdermal, intrathecal, intraventricular, intraparenchymal, cortical, oral, rectal, or other formulation or route), or dosages. For example, if there are different forms of the pharmacological agent, such as an aerosol, pill, suppository, injection, sub-lingual, liquid skin cream, transdermal patch, or the like, the form of the agent may be varied to determine if there are different neural state responses to the different forms of the agent.

For each of the additional pharmacological agents administered, the patient's neural state is again monitored to ascertain the perturbation (if any) of the patient's neural state caused by the second dosage and the data is stored in memory (Steps 204, 206). The steps are repeated until a desired number of different pharmacological agents have been tested.

While not illustrated in FIG. 15, it may be desirable to determine if the perturbation effect of the pharmacological agent is substantially the same for the patient's different neural states. For example, a pharmacological agent may be more effective when the patient is in one neural state range, but less effective when the patient is in another neural state range. The effectiveness of a pharmacological agent may vary as a function of neural state, becoming progressively more effective as a neural state varies along a range. Thus, it may be useful to instruct the patient to take the same dosage of the same pharmacological agent when the patient is in various a neural state ranges to ascertain the variation, if any, in efficacy of the pharmacological agent. This would allow the clinician to determine if there is a different neural response to the same dosage of the same pharmacological agent for the different neural states, and thus allow the clinician to customize the prescribed pharmacological regimen accordingly.

Figure 16:
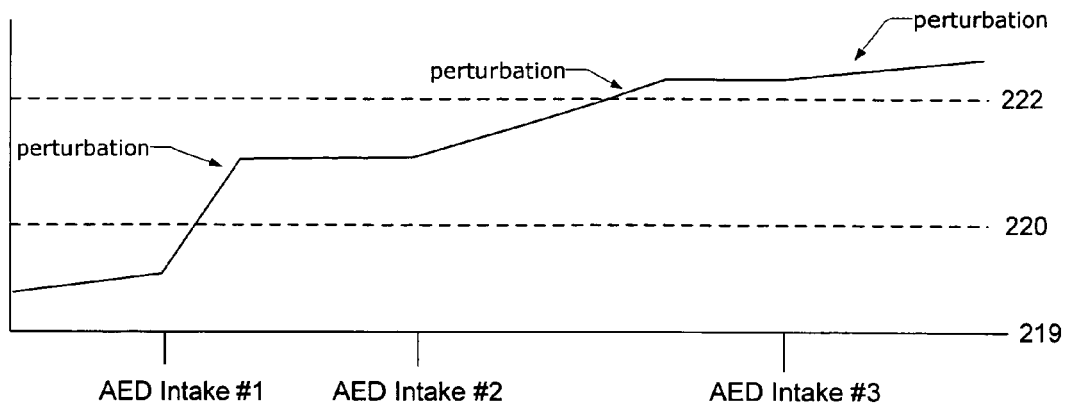
FIG. 16 is an example of how an AED may have a different perturbation effect on the neural state above and below different threshold levels.

For example, as shown in FIG. 16, if the patient's neural state is in a range between 219 and 220 and the patient takes a dosage of a specific AED, the patient's neural state may be perturbed a large amount (or a small amount, depending on the patient and the AED taken). However, if the patient's neural state is within a "normal range" (between lower threshold 220 and upper threshold 222) and the patient takes the same dosage of the same pharmacological agent (AED Intake #2), the neural state may be perturbed upward a different amount and may take longer for the perturbation to occur (which in this example, is a lesser amount in a longer period of time). Finally, if the patient's neural state is above upper threshold 222, the same dosage of the pharmacological agent may actually have an even lower perturbation effect (or no perturbation effect) on the neural state. Consequently, it may be desirable to test the effect of the pharmacological agent have on the neural state when the patient is in different neural states to better assess the effect that the pharmacological agent has on various neural state.

Once the desired number of types, forms and dosages of pharmacological agents are tested, the clinician may then analyze the stored data to determine which type, form, and/or dosage of pharmacological agents are effective at managing the different neural states of the patient (Step 210). For example, some pharmacological agents may act faster, cause a larger perturbation in the neural state, or the like. The clinician may use the stored data, alone or in combination with other extrinsic data, to generate a treatment regimen for the patient and program system 10 to provide specific recommendations for a desired number of patient states. Typically, however, one or more pharmacological agent data (e.g., type, form, dosage, and timing) are programmed into a memory of system 10 and associated with selected neural states (step 212).

Of course, the treatment regimen will typically include other non-pharmacological treatments for managing the patient's neural state and propensity for the future seizure, e.g., electrical stimulation, behavioral modification including making themselves safe, etc., as described above. The treatment regimen may be graded as a function of neural state, with increasing efficacy, magnitude, or with increasingly tolerated side effects, as the propensity of a seizure increases or as the seizure prediction horizon decreases. This may involve initial therapy with vagus nerve stimulation, potentially followed by other stimulation, and followed with pharmacological intervention, again along a varying scale. Pharmacotherapy may start with a small dose of a minimally sedating and well tolerated agent and as the time until the predicted seizure horizon decreases and/or the propensity for seizure increases, then a series of medication may be administered with progressively increasing degrees of invasiveness (i.e. oral, sublingual, intranasal, intramuscular, then intravenous) and/or side effects (increasingly sedating).

Referring again to FIG. 15, once system 10 has been properly programmed to specify an appropriate action for specific neural states, system 10 may be used on a day-to-day basis to monitor the patient's neural state. As described above, when the patient's neural state reaches one of the specified neural state thresholds or ranges associated with the clinician defined pharmacological regimen, a communication will be output to the patient that is indicative of an appropriate action for the patient (step 214). Preferably, the appropriate action is in the form of an instruction that indicates the pharmacological treatment that was previously determined by the clinician. Typically, the output is in the form of an instruction or recommendation which specifies at least one of a type, form, formulation, dosage, and route of administration of a pharmacological agent. However, it may be helpful to merely indicate to the patient that their risk of a seizure has increased. In the other end of the spectrum, when the seizure is imminent and prevention of the seizure using a pharmacological agent or other treatment means is unlikely, the communication to the patient may indicate to the patient to put themselves in a safe place. Any combination of instructions, warning, and information is possible.

The patient's reaction to the pharmacological agents may change over time. Consequently, during regular checkups or through periodic uploading of the patient's neural state information, drug compliance data, seizure prediction data uploads to the clinician, the clinician may be able to monitor the perturbation effect of the pharmacological agents on the patient's neural state. If the clinician (or the system 10 itself) determines that the programmed pharmacological agent is not achieving the desired result, the clinician will have the ability to prescribe a different pharmacological agent, dosing regimen, or dosage and reprogram the device assembly 12.

While FIGS. 15 and 16 illustrate a method for improving a pharmacological regimen for treating epilepsy, such methods may also be used to improve treatments for other neurological disorders and non-neurological disorders. For example, it may be possible to monitor the neural state response to medications used in the treatment of other neurological disorders and improve the medication/pharmacological agent regimen by monitoring the responsiveness to different dosages of the pharmacological agent.

The present invention may also be used for patient screening and responder selection. By assessing in which patient's the neural state is found to respond to and by which amount to any of various therapies, one can assess the relative efficacy of the use of therapies for that particular patient. Assessing the response of a patient to vagus nerve stimulation, intracranial stimulation, tactile stimulation, pharmacological intervention, or any other therapy, in a preoperative manner, one can assess the potential efficacy of the present invention prior to the implantation of an implanted implementation. This has enormous value in reducing the number of non-responder patients in whom a device may be implanted, improving efficacy and reducing morbidity in patient who may not benefit from the technology. The degree of responsiveness or efficacy may be assessed by the magnitude, latency, time course, and other parameters that may be extracted or calculated from the response in neural state to the administration of therapy to the patient.

The present invention further provides system and methods that may be used to modify or alter the scheduling and dosing of a chronically prescribed pharmacological agent, such as an AED. While, the present invention is preferably used with acute or non-chronic drug regimens for managing epilepsy, the systems of the present invention may also be used with chronic drug regimens. However, with the present invention, it may be possible to reduce the dosage or frequency of the chronically taken medications. The predictive algorithms described above may be still be used to characterize the patient's propensity for the future seizure, typically by monitoring the patient's neural state. If the predictive algorithm determines that the patient has an increased risk of, propensity for, or probability of an epileptic seizure or otherwise predicts the onset of a seizure, the system may provide an output that indicates or otherwise recommends or instructs the patient to take an accelerated or increased dosage of the chronically prescribed pharmacological agent. Consequently, the present invention is able to modulate and titrate the intake of the prescribed agent in order to decrease side effects and maximize benefit of the AED. In such embodiments, it may be possible to maintain a lower plasma level of the AED in the patient, and increase the plasma level of the AED only when needed. This allows for maximization of efficacy concurrent with minimization of total medication dose.

In another aspect, the present invention provides systems and methods for improving a patient's compliance with a prescribed pharmacological regimen and for providing safeguards for controlling the patient's pharmacological agent (e.g., medication) intake. Patient communication assembly 18 may be programmed to periodically transmit a communication to the patient when a medication is scheduled to be taken by the patient. The communication might be carried out via an audio signal (e.g., beep(s), voice, etc.), vibratory signal, visual signal (e.g., text or graphics provided on a display on patient communication assembly 18, flashing lights), other signals, or a combination thereof. In some embodiments, it may be desirable to require the patient to activate an input device 94 on patient communication assembly 18 every time the patient takes the medication. Activation of the input signal may carry out a variety of functions. First, it may be used to turn off the "reminder" communication provided by the patient communication assembly 18. Second, it may provide an indication to system 10 that the medication has been taken. The input from the patient may be saved in a memory and the saved data may be used by the clinician to assess whether or not the patient is properly taking their prescribed pharmacological agents.

System 10 may also be used to monitor the patient's compliance with the prescribed pharmacological agent regimen. For example, if patient communication assembly 18 communicates a signal to the patient to take a pharmacological agent and the patient activates the input, but does not actually take the prescribed pharmacological agent, the system may have a compliance component that tracks the patient's input and monitors the patient's propensity for the future seizure (e.g., neural state) to determine the patient's response to the pharmacological agent. If no perturbation of the patient's propensity for a seizure is measured or if the expected perturbation is not measured within a predetermined time period, the patient communication assembly may generate a second reminder signal to the patient reminding the patient to take the scheduled pharmacological agent. This can monitor for both non-compliance and for inadequate response to therapy.

The systems of the present invention may also have safeguards that monitor the patient's intake of a pharmacological agent. For example, in one embodiment a maximum threshold of medication over a period of time may be set by the clinician, and the maximum threshold may be saved in a memory of system 10. As the patient's propensity for the future seizure (e.g., neural state) is monitored, the dosage and time data for the communications to the patient which indicate taking the pharmacological agent (e.g., medication), may be saved into memory. If the maximum threshold of medication is reached for the predetermined period of time (e.g., day, week, month, year, or other predetermined time period), system 10 will be prevented from communicating an instruction to the patient to take additional dosages of the prescribed pharmacological information. Instead of providing the instruction, system 10 may be configured to provide a warning to the patient to indicate that the maximum amount of medication is being reached. Such a warning would allow the patient to contact their clinician or the like. In such cases, it may be desirable to have the clinician program a second, alternative pharmacological agent or other appropriate action into memory that would then be output to the patient.

It may be possible to configure system 10 so that when the amount of medication taken approaches the maximum, a signal may be sent to a server that the clinician may access or directly to a clinician communication assembly 20 that is in communication with system 10 that warns the clinician of the patient's status. In some embodiments, system 10 may be configured to regularly communicate pharmacological agent updates and/or neural state updates (e.g., number of seizures) to the clinician. This has considerable value in assessing and preventing the occurrence of an overdose of antiepileptic and other drugs, including benzodiazepines or barbiturates.

The present invention may also be used as a seizure monitoring system. Since the system monitors the neural state of the patient and may predict the onset of a seizure, the system may also be able to determine if a seizure is occurring or has occurred in a patient, the number of seizures, the time of the seizure, length of the seizure, etc. Such data may be stored in memory for later assessment by the clinician or for helping the system 10 adapt to the patient. If a seizure is detected, system 10 may be configured to automatically deliver a predetermined or adaptive electrical stimulation and/or drug infusion in an attempt to abort the seizure or otherwise reduce the magnitude and/or duration of the seizure. Additionally, it may be desirable to provide an output to the patient that informs the patient that a seizure has occurred. A seizure log may be stored in memory for reference to the clinician and patient. The systems 10 of the present invention may be used as an out-of hospital monitoring system, and would allow the patient to go about their day-to-day activities, without being confined to an epilepsy monitoring unit (EMU) in the hospital. The present invention may augment or replace much of the monitoring performed in an epilepsy monitoring unit (EMU), enabling clinicians to collect long duration blocks of extracranial or intracranial data from a patient in an ambulatory setting, depending on the placement of the recording electrodes. This allows the clinician to assess the patient's symptoms and neural state in real-life conditions, including variations in plasma levels of medications and various environmental influences.

Figure 17:
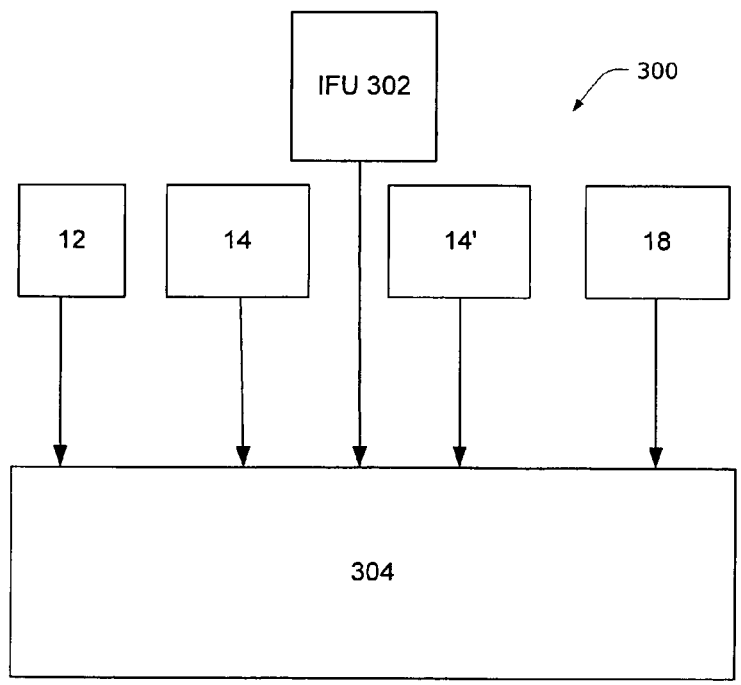
FIG. 17 illustrates a kit that is encompassed by the present invention.

Referring now to FIG. 17, the present invention will further comprise kits 300 including any combination of the components described above, instructions for use (IFU) 302, and packages 304. Typically, the kit 300 will include some combination of the device assembly 12, one or more patient interface assemblies 14, 14' and patient communication assembly 18. The IFU 302 will set forth any of the methods described above. Package 304 may be any conventional medical device packaging, including pouches, trays, boxes, tubes, or the like. The instructions for use 302 will usually be printed on a separate piece of paper, but may also be printed in whole or in part on a portion of the packaging 304.

Drugs Used in the Treatment of Epilepsy

Some of the AEDs that may be used with the present invention will now be described. The anti-epileptic drugs used of epilepsy fall into three major categories. One class of epileptic drugs limits the sustained, repetitive firing of a neuron by promoting the inactivated state of voltage-activated $Na^+$ channels. Another mechanism is by the enhancement of gamma-aminobutyric acid (GABA)-mediated synaptic inhibition, either pre- or post-synaptically. Yet another class of compounds limit activation of a particular voltage-activated $Ca^{2+}$ channel known as the T current.

Antiepileptic drugs function by at least one of several mechanisms to control neural firing activity. The major classes based on the mechanism of action are as follows:
 1) Modulation of voltage dependent ion channels
   a) Sodium channel blockade
   b) Calcium channel blockade
   c) Potassium channel facilitation
 2) Enhancement of Synaptic Inhibition
   a) GABA Agonists
     i) Benzodiazepines
     ii) Barbiturates
     iii) Felbamate
     iv) Topiramate
   b) Glycine
   c) Regionally Specific Transmitter Systems
     i) Monoamines
       (1) Catecholamines
       (2) Serotonin
       (3) Histamine
     ii) Neuropeptides
       (1) Opioid Peptides
       (2) Neuropeptide Y
     iii) Inhibitory Neuromodulator
       (1) Adenosine
 3) Inhibition of synaptic transmission
   a) NMDA Antagonists
   b) AMPA Antagonists
   c) Metabotropic Type
   d) Kainate Type Some specific examples of anti-epileptic drugs that may be used with the present invention are described below:

Hydantoins:

Phenyloin (diphenylhydantoin, Dilantin, Diphenylan) is used typically for all types of partial and tonic-clonic seizures. Other suitable hydnatoins include mephenyloin, ethotoin.

Phenyloin has the following structure:

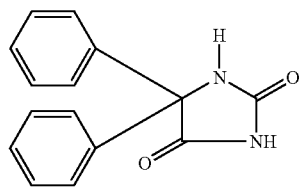 [SMILES: O=C1NC(=O)C(c2ccccc2)(c2ccccc2)N1]

A 5-phenyl or other aromatic substituent appears important for activity. Chronic control of seizures is generally obtained with concentrations above 10 µg/ml, while toxic effects such as nystagmus develop at concentrations around 20 µg/ml.

Anti-Seizure Barbiturates:

Phenobarbital, N-methylphenobarbital, and metharbital are typically used in therapies for epilepsy. Other barbiturates may also be used in the present invention. N-methylphenobarbital (Mephobarbital; Mebaral) and phenobarbital are effective agents for generalized tonic-clonic and partial seizures.

During long term therapy in adults, the plasma concentration of phenobarbital averages about 10 µg/ml per daily dose of 1 mg/kg; in children the value is between about 5 to about 7 µg/ml per 1 mg/kg. Plasma concentrations of about 10 to about 35 µg/ml are recommended for control of seizures; about 15 µg/ml is generally the minimum for prophylaxis against febrile convulsions.

Deoxybarbiturates:

Primidone (mysoline) is used against partial and tonic-clonic seizures. During long term therapy, plasma concentrations of primidone and phenobarbital average between about 1 µg/ml and about 2 µg/ml, respectively, per daily dose of 1 mg/kg of primidone.

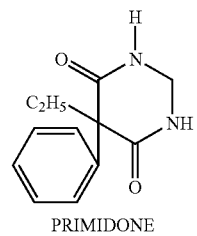 [SMILES: CCC1(c2ccccc2)C(=O)NCNC1=O]

PRIMIDONE

Iminostilbenes:

Carbamazepine is used in the treatment of partial and tonic-clonic seizures. Carbamazepine is a derivative of iminostilbene with a carbamyl group at the 5 position. Therapeutic concentrations are between about 6 to about 12 µg/ml. Oxcarbazepine (Trileptal) is a keto analog of carbamazepine which acts as a prodrug in humans. Oxcarbazepine is typically used as a monotherapy or adjunct therapy for partial seizures in adults and as adjunctive therapy for partial seizures in children. Oxcarbazepine is thought to block voltage-sensitive sodium channels. In addition, increases potassium conductance and modulation of high-voltage activated calcium channels, which may also have a role in controlling seizures. Dosage is between about 0.6 to about 2.4 g/day.

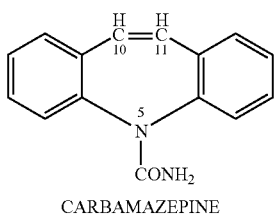 [SMILES: NC(=O)N1c2ccccc2C=Cc2ccccc21]

CARBAMAZEPINE

Succinimides:

Ethosuximide (Zarontin) is typically used for the treatment of absence seizures. Methsuximide (Celontin) and phensuximide (Milontin) have phenyl substituents and are more active against maximal electroshock seizures. During long-term therapy, the plasma concentration of ethosuximide averages between about 2 µg/ml per daily dose of 1 mg/kg. A plasma concentration of between about 40 to about 400 µg/ml is required for satisfactory control of absence seizures in most patients. An initial daily dose of 250 mg in children and 500 mg in older children and adults is increased by 250 mg increments at weekly intervals until seizures are adequately controlled or toxicity intervenes. Divided dosage is required occasionally to prevent nausea or drowsiness associated with single daily dosage. The usual maintenance dose is about 20 mg/kg per day.

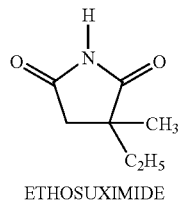

ETHOSUXIMIDE

Valproic Acid:

Valproic acid (n-dipropylacetic acid) is a simple branched-chain carboxylic acid. The concentration of valproate in plasma that is associated with therapeutic effects is between about 30 to about 100 µg/ml. Valproate is effective in the treatment of absence, myoclonic, partial, and tonic-clonic seizures. The initial daily dose is usually about 15 mg/kg, and this is increased at weekly intervals by between about 5 to about 10 mg/kg per day to a maximum daily dose of 6 mg/kg. Divided doses are given when the daily dose exceeds 250 mg.

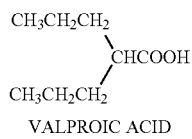

VALPROIC ACID

Benzodiazepines:

A large number of benzodiazepines have broad anti-seizure properties. In the United States, clonazepam (Klonopin) and clorazepate (Traxene-SD, others) have been approved for chronic, long term treatment of seizures. Diazepam (Valium, Diastat, others) and lorazepam (Ativa) are commonly used in the management of status epilepticus.

Clonazepam is useful in the therapy of absence seizures as well as myoclonic seizures in children. The initial dose of clonazepam for adults does not typically exceed 1.5 mg per day, and for children is between about 0.01 to about 0.03 mg/kg per day. The dose-dependent side effects are reduced if two or three divided doses are given each day. The dose may be increased every 3 days in amounts of between about 0.25 to about 0.5 mg per day in children and between about 0.5 to about 1 mg per day in adults. The maximal recommended does is 20 mg per day for adults and 0.2 mg/kg per day for children.

While diazepam is an effective agent for treatment of status epilepticus, its short duration of action is a disadvantage, leading to the use of intravenous phenyloin in combination with diazepam. Diazepam is administered intravenously and at a rate of no more than about 5 mg per minute. The usual dose for adults is between about 5 to about 10 mg as required; this may be repeated at intervals of 10 to 15 minutes, up to a maximal dose of about 30 mg. If necessary, this regime can be repeated in 2 to 4 hours, but no than 100 mg should be administered in a 24-hour period.

Clorazepate is effective in combination with certain other drugs in the treatment of partial seizures. The maximum initial dose of clorazepate is 22.5 mg per day in three portions for adults and 15 mg per day in two doses in children.

Gabapentin:

Gabapentin (Neurontin) is typically used in the treatment of partial seizures, with and without secondary generalization, in adults when used in addition to other anti-seizure drugs. Gabapentin is usually effective in doses of between about 900 to about 1800 mg daily in three doses. Therapy is usually begun with a low dose (300 mg once on the first day), and the dose is increased in daily increments of 300 mg until an effective dose is reached. Gabapentin is structurally related to the neurotransmitter, GABA.

GABAPENTIN

Lamotrigine:

Lamotrigine (Lamictal) is a phenyltriazine derivative. It is used for monotherapy and add-on therapy of partial and secondarily generalized tonic-clonic seizures in adults and Lennox-Gastaut syndrome in both children and adults. Patients who are already taking a hepatic enzyme-inducing anti-seizure drug are typically given lamotrigine initially at about 50 mg per day for 2 weeks. The dose is increased to about 50 mg twice per day for 2 weeks and then increased in increments of about 100 mg/day each week up to a maintenance dose of between about 300 to about 500 mg/day in two divided doses. For patients taking valproate in addition to an enzyme-inducing anti-seizure drug, the initial dose is typically about 25 mg every other day for 2 weeks, followed by an increase to 25 mg/day for two weeks; the dose then can be increased to 50 mg/day every 1 to 2 weeks up to a maintenance dose of about 100 to about 150 mg/day divided into two doses. Lamotrigine is a use-dependent blocker of voltage-gated sodium channels and inhibitor of glutamate release.

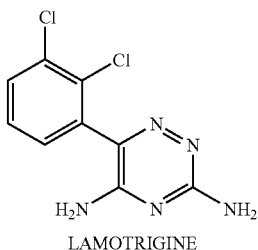 [SMILES: Nc1nnc(-c2cccc(Cl)c2Cl)c(N)n1]
LAMOTRIGINE

Levetiracetam:

Levetiracetam (Keppra) is a pyrrolidine, the racemically pure S-enantiomer of α-ethyl-2-oxo-1-pyrrolidineacetamide, and is typically used for treating partial seizures. Dosage is about 3 gm/day.

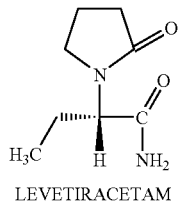
LEVETIRACETAM

Tiagabine:

Tiagabine inhibits the uptake of the neurotranzmitter GABA, which results in an increase in GABA-mediated inhibition with in the brain. The dosage with enzyme-inducing drugs is between about 30 to about 45 mg/day and without enzyme-inducing drugs is between about 15 to about 30 mg/day.

Topiramate:

Topiramate is a sulphamate-substituted monosaccharide. Its mode of action probably involves the following: blockade of voltage-sensitive sodium channels; enhancement of GABA activity; antagonism of certain subtypes of glutamate receptors; and inhibition of some isozymes of carbonic anhydrase. The dosage is between about 200 to about 400 mg/day, with a maximum of about 800 mg/day.

Zonisamide:

ZONEGRAN™ (zonisamide) is an anti-seizure drug chemically classified as a sulfonamide. The active ingredient is zonisamide, 1,2-benzisoxazole-3-methanesulfonamide. ZONEGRAN is supplied for oral administration as capsules containing 100 mg zonisamide.

Zonisamide may produce these effects through action at sodium and calcium channels. In vitro pharmacological studies suggest that zonisamide blocks sodium channels and reduces voltage-dependent, transient inward currents (T-type $Ca^{2+}$ currents), consequently stabilizing neuronal membranes and suppressing neuronal hypersynchronization. In vitro binding studies have demonstrated that zonisamide binds to the GABA/benzodiazepine receptor ionophore complex in an allosteric fashion which does not produce changes in chloride flux. Other in vitro studies have demonstrated that zonisamide (10-30 μg/mL) suppresses synaptically-driven electrical activity without affecting postsynaptic GABA or glutamate responses (cultured mouse spinal cord neurons) or neuronal or glial uptake of [3H]-GABA (rat hippocampal slices). Thus, zonisamide does not appear to potentiate the synaptic activity of GABA. In vivo microdialysis studies demonstrated that zonisamide facilitates both dopaminergic and serotonergic neurotransniission. Zonisamide also has weak carbonic anhydrase inhibiting activity, but this pharmacologic effect is not thought to be a major contributing factor in the antiseizure activity of zonisamide.

ZONEGRAN (zonisamide) is recommended as adjunctive therapy for the treatment of partial seizures in adults. ZONEGRAN is administered once or twice daily, except for the daily dose of 100 mg at the initiation of therapy. ZONEGRAN is given orally and can be taken with or without food. The initial dose is 100 mg daily. After two weeks, the dose may be increased to 200 mg/day for at least two weeks. It can be increased to 300 mg/day and 400 mg/day, with the dose stable for at least two weeks to achieve steady state at each level. Evidence from controlled trials suggests that ZONEGRAN doses of 100-600 mg/day are effective.

Vigabatrin:

Vigabatrin is an irreversible inhibitor of gamma-aminobutyric acid transaminase (GABA-T), the enzyme responsible for the catabolism of the inhibitory neurotransmitter gamma-aminobutyric acid (GABA) in the brain. The mechanism of action of vigabatrin is attributed to irreversible enzyme inhibition of GABA-T, and consequent increased levels of the inhibitory neurotransmitter, GABA. The dosage is between about 2 to about 3 g/day, with a maximum of about 3 g/day.

The recommended starting dose is 1 g/day, although patients with severe seizure manifestations may require a starting dose of up to 2 g/day. The daily dose may be increased or decreased in increments of 0.5 g depending on clinical response and tolerability. The optimal dose range is between about 2 to about 4 g/day. Increasing the dose beyond 4 g/day does not usually result in improved efficacy and may increase the occurrence of adverse reactions. The recommended starting dose in children is 40 mg/kg/day, increasing to about 80 to about 100 mg/kg/day, depending on response. Therapy may be started at about 0.5 g/day, and raised by increments of about 0.5 g/day weekly, depending on clinical response and tolerability.

Methods of Use of the Anti-Epileptic Drugs

Current antiepileptic drugs (AEDs) are used to treat one of two indications: (1) to reduce the frequency of seizures, and (2) to terminate seizures once they have begun. For the first indication, antiepileptic drugs designed to have a long half life are dosed to maintain a desired level of a blood plasma concentration of the drug. By maintaining stable blood plasma concentrations of the AEDs, the seizure threshold is increased and the frequency of seizures that occur is usually reduced. This is an "open-loop" approach to therapy, in which therapy is stable and is not adjusted in response to any changes in the patient's propensity for a seizure. An example is the use of phenyloin (Dilantin), which is given preferably once every 8 hours, but whose half life is long enough to permit once daily dosing in less compliant or capable patents.

For the second indication, AEDs are used to terminate a seizure after it has begun and has become clinically evident. In these indications, the seizure has already generalized, and the patient is typically incapacitated. Another person, either a family member or medical caregiver, administers a medication to terminate the seizure. Examples include (A) rectal diazepam (diastat) which may be given by family members or medical personnel and (B) intravenous lorazepam, which is typically given once a patient has been admitted to the hospital for treatment.

The methods taught in the present invention provide novel approaches to the treatment of epilepsy. In one aspect of the invention, rather than provide chronic, continuous levels of medication which are unchanged despite changes in the patient's propensity for the seizure or wait until a seizure has incapacitated the patient, the present invention teaches the acute, preventative delivery of a pharmacological agent, preferably an anti-epileptic drug, that can modulate the patient's propensity for the seizure and prevent the further progression into a state that facilitates or predisposes to a seizure state. In one embodiment of the invention, the dosing and administration of an anti-epileptic drug is co-related to or a function of the patient's propensity for the future seizure, this characterization typically being related to the measured neural state, or the like. In another embodiment of the invention, the dosing and administration of an anti-epileptic drug is co-related to or a function of a probability and/or a predicted time horizon that a patient has before the epileptic seizure is predicted to occur. Typically, the longer the predicted amount of time and lower probability, the lower the dose of the epileptic drug, and vice-versa. Also, the route of administration may also vary based on the timing of the prediction and probability.

In a preferred embodiment, a lower dose of an anti-epileptic drug is administered to a patient. This dose may be about 5% to about 95% lower than the recommended dose for the drug, and preferably at or below 90% of the recommended dose, and most preferably below about 50% of the recommended dose. This lower dose is preferably administered acutely to perturb the patient's neural state and reduce the patient's propensity for seizures. Tables 1 and 2 provide some examples of dosages of some anti-epileptic drugs and formulation types that can be administered to a patient based on a prediction horizon. The prediction horizon is the amount of time after which the patient could have an epileptic seizure and is directly correlated to the propensity or probability of having a seizure. For example, a one minute prediction horizon means that the prediction algorithm has predicated that the patient is at relatively high propensity for a seizure and will likely have an epileptic seizure in about 1 minute. The column on the left side of the "Drug Dosing" portion of the chart illustrates the conventional "recommended dosage," and the columns to the right of the "recommended dosage" illustrate some examples of the potential reduced dosage, based on the prediction horizon. While not shown in Tables 1 and 2, similar tables could be provided that are based on the patient's neural state or propensity for seizure. Thus, instead of having the prediction horizon as headings, the corresponding neural state or propensity for seizure may be used.

TABLE 1

| Anti-Epileptic Drug | After | Drug Dosing (mg/kg) - Levels needed if given: | | | | | | |
|---|---|---|---|---|---|---|---|---|
| | | Prediction Horizon (min) | | | | | | |
| (Pediatric Dosing) | Seizure Onset | 1 | 5 | 10 | 15 | 20 | 25 | 30 |
| Buccal Midazolam | 0.5 | 0.25 | 0.125 | 0.0625 | 0.03125 | 0.015625 | 0.007813 | 0.003906 |
| Intranasal Midazolam | 0.2 | 0.1 | 0.05 | 0.025 | 0.0125 | 0.00625 | 0.003125 | 0.001563 |
| IM Midazolam | 0.2 | 0.1 | 0.05 | 0.025 | 0.0125 | 0.00625 | 0.003125 | 0.001563 |
| Rectal Diazepam | 0.5 | 0.25 | 0.125 | 0.0625 | 0.03125 | 0.015625 | 0.007813 | 0.003906 |
| IV Lorazepam | 0.1 | 0.05 | 0.025 | 0.0125 | 0.00625 | 0.003125 | 0.001563 | 0.000781 |
| IV Diazepam | 0.3 | 0.15 | 0.075 | 0.0375 | 0.01875 | 0.009375 | 0.004688 | 0.002344 |

TABLE 2

| Anti-Epileptic Drug | After | Drug Dosing (mg) - Levels needed if given: | | | | | | |
|---|---|---|---|---|---|---|---|---|
| | | Prediction Horizon (min) | | | | | | |
| (Adult Dosing) | Seizure Onset | 1 | 5 | 10 | 15 | 20 | 25 | 30 |
| Rectal Diazepam | 10 | 5 | 2.5 | 1.25 | 0.625 | 0.3125 | 0.15625 | 0.078125 |
| Lorazepam | 4 | 2 | 1 | 0.5 | 0.25 | 0.125 | 0.0625 | 0.03125 |
| Diazepam | 10 | 5 | 2.5 | 1.25 | 0.625 | 0.3125 | 0.15625 | 0.078125 |

The dose administered to the patient is useful to prevent the occurrence of the future seizures. Preferably, the dose is related to the type of AED being administered, the type of formulation, and/or the pharmacokinetics of the drug and formulation. FIGS. 21 and 22 give examples of drug dosing schedules which compare the drug dosing to the prediction horizon. FIG. 21 provides an example of the doses of buccal midazolam related to the prediction horizon. FIG. 22 provides an example of the various doses for different forms of benzodiazepines. Some other suitable drugs, doses, and formulations suitable for the present invention are provided in Table 3.

TABLE 3

| Drug | Formulation | Prediction Horizon | Time to Clinical Onset | Approximate Dose Compared to (dose used in seizure Termination) |
|---|---|---|---|---|
| Midazolam | Buccal | 5 to 30 minutes | 5 to 8 minutes | 20–30% (0.5 mg/kg) |
| Midazolam | Intranasal | 1 to 20 minutes | 30 sec to 2 minutes | 10–25% (0.2 mg/kg) |
| Diazepam | Rectal | 10 to 30 minutes | 5 to 15 minutes | 10–25% (0.3 mg/kg) |

TABLE 3-continued

| Drug | Formulation | Prediction Horizon | Time to Clinical Onset | Approximate Dose Compared to (dose used in seizure Termination) |
| --- | --- | --- | --- | --- |
| Midazolam | Intramuscular | 1 to 30 minutes | 1 to 5 minutes | 5–20% (0.2 mg/kg) |
| Midazolam | Intravenous | 1 to 10 minutes | 1 to 5 minutes | 5–20% (0.2 mg/kg) |

Another aspect of the invention is a method for preventing or otherwise managing epileptic seizures. One embodiment involves administration of an effective amount of an anti-epileptic drug to a patient. The acute administration may be provided locally to a nervous system component or delivered systemically to the patient. The acute administration is provided at a time prior to a possible occurrence of a seizure. Typically, this time is about greater than 30 seconds, and preferably between about 1 minute to about 30 minutes. The dose of AED administered is typically between 5% and 95% lower than a dose of said drug that is effective after a seizure has occurred, and preferably less than about 50% of the drug that is effective after the seizure has occurred. In some cases, it may be possible to reduce the dosage of the drug to be between about 50% and about 5% of the drug that is effective after the seizure has occurred, but depending on the propensity, it may be possible to reduce the dosage even greater. The amount of AED administered may also be a function of the time before a seizure may occur. That is, the longer the time before a seizure may occur, the smaller the dose of the AED administered. This administration is typically an acute administration and could comprise about 2 to about 10 doses being administered, preferably all the doses being administered before the occurrence of a seizure.

The dose of drug administered may be greater than or equal to about 100% of the dose normally administered to patients. However, the preferred dose of the AEDs administered herein is a fraction of the normal dose. This normal dose is typically the dose that is considered to be an effective dose in the art (or by the FDA) to reduce and/or eliminate the occurrence of a seizure after a seizure has occurred. The dose used in the invention herein could also be a fraction of the dose that has been used and has been found effective in a particular patient or a sub-population of patients. That is, in some patients it is possible that the dose used is higher or lower than the recommended dose, and in these patients the dose administered is a fraction of the dose that is effective in reducing and/or eliminating the occurrence of a seizure in them after a seizure has occurred. The normal dose can be found for different patient populations and/or different kinds of seizures in text books, the Physician's Desk Reference, or approved by a regulatory agency, such as the Food and Drug Administration (FDA). Optionally, the system can be utilized with a particular patient or sub-population of patients to identify the optimum drug, the appropriate dosage for that patient, and/or the dosage that correlates to the prediction horizon or expected onset of the seizure by evaluating the data from the system and modifying the treatment accordingly.

Screening for Drugs and Patient Responder Population:

Another aspect of the invention provides methods for screening novel and/or existing anti-epileptic agents for their anti-epileptic properties for particular patients. The present invention also provides methods for screening for patient responder subpopulations.

These methods preferably involve characterizing the patient's neural state by classifying extracted features from one or more signals from the patient, patient history, and patient feedback. For example, the neural state may be monitored before and after administration of a drug, and the effects of the drug the neural state may be used to determine the efficacy of the drugs. Also, the neural state characterization may be used to identify patients who potentially will respond to certain AEDs. For example, prior to administering an AED to a patient, the patient's neural state is characterized. If neural state (as shown by extracted features, such as the STLmax and/or T-index values) are modulated by the AED so as to indicate a favorable modulation of the neural state, the patient may be considered to be a responder to the AED being tested. Also, this monitoring can be used to study the efficacy of AEDs in specific patient sub-populations.

One method of characterizing the patient's neural state comprises the analysis of dynamical characteristics of EEG signals. For example, modulation of specific dynamical conditions may be monitored and its effect on EEG dynamics is examined to understand the different neural states of the patient. In one embodiment, the neural state is at least partially characterized by higher values of a T-Index, a measure that indicates lower dynamical similarity in the EEG signal derived from electrodes located over widespread areas of the cerebral cortex. Typically, during an inter-ictal state, the T-index is high.

As is described by U.S. Pat. No. 6,304,775, epileptic seizures are typically preceded and accompanied by characteristic dynamical changes detectable in the spatiotemporal patterns of the EEG. In one particular embodiment, in which the neural state is characterized by STL max, seizures are preceded by convergence in the value of STLmax among specific EEG electrode sites, beyond that seen normally in the inter-ictal phase. This can be observed by monitoring STLmax values over time from EEG signals obtained using intracranial or scalp electrodes. In one embodiment, the STLmax values extracted from EEG signals are used to screen for drugs with anti-epileptic properties and also used to screen for patient responder subpopulations. The convergence of STLmax among critical electrodes can be measured by calculating a T-index, a normalized mean difference of the STLmax between selected electrodes. Thus, prior to a seizure, there has been found to be a decrease in the T-index, more than its normal fluctuation, as the values of STLmax converge. In some embodiments, the T-index is used in the screening methods described herein.

During a complex partial or secondarily generalized seizure, STLmax values calculated from all electrode sites tend to converge to a common value and fall abruptly in value. The postictal state is characterized by a gradual increase in the values of STLmax to the values characteristic of the interictal state and a divergence in values among electrode sites. This divergence is reflected by a rise in the value of the T-index. In another embodiment, these characteristics are used in the screening methods described herein. Not intending to be limited to one mechanism of action, it is believed that the convergence of STLmax values represents a dynamical entrainment among large areas of the epileptic brain. Further, it is believed that it is this entrainment that increases the likelihood of a seizure developing. This suggests that an intervention aimed at reducing the convergence, which causes the T-index to increase, could offer a protective effect and decrease the likelihood of a seizure.

As can be appreciated, while the above example use the T-Index and STLmax values as extracted features for characterizing neural state, it should be appreciated that such features are just examples of some useful features that may be used to characterize the patient's neural state, and that any combination of the features described herein and/or other suitable techniques known in the art may be used to characterize the patient's neural state to screen for drugs and to screen for patient responder subpopulations.

Dosage, Routes of Administration, and Formulations:

Yet another aspect of the present invention relates to formulations, routes of administration and effective doses for pharmaceutical compositions comprising a compound or combination of compounds of the instant invention. Such pharmaceutical compositions are used in the treatment, preferably prevention, of epilepsy, as described in detail above.

In some embodiments, the compounds may be used in combination with one or more other compounds or with one or more other forms. The two or more compounds may be formulated together, in the same dosage unit e.g. in one cream, suppository, tablet, capsule, or packet of powder to be dissolved in a beverage; or each compound may be formulated in a separate unit, e.g., two creams, two suppositories, two tablets, two capsules, a tablet and a liquid for dissolving the tablet, a packet of powder and a liquid for dissolving the powder, etc.

The compounds of the present invention may be administered as a pharmaceutically acceptable salt. The term "pharmaceutically acceptable salt" means those salts which retain the biological effectiveness and properties of the compounds used in the present invention, and which are not biologically or otherwise undesirable.

Typical salts are those of the inorganic ions, such as, for example, sodium, potassium, calcium, magnesium ions, and the like. Such salts include salts with inorganic or organic acids, such as hydrochloric acid, hydrobromic acid, phosphoric acid, nitric acid, sulfuric acid, methanesulfonic acid, p-toluenesulfonic acid, acetic acid, fumaric acid, succinic acid, lactic acid, mandelic acid, malic acid, citric acid, tartaric acid or maleic acid. In addition, if the compound(s) contain a carboxy group or other acidic group, it may be converted into a pharmaceutically acceptable addition salt with inorganic or organic bases. Examples of suitable bases include sodium hydroxide, potassium hydroxide, ammonia, cyclohexylamine, dicyclohexyl-amine, ethanolamine, diethanolamine, triethanolamine, and the like. A pharmaceutically acceptable ester or amide refers to those which retain biological effectiveness and properties of the compounds used in the present invention, and which are not biologically or otherwise undesirable. Typical esters include ethyl, methyl, isobutyl, ethylene glycol, and the like. Typical amides include unsubstituted amides, alkyl amides, dialkyl amides, and the like.

In some embodiments, a compound may be administered in combination with one or more other compounds, forms, and/or agents, e.g., as described above. Pharmaceutical compositions comprising combinations with one or more other active agents can be formulated to comprise certain molar ratios. The two compounds, forms and/or agents may be formulated together, in the same dosage unit e.g. in one cream, suppository, tablet, capsule, or packet of powder to be dissolved in a beverage; or each compound, form, and/or agent may be formulated in separate units, e.g., two creams, suppositories, tablets, two capsules, a tablet and a liquid for dissolving the tablet, a packet of powder and a liquid for dissolving the powder, etc.

If necessary or desirable, the compounds and/or combinations of compounds may be administered with still other agents. The choice of agents that can be co-administered with the compounds and/or combinations of compounds of the instant invention can depend, at least in part, on the condition being treated.

The compound(s) (or pharmaceutically acceptable salts, esters or amides thereof) may be administered per se or in the form of a pharmaceutical composition wherein the active compound(s) is in an admixture or mixture with one or more pharmaceutically acceptable carriers. A pharmaceutical composition, as used herein, may be any composition prepared for administration to a subject. Pharmaceutical compositions for use in accordance with the present invention may be formulated in conventional manner using one or more physiologically acceptable carriers, comprising excipients, diluents, and/or auxiliaries, e.g., which facilitate processing of the active compounds into preparations that can be administered. Proper formulation may depend at least in part upon the route of administration chosen. The compound(s) useful in the present invention, or pharmaceutically acceptable salts, esters, or amides thereof, can be delivered to a patient using a number of routes or modes of administration, including oral, buccal, topical, rectal, transdermal, transmucosal, subcutaneous, intravenous, and intramuscular applications, as well as by inhalation.

For oral administration, the compounds can be formulated readily by combining the active compound(s) with pharmaceutically acceptable carriers well known in the art. Such carriers enable the compounds of the invention to be formulated as tablets, including chewable tablets, pills, dragees, capsules, lozenges, hard candy, liquids, gels, syrups, slurries, powders, suspensions, elixirs, wafers, and the like, for oral ingestion by a patient to be treated. Such formulations can comprise pharmaceutically acceptable carriers including solid diluents or fillers, sterile aqueous media and various non-toxic organic solvents. Generally, the compounds of the invention will be included at concentration levels ranging from about 0.5%, about 5%, about 10%, about 20%, or about 30% to about 50%, about 60%, about 70%, about 80% or about 90% by weight of the total composition of oral dosage forms, in an amount sufficient to provide a desired unit of dosage.

Aqueous suspensions for oral use may contain compound(s) of this invention with pharmaceutically acceptable excipients, such as a suspending agent (e.g., methyl cellulose), a wetting agent (e.g., lecithin, lysolecithin and/or a long-chain fatty alcohol), as well as coloring agents, preservatives, flavoring agents, and the like.

In some embodiments, oils or non-aqueous solvents may be required to bring the compounds into solution, due to, for example, the presence of large lipophilic moieties. Alternatively, emulsions, suspensions, or other preparations, for example, liposomal preparations, may be used. With respect to liposomal preparations, any known methods for preparing liposomes for treatment of a condition may be used. See, for example, Bangham et al., *J. Mol. Biol.* 23: 238-252 (1965) and Szoka et al., *Proc. Natl. Acad. Sci. USA* 75: 4194-4198 (1978), incorporated herein by reference. Ligands may also be attached to the liposomes to direct these compositions to particular sites of action. Compounds of this invention may also be integrated into foodstuffs, e.g., cream cheese, butter, salad dressing, or ice cream to facilitate solubilization, administration, and/or compliance in certain patient populations.

Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; flavoring elements, cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP). If desired, disintegrating agents may be added, such as the cross-linked polyvinyl pyrrolidone, agar, or alginic acid or a salt thereof such as sodium alginate. The compounds may also be formulated as a sustained release preparation.

Dragee cores can be provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compounds.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for administration.

For injection, the compounds of the present invention may be formulated in aqueous solutions, preferably in physiologically compatible buffers such as Hank's solution, Ringer's solution, or physiological saline buffer. Such compositions may also include one or more excipients, for example, preservatives, solubilizers, fillers, lubricants, stabilizers, albumin, and the like. Methods of formulation are known in the art, for example, as disclosed in Remington's Pharmaceutical Sciences, latest edition, Mack Publishing Co., Easton P.

In addition to the formulations described previously, the compounds may also be formulated as a depot preparation. Such long acting formulations may be administered by implantation or transcutaneous delivery (for example subcutaneously or intramuscularly), intramuscular injection or use of a transdermal patch. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions according to the present invention may be in any form suitable for topical application, including aqueous, aqueous-alcoholic or oily solutions, lotion or serum dispersions, aqueous, anhydrous or oily gels, emulsions obtained by dispersion of a fatty phase in an aqueous phase (O/W or oil in water) or, conversely, (W/O or water in oil), microemulsions or alternatively microcapsules, microparticles or lipid vesicle dispersions of ionic and/or nonionic type. These compositions can be prepared according to conventional methods. Other than the compounds of the invention, the amounts of the various constituents of the compositions according to the invention are those conventionally used in the art.

In some preferred embodiments, the compounds of the present invention are delivered in soluble rather than suspension form, which allows for more rapid and quantitative absorption to the sites of action. In general, formulations such as jellies, creams, lotions, suppositories and ointments can provide an area with more extended exposure to the compounds of the present invention, while formulations in solution, e.g., sprays, provide more immediate, short-term exposure.

In some embodiments relating to topical/local application, the pharmaceutical compositions can include one or more penetration enhancers. For example, the formulations may comprise suitable solid or gel phase carriers or excipients that increase penetration or help delivery of compounds or combinations of compounds of the invention across a permeability barrier, e.g., the skin. Many of these penetration-enhancing compounds are known in the art of topical formulation, and include, e.g., water, alcohols (e.g., terpenes like methanol, ethanol, 2-propanol), sulfoxides (e.g., dimethyl sulfoxide, decylmethyl sulfoxide, tetradecylmethyl sulfoxide), pyrrolidones (e.g., 2-pyrrolidone, N-methyl-2-pyrrolidone, N-(2-hydroxyethyl)pyrrolidone), laurocapram, acetone, dimethylacetamide, dimethylformamide, tetrahydrofurfuryl alcohol, L-α-amino acids, anionic, cationic, amphoteric or nonionic surfactants (e.g., isopropyl myristate and sodium lauryl sulfate), fatty acids, fatty alcohols (e.g., oleic acid), amines, amides, clofibric acid amides, hexamethylene lauramide, proteolytic enzymes, α-bisabolol, d-limonene, urea and N,N-diethyl-m-toluamide, and the like Additional examples include humectants (e.g., urea), glycols (e.g., propylene glycol and polyethylene glycol), glycerol monolaurate, alkanes, alkanols, ORGELASE, calcium carbonate, calcium phosphate, various sugars, starches, cellulose derivatives, gelatin, and/or other polymers. In some embodiments, the pharmaceutical compositions will include one or more such penetration enhancers.

In some embodiments, the pharmaceutical compositions for local/topical application can include one or more antimicrobial preservatives such as quaternary ammonium compounds, organic mercurials, p-hydroxy benzoates, aromatic alcohols, chlorobutanol, and the like.

The compounds may be rectally delivered solutions, suspensions, ointments, enemas and/or suppositories comprising a compound or combination of compounds of the present invention.

Also the compounds can be delivered effectively with aerosol solutions, suspensions or dry powders comprising a compound or combination of compounds of the present invention. The aerosol can be administered through the respiratory system or nasal passages. For example, one skilled in the art will recognize that a composition of the present invention can be suspended or dissolved in an appropriate carrier, e.g., a pharmaceutically acceptable propellant, and administered directly into the lungs using a nasal spray or inhalant. For example, an aerosol formulation comprising a compound of the invention can be dissolved, suspended or emulsified in a propellant or a mixture of solvent and propellant, e.g., for administration as a nasal spray or inhalant. Aerosol formulations may contain any acceptable propellant under pressure, preferably a cosmetically or dermatologically or pharmaceutically acceptable propellant, as conventionally used in the art.

An aerosol formulation for nasal administration is generally an aqueous solution designed to be administered to the nasal passages in drops or sprays. Nasal solutions can be similar to nasal secretions in that they are generally isotonic and slightly buffered to maintain a pH of about 5.5 to about 6.5, although pH values outside of this range can additionally be used. Antimicrobial agents or preservatives can also be included in the formulation.

An aerosol formulation for inhalations and inhalants can be designed so that the compound or combination of compounds of the present invention is carried into the respiratory tree of the subject when administered by the nasal or oral respiratory route. Inhalation solutions can be administered, for example, by a nebulizer. Inhalations or insufflations, comprising finely powdered or liquid drugs, can be delivered to the respiratory system as a pharmaceutical aerosol of a solution or suspension of the compound or combination of compounds in a propellant, e.g., to aid in disbursement. Propellants can be liquefied gases, including halocarbons, for example, fluorocarbons such as fluorinated chlorinated hydrocarbons, hydrochlorofluorocarbons, and hydrochlorocarbons, as well as hydrocarbons and hydrocarbon ethers.

Halocarbon propellants useful in the present invention include fluorocarbon propellants in which all hydrogens are replaced with fluorine, chlorofluorocarbon propellants in which all hydrogens are replaced with chlorine and at least one fluorine, hydrogen-containing fluorocarbon propellants, and hydrogen-containing chlorofluorocarbon propellants. Halocarbon propellants are described in Johnson, U.S. Pat. No. 5,376,359, issued Dec. 27, 1994; Byron et al., U.S. Pat. No. 5,190,029, issued Mar. 2, 1993; and Purewal et al., U.S. Pat. No. 5,776,434, issued Jul. 7, 1998. Hydrocarbon propellants useful in the invention include, for example, propane, isobutane, n-butane, pentane, isopentane and neopentane. A blend of hydrocarbons can also be used as a propellant. Ether propellants include, for example, dimethyl ether as well as the ethers. An aerosol formulation of the invention can also comprise more than one propellant. For example, the aerosol formulation can comprise more than one propellant from the same class, such as two or more fluorocarbons; or more than one, more than two, more than three propellants from different classes, such as a fluorohydrocarbon and a hydrocarbon. Pharmaceutical compositions of the present invention can also be dispensed with a compressed gas, e.g., an inert gas such as carbon dioxide, nitrous oxide or nitrogen.

Aerosol formulations can also include other components, for example, ethanol, isopropanol, propylene glycol, as well as surfactants or other components such as oils and detergents. These components can serve to stabilize the formulation and/or lubricate valve components.

The aerosol formulation can be packaged under pressure and can be formulated as an aerosol using solutions, suspensions, emulsions, powders and semisolid preparations. For example, a solution aerosol formulation can comprise a solution of a compound of the invention in (substantially) pure propellant or as a mixture of propellant and solvent. The solvent can be used to dissolve the compound and/or retard the evaporation of the propellant. Solvents useful in the invention include, for example, water, ethanol and glycols. Any combination of suitable solvents can be use, optionally combined with preservatives, antioxidants, and/or other aerosol components.

An aerosol formulation can also be a dispersion or suspension. A suspension aerosol formulation may comprise a suspension of a compound or combination of compounds of the instant invention and a dispersing agent. Dispersing agents useful in the invention include, for example, sorbitan trioleate, oleyl alcohol, oleic acid, lecithin and corn oil. A suspension aerosol formulation can also include lubricants, preservatives, antioxidant, and/or other aerosol components.

An aerosol formulation can similarly be formulated as an emulsion. An emulsion aerosol formulation can include, for example, an alcohol such as ethanol, a surfactant, water and a propellant, as well as a compound or combination of compounds of the invention. The surfactant used can be nonionic, anionic or cationic. One example of an emulsion aerosol formulation comprises, for example, ethanol, surfactant, water and propellant. Another example of an emulsion aerosol formulation comprises, for example, vegetable oil, glyceryl monostearate and propane.

Pharmaceutical compositions suitable for use in the present invention include compositions wherein the active ingredients are present in an effective amount, i.e., in an amount effective to achieve therapeutic and/or prophylactic benefit in an epileptic condition. The actual amount effective for a particular application will depend on the condition or conditions being treated, the condition of the subject, the formulation, and the route of administration, as well as other factors known to those of skill in the art. Determination of an effective amount of a compound is well within the capabilities of those skilled in the art, in light of the disclosure herein, and will be determined using routine optimization techniques.

The effective amount for use in humans can be determined from animal models. For example, a dose for humans can be formulated to achieve circulating, liver, topical and/or gastrointestinal concentrations that have been found to be effective in animals. One skilled in the art can determine the effective amount for human use, especially in light of the animal model experimental data.

The effective amount when referring to a compound or combination of compounds of the invention will generally mean the dose ranges, modes of administration, formulations, etc., that have been recommended or approved by any of the various regulatory or advisory organizations in the medical or pharmaceutical arts (e.g., FDA, AMA) or by the manufacturer or supplier. Effective amounts can be found, for example, in the Physicians Desk Reference.

EXAMPLES

In some embodiments, administration of compounds of the present invention may be intermittent, for example administration once every two days, every three days, every five days, once a week, once or twice a month, and the like. In some embodiments, the amount, forms, and/or amounts of the different forms may be varied at different times of administration based on the neural state and/or prediction of the seizure.

The following description provides one example of a predictive algorithm that may be used to monitor the patient's neural state to monitor the effect of acute dosages of AEDs. As can be appreciated any of the aforementioned predictive algorithms may be used by the present invention to predict the onset of a seizure, and the present invention is not limited to the following example.

Chronic dosages of anti-epileptic drugs (AEDs) have been shown to improve seizure control in patients with partial epilepsy. Previous studies have indicated that the development and resolution of seizures are associated with measurable changes in the spatiotemporal dynamics of EEG signals. The present pilot study is designed to show the effect of an acutely administered dosage of an AED on the patient's propensity for a future seizure, as characterized by a patient's neural state. In one embodiment, the patient's neural state is characterized by classifying the patient's dynamical characteristics of the EEG signals. Specifically, an acute dosage (the FDA approved dosage or some reduction of the FDA approved dosage) of select AEDs or other suitable pharmacological agents (referred to in this example as "AED"), under specific dynamical conditions, will modulate the neural state or EEG dynamics, maintain the neural state in a desired range, keep the neural state from progressing outside a desired range, preventing the neural state from entering a critical range, or if outside the desired range to return to the desired range, which comprise states in which seizures are less likely to occur. In one embodiment, this neural state may be characterized by higher values of the T-index, a measure that indicates lower dynamical similarity in the EEG signal derived from electrodes located over widespread areas of the cerebral cortex. However, in other embodiments, the patient's propensity for a future seizure may be characterized by some other features, including any of the other neural state features described above.

The exact EEG profile, optimum feature(s) measured to characterize the neural state, and the particular AED for treatment vary from patient to patient or between patient groups. It is thus possible to analyze the specifics of the EEG signal measured, the optimum drug dosage, correlate dosages to the prediction horizon and optimize the therapy utilized, whether a drug or other therapy, for an individual patient or subpopulations of patients. The effect of AEDs on dynamical characteristics of EEG signals are analyzed to determine if an acute dosage of a particular AED during the interictal state results in a perturbation of the neural state (e.g., an increase of the T-index), which may reduce the patient's propensity for a seizure and provide a protective effect against the occurrence of seizures. It can also help identify for which patients this drug and prediction algorithm are most effective.

Specific Aim 1:

Determine the EEG electrode groups that show the most convergence of STLmax values prior to the first recorded seizure and also demonstrate the resetting after the seizure. These electrode groups are then used for detecting the fluctuations in T-index.

Specific Aim 2:

Determine the optimal parameter settings for an automated seizure prediction system. The determination is based on the evaluation of the sensitivity and specificity of the prediction algorithm.

Specific Aim 3:

Identify patients who exhibit consistent identifiable correlations between T-index fluctuations and seizure propensity.

Specific Aim 4:

In patients that show meaningful T-index fluctuations, determine whether acute dosages of AEDs influence the T-index.

Epileptic seizures are typically preceded and accompanied by characteristic dynamical changes detectable in the spatiotemporal patterns of the EEG. Specifically, seizures are preceded by convergence in the value of STLmax among specific EEG electrode sites, beyond that seen normally in the interictal phase. This can be observed by monitoring STLmax values over time in EEG recordings obtained using intracranial or scalp electrodes. See U.S. Pat. No. 6,304,775.

The convergence of STLmax among the critical electrodes can be measured by calculating a T-index, a normalized mean difference of the STLmax between selected electrodes. Thus, prior to a seizure, there is a decrease in the T-index, more than its normal fluctuation, as the values of STLmax converge.

During a complex partial or secondarily generalized seizure recorded from intracranial EEG electrodes, STLmax values calculated from all electrode sites converge to a common value and fall abruptly in value. The postictal state is characterized by a gradual increase in the values of STLmax to the values characteristic of the interictal state and a divergence in values among electrode sites. This divergence is reflected by a rise in the value of the T-index.

Not intending to be limited to one mechanism of measuring neural state, it is believed that the convergence of STLmax values represents a dynamical entrainment among large areas of the epileptic brain. Further, it is believed that it is this entrainment that increases the likelihood of a seizure developing. This suggests that an intervention aimed at reducing the convergence, causing the T-index to increase, offers a protective effect and decreases the propensity of a seizure occurring. Further, as described herein, acute dosages of AEDs exert an anticonvulsant effect by altering brain dynamics and increasing disentrainment of regions in the brain.

The spatiotemporal dynamic effects of an acute dosage of an AED that interface with automated seizure prediction algorithms are investigated. The prediction algorithm may be based on dynamical analysis of EEG signals, optimization algorithms for selection of critical electrode groups, and statistical pattern recognition methods, as described above.

One embodiment of the seizure prediction algorithm is based on the idea that seizures occur in a dynamical state characterized by comparative spatiotemporal order, which can be measured by the T-index, a value that indicates standard mean difference in the value of STLmax (an indicator of how ordered the signal from an individual channel is during a given time window), among multiple EEG electrode sites. A low T-index reflects convergence of STLmax values among electrode sites, indicating spatial order.

Figure 18:
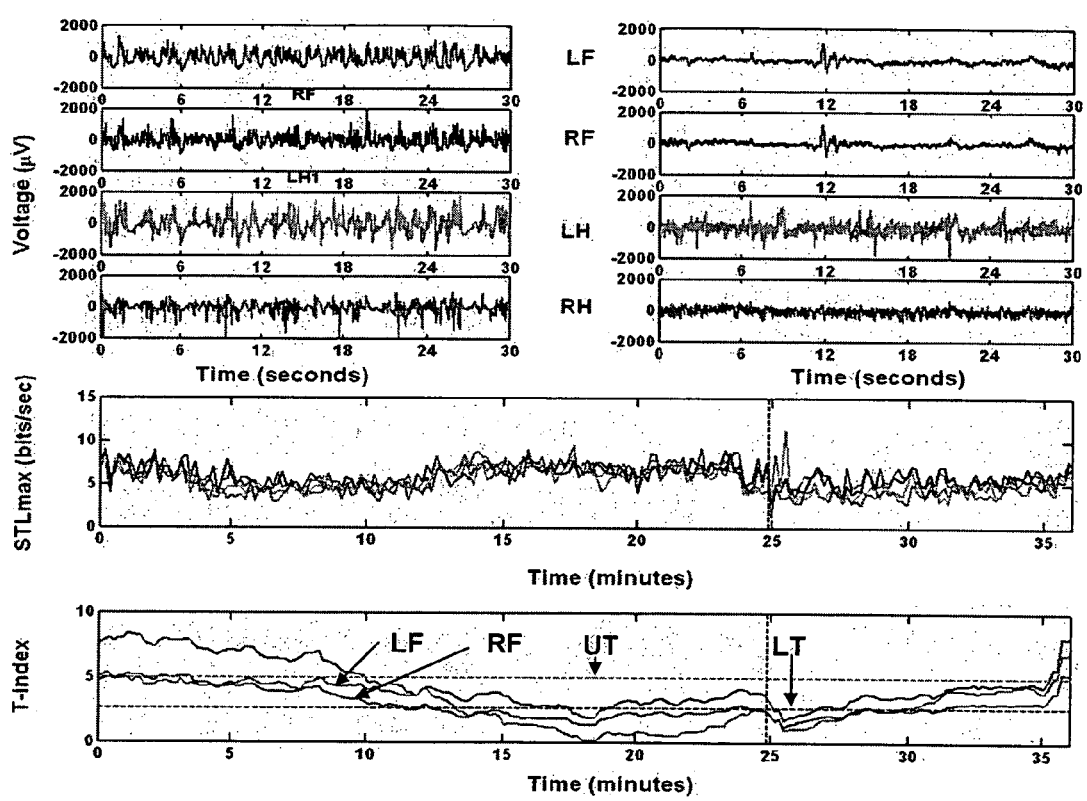
FIG. 18 illustrates a graph of left hippocampus LH and right hippocampus RH before stimulation (left) and 30 seconds after stimulation (right) of the left hippocampus.

In assessing the usefulness of the T-Index as a viable feature for characterizing the neural state, investigations in the rodent chronic limbic epilepsy model indicate that direct electrical stimulation to the hippocampus when the T-index is low can cause the T-index to rise back to higher values and delay seizure onset. In FIG. 18, the upper tracings labeled "voltage" depict 30 seconds of EEG (recorded from the left frontal cortex LF, right frontal cortex RF, left hippocampus LH and right hippocampus RH) before stimulation (left) and 30 seconds after stimulation (right) of the left hippocampus. Note the change in EEG to a less ordered (more chaotic) appearing pattern. The middle plot shows STLmax profiles of EEG signals derived from the same electrodes, over a 35 minute period. Note that the hippocampal stimulus was given approximately 25 minutes into the tracing. The lower plot is a T-index, indicating the standard mean difference of STLmax values between the LH electrode and each of the other electrodes. The T-index for LF and RF converge approximately 15 minutes into the trace (fall below the lower threshold LT). After the stimulus, the T-index for LF and RF are back above the upper threshold UT. Acute dosages of selected AEDs can be analyzed for similar effects on the T-Index in patient sub-populations.

Figure 19:
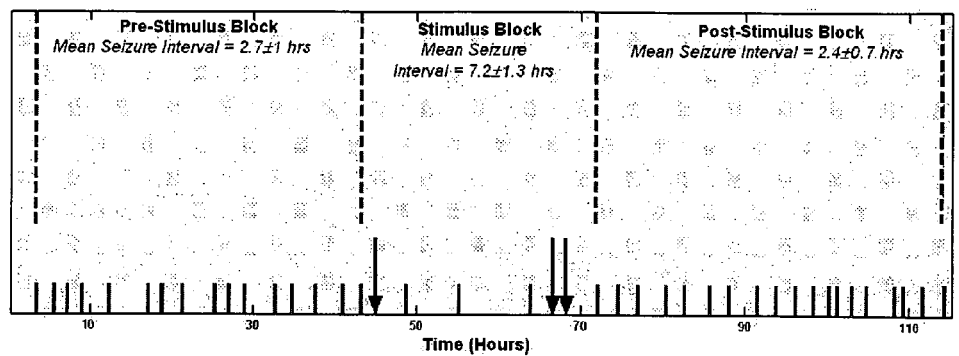
FIG. 19 shows a seizure pattern observed in a rodent with chronic limbic epilepsy undergoing continuous EEG monitoring with automated seizure warning in place.

FIG. 19 shows a seizure pattern observed in a rodent with chronic limbic epilepsy undergoing continuous EEG monitoring with automated seizure warning in place. During the Pre-Stimulus Block of time, the mean seizure interval was 2.7 hours (1.0 sd). During the stimulus block, the left hippocampus was stimulated for 10 seconds at 125 Hz each time the T-index fell below the lower threshold. During the Stimulus Block of time, the mean seizure interval increased to 7.2 hours (1.3 sd). Upon discontinuation of stimulation, the mean seizure interval dropped back to 2.4 hours ((0.7 sd). This suggests that electrical stimulation not only reset the T-index to higher values, but also served to reduce seizure frequency.

Acute dosages of AEDs can be analyzed for similar effects on T-Index in various patient sub-populations.

The protocol may be conducted in 2 phases. The purpose of Phase 1 is to identify patients who consistently show a significant change in the T-index, derived from EEG recordings derived from scalp electrodes, prior to their complex partial or generalized seizures. The subset of EEG electrode sites that provide the most meaningful data by training an automated computer-based seizure prediction algorithm may be identified. In Phase 2, an acute dosage of an AED is taken during the interictal phase to increase the T-index and reduce the risk of a seizure.

Phase 1:

The goal of phase 1 is to train the automated seizure prediction algorithm, that is, to determine the critical electrode groups for monitoring and the optimal parameter setting of the algorithm. See U.S. Patent Application Publication Nos. US2004/0127810 A1 and US2004/0122335. At the time of admission, the patient's interval, medical and neurological history, is obtained and physical and neurological examinations are performed. Each patient may be accompanied by a family member or close friend who is familiar with their seizure disorder. This person assists by alerting the staff in the event that the patient has a seizure and also assists the patient, as needed.

Training of the ASPA includes determining (1) the critical electrode groups that show the greatest change between interictal levels and those found during a seizure, and (2) the proper parameters of the algorithm that achieve an acceptable performance for recognizing unique spatiotemporal dynamical pattern for the specific patient. At least 3 seizures should be recorded during this phase to train the ASPA.

Patients that had at least 3 seizures and for whom seizures were consistently preceded by a definite drop in the T-index stay in the study to complete phase 2, another 7 day long hospital stay. If not possible, patients are discharged and re-admitted within one month for phase 2. Eighty percent of patients completing phase 1 will likely be eligible for phase 2.

Phase 2:

The purpose of this phase of the study is to determine whether taking an acute dosage of a particular AED, during the preictal phase elevates the T-index, which may provide a protective effect against the occurrence of seizures. Phase 2 occurs immediately following, or within one month after, completion of phase 1.

The ASPA system may monitor patient's EEG recordings continuously for 7 days. When the ASPA detects a drop in the T-index below the lower threshold value, it activates a warning device (such as a patient communication assembly 18—FIG. 2) which will alert, instruct and/or provide a recommendation to the patient and anyone else in the room with an audio and visual alert from a personal computer in the patient's room designated for this study. The patient, patient's companion, or the proper attending medical staff then administers a prescribed AED, as suggested by the ASPA or the patient's caregiver.

For a randomly assigned half of the patients, the first 3.5 days are "No-AED" trial and the last 3.5 days "AED" trial, and vice versa for the other half of the patients. When a patient is under "AED" trial, the patient, guardian or kin, or appropriate tending medical staff member respond to the algorithm's seizure prediction alert and provide an acute dosage of the AED to the patient. When a patient is under "No-AED" trial, no AED is given to the patient.

This phase investigates how dynamical properties of EEG are changed by an acute dosage of an AED. To accomplish this, one or more online real-time ASPA software is interfaced with the EEG acquisition system. While the acquisition system is recording EEG from the patient, the seizure prediction algorithm simultaneously analyze the dynamical properties of the EEG and the dynamical measures are displayed on an interfaced computer. During the "AED" trial, when the neural state (e.g., dynamical measures T-index of STLmax) indicate that the patient has an elevated propensity for a seizure, a "Warning" sign or "Instruction/recommendation" is displayed on the analysis computer and an AED may be administered by the patient, patient's guardian or kin, or the proper attending medical staff. During the "No-AED" trial, an AED is not administered. Since the T-index values are low at the time when a "Warning" or "Instruction/recommendation" is given, the T-index values should be increased to a higher level (as observed during normal interictal state) by AED intervention.

The EEG signals are acquired using a standard clinical data acquisition machine at a sampling rate of 400-500 Hz and are transferred offline into one of the research servers for post-hoc analysis. Medications taken, seizures reported or observed and level of awareness are documented during each phase of the study.

Statistical Analysis:

To test the hypothesis, for each patient, the proportion of AED interventions that significantly elevate the T-index values are estimated, as well as the proportion of interventions that significantly elevate the T-index for a time period equal to or greater than the estimated duration for which the patient is at an elevated propensity for a seizure, as derived from previous studies. Same proportions under "No-AED" trial are also estimated and are used as controlled outcomes of the study. Interventions (AED or No-AED) are repeated at least 10 times in each trial for the estimation of the proportions.

Figure 20:
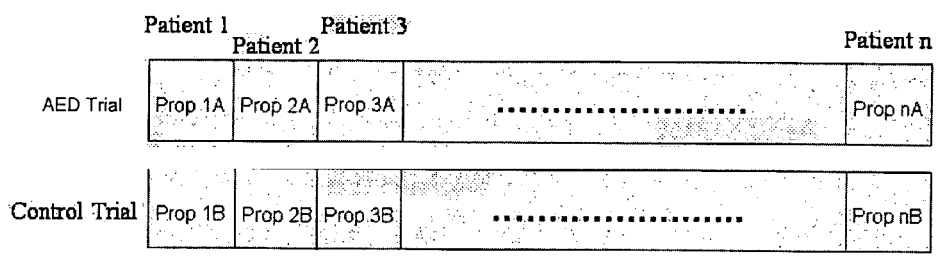
FIG. 20 illustrates a sample response table.

Without the assumption of underlying distribution, a two-sided Wilcoxon signed-rank test (a nonparametric analogue to the paired-T test) is applied to test the mean proportion difference between "No-AED" trials and "AED" trials. Each outcome proportion is estimated from at least 10 trials in each patient. Therefore, we will have a response table similar to that shown in FIG. 20.

Randomization: Each patient is randomly assigned to one of the two groups of treatment order: "No-AED" to "AED" and "AED" to "No-AED".

Sample Size: (N=16, 8 of which receive "No-AED" treatment first, and the remaining 8 receive "AED" treatment first). For an overall two-sample pair-T test, a study of 16 subjects under a normal distributional set-up, with significance level of 0.05, has 96% power to detect a difference (effect size) of 1.0 standard deviation in the dependent variable from the null hypothesized value of 0.0. Given a sample size of 16, the power of the exact signed-rank test to detect a mean of 1.0 standard deviations from the null hypothesized value of zero, $P<0.05$ two-sided is about 95%. (Based on 100,000 simulations, the empirical power was 94.8%). A t-test would have 96% power, but is not robust to departures from normality, whereas the sign-ranked test yields a valid p-value under any symmetric null distribution about zero for the paired difference.

CONCLUSION

While all the above is a complete description of the preferred embodiments of the inventions, various alternatives, modifications, and equivalents may be used. The system of the present invention may be used as an add-on to existing neural stimulation devices. For example, the Cyberonics VNS Therapy system or the Medtronic Intercept DBS Therapy may be improved by using the systems and methods of the present invention. The systems of the present invention may be used to monitor the patient's neural state and once the system determines a heightened risk of a seizure, the patient may be instructed to activate the VNS therapy.

What is claimed:

1. A system for monitoring a patient, the system comprising:
   a device assembly that is configured to:
      process one or more patient parameters to characterize the patient's propensity for an onset of a first neurological event,
      provide a first output that is indicative of a first appropriate action for responding to the first neurological event, wherein the first appropriate action is selected from a plurality of appropriate actions based on the patient's propensity for the onset of the first neurological event,
      process the one or more patient parameters to characterize the patient's propensity for an onset of a second neurological event occurring subsequent to the first neurological event, and
      provide a second output that is indicative of a second appropriate action for responding to the second neurological event, wherein the second appropriate action is different from the first appropriate action and is selected from the plurality of appropriate actions based on the patient's propensity for the onset of the second neurological event; and
   a communication assembly in communication with the device assembly, wherein the communication assembly communicates to the patient and/or a health care provider a first signal that is indicative of the first appropriate action for responding to the first neurological event and communicates to the patient and/or the health care provider a second signal that is indicative of the second appropriate action for responding to the second neurological event.

2. The system of claim 1 wherein at least one of the first and second neurological events comprises a seizure.

3. The system of claim 1 wherein the device assembly characterizes the patient's propensity for the onset of the second neurological event by calculating a patient neural state and processing the patient neural state to generate the second output that is indicative of the second appropriate action.

4. The system of claim 3 wherein the device assembly provides the second output when the calculated patient neural state is indicative of the onset of the second neurological event within a prediction time horizon of at least one of 30 seconds, 1 minute, 5 minutes, 10 minutes, 30 minutes, and 60 minutes.

5. The system of claim 1 wherein the one or more patient parameters comprise one or more physiological signals from the patient, a patient history, and patient feedback.

6. The system of claim 5 wherein the device assembly characterizes the patient's propensity for the onset of at least one of the first and second neurological events by extracting one or more features from the one or more physiological signals and classifying the extracted features.

7. The system of claim 1 wherein at least one of the first and second signals indicates that the patient take at least one type of pharmacological agent.

8. The system of claim 7 wherein at least one of the first and second signals indicates that the patient take a specified dosage of the at least one type of pharmacological agent, wherein the specified dosage is based on the patient's propensity for the onset of the at least one of the first and second neurological events.

9. The system of claim 8 wherein at least one of the first and second signals indicates that the patient take at least one of a reduction of a normal dosage of the at least one type of pharmacological agent and an increase of the normal dosage of the at least one type of pharmacological agent.

10. The system of claim 1 wherein at least one of the first and second signals indicates a recommendation to the patient to make a behavioral modification.

11. The system of claim 10 wherein the behavioral modification comprises at least one of lying down, turning off lights, interrupting working, touching the face, hyperventilating, hypoventilating, holding breath, performing a valsalva maneuver, applying an external stimulator, applying transcutaneous electrical neural stimulation, and cessation of an activity.

12. The system of claim 1 further comprising:
   a patient interface assembly for delivering a therapy to the patient when the one or more patient parameters reaches a threshold.

13. The system of claim 12 wherein the patient interface assembly comprises one or more electrodes and the therapy comprises electrical stimulation,
   wherein the electrical stimulation is delivered to the patient through the one or more electrodes and one or more stimulation parameters of the electrical stimulation are dependent on the one or more patient parameters.

14. The system of claim 13 wherein the one or more electrodes are configured to deliver the electrical stimulation to a vagus nerve.

15. The system of claim 12 wherein the patient interface assembly comprises an implantable medication dispenser.

16. The system of claim 1 wherein at least a portion of the device assembly is adapted to be implanted within the patient's body and the communication assembly is adapted to be disposed external to the patient's body.

17. The system of claim 1 wherein the communication assembly comprises at least one of a visual device, a tactile device, and an audio device.

18. The system of claim 3 wherein the device assembly is configured to transmit the calculated neural state to the communication assembly and the communication assembly is adapted to communicate the neural state to the patient.

19. The system of claim 18 wherein the device assembly is configured to transmit the calculated neural state to the patient substantially in real-time.

20. The system of claim 1 further comprising:
   a clinician communication assembly that is in communication with at least one of the communication assembly and the device assembly.

21. The system of claim 1 wherein the system does not deliver a therapy to the patient.

22. The system of claim 1 wherein the device assembly is configured to select at least one of the first and second appropriate actions from the plurality of appropriate actions by selecting a dosage from a plurality of dosages for one or more pharmacological agents based on at least one of the first and second neurological events.

23. The system of claim 1 wherein the device assembly is configured to select at least one of the first and second appropriate actions from the plurality of appropriate actions by selecting a pharmacological agent from a plurality of pharmacological agents based on at least one of the first and second neurological events.

24. The system of claim 1 wherein the device assembly is configured to select at least one of the first and second appropriate actions from the plurality of appropriate actions by selecting an electrical stimulation parameter from a plurality of electrical stimulation parameters based on at least one of the first and second neurological events.

25. The system of claim 1 wherein at least one of the first and second appropriate actions is at least one of vagus nerve stimulation, intracranial stimulation, tactile stimulation, and pharmacological intervention.

* * * * *